С008465983В1

(12) United States Patent
Lopez et al.

(10) Patent No.: US 8,465,983 B1
(45) Date of Patent: *Jun. 18, 2013

(54) DETECTION AND DELIVERY SYSTEMS UTILIZING SUPPORTED LIPID BILAYERS

(76) Inventors: Gabriel P. Lopez, Albuquerque, NM (US); Reema Zeineldin, Albuquerque, NM (US); Menake E. Piyasena, South Pasadena, CA (US); Sireesha Chemburu, Albuquerque, NM (US)

( * ) Notice: Subject to any disclaimer, the term of this patent is extended or adjusted under 35 U.S.C. 154(b) by 694 days.

This patent is subject to a terminal disclaimer.

(21) Appl. No.: 11/466,046

(22) Filed: Aug. 21, 2006

Related U.S. Application Data

(60) Provisional application No. 60/709,603, filed on Aug. 19, 2005, provisional application No. 60/709,926, filed on Aug. 19, 2005.

(51) Int. Cl.
*G01N 21/00* (2006.01)

(52) U.S. Cl.
CPC ..................................... *G01N 21/00* (2013.01)
USPC ............. 436/164; 435/7.1; 435/7.2; 436/172; 436/518; 436/524

(58) Field of Classification Search
None
See application file for complete search history.

(56) References Cited

U.S. PATENT DOCUMENTS

| 6,284,375 | B1 * | 9/2001 | Jin et al. ........................ 428/403 |
| 6,544,732 | B1 * | 4/2003 | Chee et al. ......................... 435/6 |
| 6,761,877 | B2 * | 7/2004 | Barbera-Guillem ........... 424/9.6 |
| 7,514,267 | B1 * | 4/2009 | Lopez et al. ................... 436/164 |
| 2003/0232396 | A1 * | 12/2003 | Mathew et al. ................ 435/7.2 |
| 2004/0005352 | A1 * | 1/2004 | Lopez et al. ..................... 424/450 |
| 2004/0109887 | A1 * | 6/2004 | Wyatt et al. .................... 424/450 |
| 2005/0123563 | A1 * | 6/2005 | Doranz et al. .............. 424/204.1 |

OTHER PUBLICATIONS

Jones, Surfactant Interactions with Biomembranes and Proteins, Chemical Society Reviews, vol. 21, 1992, pp. 127-136.*
Kazakov et al., Chemiluminsecence in the oxidation of europium B-diketonates by dimethyldioxirane, Mendeleev Communications, Electronic Version, Issue 5, 2001, pp. 1-2.*

* cited by examiner

*Primary Examiner* — Gary W Counts
(74) *Attorney, Agent, or Firm* — Gonzales Patent Services; Ellen Gonzales

(57) ABSTRACT

The invention relates to lipid bilayer coated beads and methods of using those beads in delivery systems, in immunoassays, in analytical assays and the like.

15 Claims, 34 Drawing Sheets

FIG. 8 (con't)
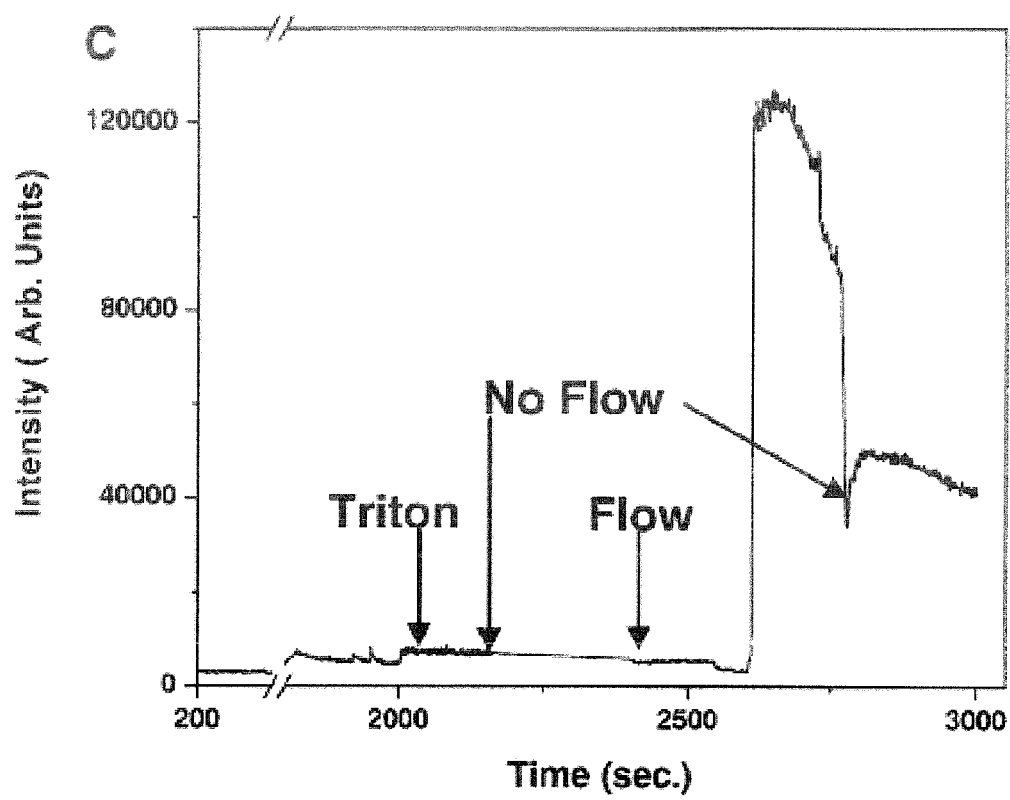

Drug-Encapsulated
Porous Particles with
immobilized Neutotoxin
Receptors

DETECTION AND DELIVERY SYSTEMS UTILIZING SUPPORTED LIPID BILAYERS

RELATED APPLICATIONS

This application claims the benefit under 35 U.S.C. 119(e) of U.S. Provisional Application Ser. No. 60/709,603, filed Aug. 19, 2005, and of U.S. Provisional Application Ser. No. 60/709,926, filed Aug. 19, 2005, the contents of which are incorporated herein in their entirety.

STATEMENT OF GOVERNMENT RIGHTS

The invention described herein was made with United States Government support under Grant Numbers EEC0210835 and CTS0332315 awarded by the National Science Foundation and grant number EB00264 awarded by the National Institutes of Health. The United States Government has certain rights in this invention.

FIELD OF THE INVENTION

The invention relates to beads containing detectable dyes where the bead is coated with a lipid bilayer. The invention also relates to assay methods involving detection of lipid bilayer-disruption of the present lipid-bilayer coated beads. The lipid bilayer coated beads and detection methods are useful for analyzing the properties of lipid bilayers and for detecting analytes.

BACKGROUND OF THE INVENTION

An understanding of interactions between membrane active biomolecules, test agents and surfactants on model lipid bilayer membranes is needed for many purposes, including, for example, for drug design and for developing an understanding of complex interactions in native biological membranes. The effects of detergents like TRITON X-100 detergent, sodium dodecylsulfate, and octyl glucoside on phospholipid membranes have been studied widely. Detergents solubilize the membrane by forming detergent-lipid mixed micelles. Some membrane binding biomolecules also appear to affect the integrity and functionality of cell membranes. For example, biomolecules can disrupt membranes either by forming channels or pores through the lipid bilayer, or by complete solubilization.

Membrane active proteins such as α-toxin, α-hemolysin, streptolysin-O, tetanus toxin and membrane active peptides such as anti microbial peptides (AMP) (e.g., alameticin, nagainin, melittin and gamicidin) are few of the biomolecules that are known to disrupt lipid membranes.

Most disruption studies utilizing model membrane systems have used lipid vesicles or supported lipid membranes (SLM) on flat surfaces. In such studies, the disruption is mainly analyzed by monitoring the release of trapped compounds (mainly from vesicles) or by monitoring the change in physical properties (vesicles and SLM). However, lipid vesicles are instable and difficult. Supported lipid membranes on flat surfaces tend to be more robust than lipid vesicles and also allow spectroscopic analysis of the membranes. The instability and poorly defined structures of lipid vesicles limit their utility and essentially preclude their use in miniaturized technologies such as microfluidics. Disruption studies on supported lipid membranes on flat surfaces also have limited for sensitive technologies such as fluorescence microscopy. Thus, lipid vesicles and supported lipid membranes on flat surfaces cannot readily be used in applications such as microfluidics. Part of the problem with lipid vesicles and supported lipid membranes on flat surfaces is due to the difficulties faced when trying to integrate these membranes into analytical and other devices.

Thus, new model membrane systems methods for analyzing membrane structure are needed. Such membranes and methods can be used in clinical, environmental, and bioanalytical applications.

SUMMARY OF THE INVENTION

The invention relates to new and sensitive supported lipid bilayer membrane systems and methods of using the supported lipid bilayer systems, for example, in analytical assays and detection methods. The membrane systems provided by the invention include lipid membranes supported on porous microspheres or microbeads. These beads are stable and can, for example, be used in immunoassays, in detection methods and for analysis of membrane structures while in suspension, while in columns and while in microfluidic systems. In other embodiments, the analysis of membrane structures, detection methods and immunoassays can be performed while using flow cytometry.

Thus, one aspect of the invention is a method of identifying a test agent that disrupts a lipid bilayer, which comprises (a) contacting a test agent with bead that has a first coating comprising a detectable label and second coating comprising a lipid bilayer, where the second coating is encloses the detectable label with the lipid bilayer, and (b) observing whether a signal from the detectable label is altered by the test agent. A substantial signal can be emitted by the detectable label on the bead prior to addition of the test agent. In some embodiments, the bead is non-porous and is coated with a polymeric dye or label that changes its signal when the lipid bilayer is disrupted. Thus, an altered signal from the detectable label can be observed when the test agent disrupts the lipid bilayer. For example, the signal can be altered by a quenching molecule present in solution surrounding the bead. Use of such a quenching molecule can lead to a reduced signal when the test agent disrupts the lipid bilayer. Detection of disruption of the lipid bilayer can, for example, be by use of flow cytometry or fluorometry. Examples of a detectable label that can be used to coat the bead include a fluorescent polymer, a fluorescent dye, an ion-sensitive dye, a pH-sensitive dye, an enzyme, a chemiluminescent molecule, a chromophore, an enzyme substrate, an enzyme cofactor, or an enzyme inhibitor. In one embodiment, the detectable label is a cationic polyelectrolyte poly(p-phenylene-ethynylene) fluorescent dye. Test agents that can be used in the methods of the invention include, for example, small molecules, drugs, toxins, polypeptides, peptides, antigens, antibodies, enzymes, receptors, ligands, nucleic acids, viruses, liposomes, lipids, surfactants, toxins or a combination thereof. The method can be adapted to be an immunoassay or a competitive immunoassay. Moreover, to simulate reactions that may occur in vivo, the lipid bilayer can include protein as well as lipid. For example, the protein can be a cell membrane protein, antibody, immunoreceptor or a cellular receptor. In some embodiments, it may be helpful to utilize a lipid bilayer that includes a lipid with a covalently attached linker. Alternatively, such a linker can be attached to the bead. Such linkers can include, for example, an alkylene chain, a peptide, a glycan, a lipid, biotin or streptavidin. In some embodiments, the linker is also attached to an antigen or antibody.

Another aspect of the invention is an assay for detecting an antibody, which comprises: (a) obtaining a lipid bilayer coated bead that displays an antigen, wherein below the lipid bilayer the bead is coated with a detectable label; (b) contacting the bead with a test agent that may contain the antibody to form a bead-test agent mixture; and (c) observing whether a signal from the detectable label is altered. In some embodiments, antibody-generated ozone or hydrogen peroxide can disrupt the lipid bilayer, in which case the assay method can include ultraviolet light irradiation or addition of a singlet oxygen sensitizer to the bead-test agent mixture before observing whether a signal from the detectable label is altered. In other embodiments, the disruption of the lipid bilayer can be facilitated by adding an environmentally sensitive polymer that binds to the antibody, wherein the environmentally sensitive polymer changes conformation upon contacting the lipid bilayer and facilitates disruption of the lipid bilayer.

Another aspect of the invention is an assay for detecting an antigen, which comprises: (a) obtaining a lipid bilayer coated bead that displays a binding agent, wherein below the lipid bilayer the bead is coated with a detectable label; (b) linking a ligand to each antigen in a test sample to generate test antigen-ligand conjugates, wherein the ligand will bind to the binding agent displayed by the bead; (c) contacting the test antigen-ligand conjugates with an antibody that is specific for a selected antigen to form an antigen-antibody mixture; (d) adding the bead to the antigen-antibody mixture; and (e) observing whether a signal from the detectable label is altered. For example, at least one antigen can be a viral antigen, a cancer antigen, a bacterial antigen, a fungal antigen, an autoimmune antigen or a combination thereof. The binding agent can, for example, be biotin, streptavidin or an IgG receptor. As indicated above, in some embodiments, antibody-generated ozone or hydrogen peroxide can disrupt the lipid bilayer. Such an assay can further include a step of adding a competitive antigen to the test sample prior to linking the ligand to all antigens, wherein the competitive antigen is linked to an agent that inhibits antibody-generated ozone or hydrogen peroxide. In some embodiments, the agent that inhibits antibody-generated ozone or hydrogen peroxide is catalase.

Another aspect of the invention is a method of identifying a test agent that disrupts a lipid bilayer that comprises: (a) obtaining a suspension of microbeads in a solution of a molecule that can quench fluorescence from a dye in the microbeads; (b) contacting the suspension with a test agent; and (c) observing whether fluorescence from the microbeads is reduced.

Another aspect of the invention is a method of identifying a test agent that disrupts a lipid bilayer that comprises: (a) obtaining a suspension comprising microbeads wherein each microbead contains an ion-sensitive dye and is coated with a lipid bilayer, and wherein the suspension also comprises an ion that can modulate a detectable signal from the ion-sensitive dye; (b) contacting the suspension with a test agent; and (c) observing whether a signal from the microbeads is modulated.

Another aspect of the invention is a method of identifying a test agent that disrupts a lipid bilayer that comprises: (a) obtaining a suspension comprising microbeads wherein each microbead contains a pH-sensitive dye and is coated with a lipid bilayer, and wherein the suspension also comprises a solution at a pH that can modulate a detectable signal from the ion-sensitive dye; (b) contacting the suspension with a test agent; and (c) observing whether a signal from the microbeads is modulated.

Another aspect of the invention is a method of identifying a test agent that disrupts a lipid bilayer that comprises: (a) obtaining a suspension comprising microbeads wherein each microbead contains a self-quenching dye and is coated with a lipid bilayer; (b) contacting the suspension with a test agent; and (c) observing whether a signal from the microbeads increases. The method can further involve flow cytometry or fluorometry to detect beads with unquenched and quenched dye.

Another aspect of the invention is a method of detecting antigen binding to an antibody that comprises: (a) obtaining at least one microbead containing a detectable dye, wherein the microbead is coated with a lipid bilayer and one or lipids in the lipid bilayer are linked to an antigen; (b) contacting the at least one microbead with a test solution that may contain an antibody; and (c) detecting whether detectable dye is released from at least one microbead. This method can also include a step after (b) that involves irradiation with ultraviolet light to facilitate antibody-catalyzed generation of ozone and peroxides, thereby leading to disruption of the supported lipid bilayer.

Another aspect of the invention is a method of detecting antigen binding to an antibody that comprises: (a) obtaining a suspension of microbeads in a solution of a molecule that can quench fluorescence from a dye in the microbeads, wherein each of the microbeads is coated with a lipid bilayer and one or lipids in the lipid bilayer is linked to an antigen; (b) contacting the suspension with a test solution that may contain an antibody; and (c) observing whether fluorescence from the microbeads is reduced. This method can also include a step after (b) that involves irradiation with ultraviolet light to facilitate antibody-catalyzed generation of ozone and peroxides, thereby leading to disruption of the supported lipid bilayer.

Another aspect of the invention is a method of detecting antigen binding to an antibody that involves: (a) obtaining at least one microbead containing a detectable dye, wherein the microbead is coated with a lipid bilayer and one or lipids in the lipid bilayer are linked to a binding entity that can bind to an antigen; (b) contacting the antigen with a test solution that may contain an antibody to form test mixture; (c) contacting the suspension with the test mixture; and (d) observing whether fluorescence from the microbeads in the suspension is reduced. This method can also include a step after (c) that involves irradiation with ultraviolet light to facilitate antibody-catalyzed generation of ozone and peroxides, thereby leading to disruption of the supported lipid bilayer.

The antigen can be a viral antigen, a cancer antigen, a bacterial antigen, a fungal antigen, an autoimmune antigen or a combination thereof. In some embodiments, the antigen is an HIV antigen.

Another aspect of the invention is a kit comprising a suspension of beads or microbead of the invention, and solution of molecules that can modulate a signal from the dye contained within the microbeads. The solution can contain an ion that can modulate the signal from the dye. Alternatively, the solution is at a pH that can modulate the signal from the dye. In another embodiment, the solution contains a molecule that can quench the signal from the dye. In still another embodiment, the kit can include a solution of 9,10-anthraquinone-2,6-disulfonic acid and, separately, a suspension of the beads or microbeads of the invention.

DESCRIPTION OF THE FIGURES

FIG. 4A graphically illustrates dose-dependent release of fluorescent dye from a lipid bilayer coated microbead after introduction of different concentrations of alpha-toxin, a membrane-associated pore-forming protein from *Staphylococcus aureus*. The normalized fluorescence intensity (at 520 nm) of the supernatant is plotted versus time for EPC-coated, fluorescein filled porous beads when using different concentrations of α-toxin added. 10% Triton was added after 150 min. FIG. 4B illustrates the kinetics of disrupting a supported lipid bilayer by α-toxin as monitored by recording changes in fluorescence intensity every 2 minutes by flow cytometry. The lipid bilayer surrounded a porous bead that contains a pH-reactive molecule (fluorescein), and the pH outside the beads was adjusted to 11.0, whereas inside the beads the pH was 2.6. As illustrated, increasing amounts of c'-toxin increases the fluorescence emitted from within the beads.

FIG. 7A is an photomicrograph of a bead packed microchannel. Beads are retained by a weir like structure at the bottom of the microchannel. FIG. 7B is a schematic drawing of a microchannel showing the detection point for the phospholipid bilayer disruption in the microchannel. The detection point is irradiated with 488 nm Ar ion laser beam. FIG. 7C is a schematic drawing of the microfluidic channel packed with fluorescein-biotin beads and biotin encapsulated beads useful for performing membrane interaction studies and detecting the release of compounds. FIG. 7D is a schematic drawing of the microfluidic channel packed with membrane-coated PPE-beads for membrane interaction studies by fluorescence superquenching.

FIG. 10A illustrates a membrane stability study followed by membrane interaction with melittin. FIG. 10B shows fluorescence unquenching due to membrane removal by melittin followed by the fluorescence quenching due to PPE-AQS interaction.

FIG. 13A shows a single bead by fluorescence microscopy. FIG. 13B shows fluorescence intensity distribution histograms of MS-PPE obtained by flow cytometry. The y-axis represents the number of fluorescent events (counts), and the x-axis represents the mean channel fluorescence intensity. FIG. 13C graphically illustrates the fluorescence of MS-PPE normalized to the fluorescence of MS-PPE in absence of AQS as determined by flow cytometry. The error bars represent the standard deviation (SD) of the means of normalized histograms obtained for 4 replicates.

FIG. 17A shows a Stern-Volmer plot for quenching of PPE in solution, and MS-PPE by AQS as detected by fluorimetry. AQS was added to 200 µL of $9\times10^5$ fmoles PPE in solution or to $6.4\times10^6$ MS-PPE suspension (equivalent to $9\times10^5$ fmoles PPE in solution). FIG. 17B shows the fluorescence intensity distribution histograms of MS-PPE obtained by flow cytometry. The y-axis represents the number of fluorescent events (counts), and the x-axis represents the mean channel fluorescence intensity. FIG. 17C shows fluorescence normalized to that of sample +AQS. The error bars represent the standard deviation (SD) of the means of normalized histograms obtained for 4 replicates. $12.5\times10^5$ DMPG-coated MS-PPE beads in 200 µL PBS were analyzed by flow cytometry. 10 µM AQS was added, followed by treatment with TRITON X-100 detergent (TX-100), sMLT, or nMLT at final concentrations of 0.25% (w/v), 3.8 µM, and 1.6 µM, respectively.

FIG. 18A), and synthetic MLT (sMLT; FIG. 18B). Fluorescence intensity was normalized to that without MLT as determined by flow cytometry. The error bars represent the standard deviation (SD) of the means of normalized histograms obtained for 3 replicates.

FIG. 20A shows a schematic of the microfluidic channel used. Channel dimensions were typically 2 cm, 250 µm, 60-70 µm in length, breadth and depth respectively, and the length of the packed beads segment was about 5 mm. The bead segment was irradiated with 488 nm laser excitation, and emission is detected at 520 nm. The inlet of the column was connected to a buffer reservoir, while the outlet was connected to a vacuum source. FIG. 20B illustrates the effect of adding AQS and nMLT on MS-PPE. Concentrations of injected AQS and nMLT were 120 µM and 309 µM, respectively. AQS+nMLT represents injecting a mix of equal volumes of AQS and nMLT. Fluorescence intensity is measured in arbitrary units. The arrows indicate injections. The time delay between the point of sample injection and the packed beads was ~38 min.

FIG. 22A is a graph showing release of dye from porous particles (containing dye inside) where the particles are coated with a cholesterol (10%, molar ratio) containing lipid membrane. As increasing amounts of streptolysin-O are added (solid square symbols represent lower concentration than solid ovals), more dye is released. However, even at low concentrations the release is greater than observed for control (Con) without streptolysin-O. The release is also somewhat dependent on temperature, with more dye being released at higher temperatures (37° C.) than at lower temperatures (25° C.). FIG. 22B illustrates how streptolysin-O can disrupt cholesterol-containing lipid bilayer membranes, leading to release of materials (e.g., drugs or antibiotics) enclosed within the membrane. Streptolysin-O is an anti-microbial protein that preferably binds to cholesterol and can disrupt cholesterol-containing membranes.

FIG. 31 illustrates a delivery system for drugs that employs neurotoxin receptors immobilized onto lipid bilayer-supported beads (diamond-shaped symbols). Most neurotoxins (e.g., tetanus toxin) bind to specific receptors (e.g. gangliosides) in lipid membranes. Therapeutic agents are encapsulated within the lipid bilayer-supported beads that have neurotoxin receptors immobilized thereon. When neurotoxins are present, the receptors bind to the neurotoxins and this bonding promotes release the therapeutic agents encapsulated within the lipid bilayer-supported beads. Thus, therapeutic agents can be released in a site-specific manner to neuronal sites that may suffer from the presence of neurotoxins.

DETAILED DESCRIPTION OF THE INVENTION

Figure 1:
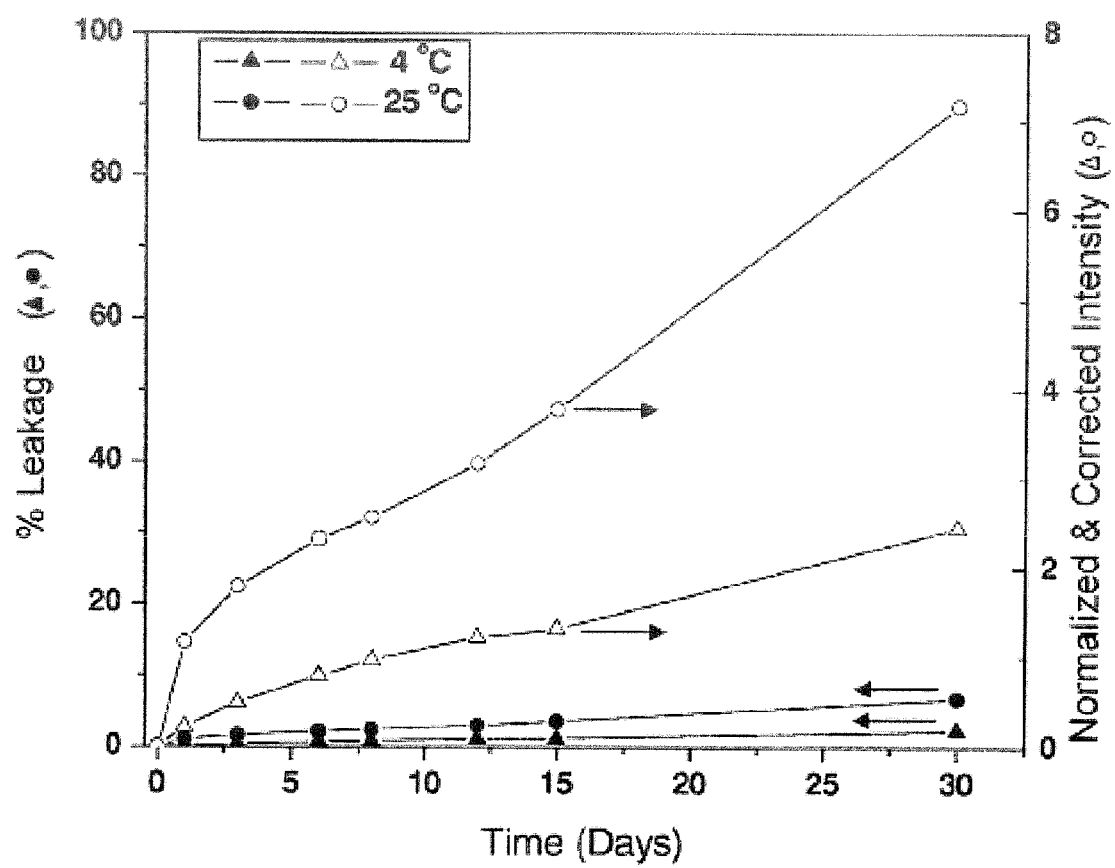
FIG. 1 illustrates the percent leakage (closed symbols) of fluorescent dye from microbeads coated with egg phosphatidyl choline (EPC) over time at different temperatures. The normalized and corrected intensity of the supernatant fluorescence intensity (open symbols) is also shown. Triangular symbols show the leakage and supernatant fluorescence at 4° C. and the circular symbols show the leakage and supernatant fluorescence when beads are stored at 25° C.

The invention is directed to lipid bilayers supported on either porous or non-porous beads that can be used as delivery systems for therapeutic agents or as detection systems to identify specific substance in test samples or assess what effects test agents have on the lipid bilayers. Porous beads may be used as encapsulating agents for molecules such as therapeutic agents or detectable labels. Non-porous beads may also be used by coating the non-porous beads with fluorescent dyes prior to formation of the lipid bilayer. For example, highly sensitive polymeric dyes whose fluorescence can be quenched by quenching agents in the solution surrounding the beads can be used in sensitive superquenching assays of lipid bilayer membrane stability and function. Assays for lipid bilayer stability can also involve bead suspension, flow cytometric, and microfluidic channels assays.

Particles and Beads

The invention contemplates compositions and methods that include lipid bilayer coated or supported beads and/or particles. The skilled article will realize that the invention is not limited to spherical beads and any shaped bead or particle may be used. Thus, the beads and/or particles can be spherical but can also be other shapes, such as ovals, cubes, closed cylinders and irregular shapes. The terms bead and particle are used interchangeably herein to signify that any shaped bead or particle can be used in the invention.

The beads and/or particles are generally small enough to be administered to be suspended in liquids and/or to be administered into the bloodstream of a patient. The beads and particles can be small. Beads and particles as small as 75 Angstroms have been used successfully. Thus, for example, the beads and particles can be at least about 30 Angstroms in diameter or at least about 40 Angstroms in diameter or at least about 50 Angstroms in diameter. The upper size for beads and/or particles can depend upon the application or purpose of the supported lipid bilayer composition generated from the beads and particles. Thus, for example, if the composition is to be used for therapeutic purposes and will be administered intravenously, beads and/or particles of an appropriate size for negotiating blood vessels are used. Such a blood vessel appropriate size can be about 20 Angstroms to about 20 microns, or about 30 Angstroms to about 10 microns. Moreover, in some embodiments, the beads and particles employed can have a range of sizes. For example, the beads and particles of the invention can be about 40 Angstroms to 100 microns in diameter. In some embodiments, the beads and particles of the invention can be about 1 micrometer to about 50 micrometers in diameter. In other embodiments, the beads and/or particles are about 50 Angstroms to about 50 microns in diameter. In other embodiments, the beads and/or particles are about 70 Angstroms to about 30 microns in diameter. In other embodiments, the beads and/or particles are about 75 Angstroms to about 20 microns in diameter.

Beads and/or particles can be porous or non-porous. The selection of whether to use porous or non-porous beads can be based on the application or purpose for which the beads and/or particles will be used. Thus, if the beads and/or particles are used to generate delivery systems, porous beads/particles are used to permit loading of therapeutic or other desirable agents into the beads. However, if the beads are used for detection of substances that can modulate lipid bilayer structure or function, or if the beads are used for lipid bilayer structure and function studies, non-porous beads can be used so long as the beads/particles can be coated with a detectable label or substance that can provides a signal when the lipid bilayer is disrupted.

The beads and/or particles can be biodegradable beads, non-biodegradable beads, silica beads, magnetic beads, latex beads, glass beads, quartz beads, metal beads, gold beads, mica beads, plastic beads, ceramic beads, or combinations thereof.

In addition, the beads and/or particles can be made from biodegradable materials such as starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. However, other suitable substances for forming the particles exist and can be used. In some embodiments, the particles comprise a cross-linked starch, for example, cross-linked potato starch. Particles made from starch are completely biodegradable in the body, typically by serum amylase, a naturally occurring enzyme found in the body. European patent application nos. 0184899 and 0186947, which are incorporated in their entirety herein by reference, describe several examples of suitable polymeric or polymerized carbohydrate or polymerized sugar alcohol or derivative suitable for use in the present invention.

Non-biodegradable beads and particles can also be used. For example, Hydron (polymethylmethacrylate available commercially as "Hydron NCC" non-adhesive cell culture media, from Hydro Med Sciences, 8 Cedar Brook Drive, Cranbury, N.J. 08512333), polyester, polycarbonate, polysulfone, polyvinyl chloride, polyethylene, polypropylene, poly (N-vinyl pyrrolidone), poly(methyl methacrylate), poly(vinyl alcohol), poly(acrylic acid), polyacrylamide, poly (ethylene-co-vinyl acetate), poly(methacrylic acid), mixtures thereof and combinations thereof may be used.

The beads and particles are used to hold therapeutic agents and to support and stabilize the lipid bilayers with which they are coated.

Lipid Bilayers

The invention is directed to compositions containing supported lipid bilayers and methods of using those supported lipid bilayers.

Lipid bilayers for use in the compositions and methods of the present invention include those composed primarily of vesicle-forming lipids. Vesicle-forming lipids can form spontaneously into bilayer vesicles in water. In general, as is known to the skilled artisan, any lipid can be used to form lipid bilayers if the lipid has a hydrophobic moiety that can be in contact with the interior, hydrophobic region of the bilayer membrane, and a hydrophilic head group moiety oriented toward the exterior, polar surface of the bilayer membrane. For example, phospholipids are often used to make lipid bilayers and can be used in the present supported lipid bilayers.

In some embodiments, the lipid bilayer can be made from saturated or unsaturated fatty acids ranging from 3 to 28 carbons in chain length and with 0 to 6 unsaturated bonds. The lipids employed can, for example, have two hydrocarbon chains, typically acyl chains, and a head group, either polar or nonpolar. There are a variety of synthetic and naturally-occurring lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods.

Other lipids can also be incorporated into the lipid bilayers whether they are capable of forming a lipid bilayer on their own or not. For example, non-phospholipids, neutral lipids, glycolipids, cholesterol, sterols, steroids, and the like can be included in the lipid bilayers so long as they do not significantly disrupt the stability of the lipid bilayer.

Phospholipids useful in the supported lipid bilayers of the invention include native and/or synthetic phospholipids. The phospholipid component of the lipid bilayer includes one or more phospholipids, such as phosphatidylcholine (PC), phosphatidyl ethanolamine (PE), phosphatidylinositol (PI), phosphatidyl glycerol (PG), phosphatidic acid (PA), phosphatidyl serine (PS), and sphingomyelin (SM). The fatty acyl chains in the phospholipids are generally at least about 7 carbon atoms in length, typically 12-20 carbons in length, and may be entirely saturated or partially unsaturated.

Thus, exemplary phospholipids include phosphatidylcholines, such as dipalmitoyl phosphatidylcholine (DPPC), dilauryl phosphatidylcholine (DLPC) C12:0, dimyristoyl phosphatidylcholine (DMPC) C14:0, distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2)), dipalmitoyl phosphatidylethanolamine, dioleoylphosphatidylethanolamine (DOPE), dioleoyl phosphatidylglycerol (DOPG), palmitoyloleoyl phosphatidylglycerol (POPG), distearoylphosphatidylserine (DSPS) soybean lecithin, egg yolk lecithin, sphingomyelin, phosphatidylserines, phosphatidylglycerols, phosphatidyl inositols, diphosphatidyl glycerol, phosphatidylethanolamine, and phosphatidic acids.

Other lipids that can be used include, 1,2-diacyl-sn-glycero-3-[phospho-rac-(1-glycerol)], 1,2-diacyl-sn-glycero-3-[phospho-L-serine], 1,2 diacyl-sn-glycero-3-phosphocholine, 1,2-diacyl-sn-glycero-3-phosphate, 1,2-diacyl-sn-glycero-3-phosphoethanolamine where the diacyl groups may be symmetrical, asymmetrical and contain either saturated or unsaturated fatty acids of various types ranging from 3 to 28 carbons in chain length and with up to 6 unsaturated bonds.

The lipid bilayer can also include egg phosphatidyl choline (EPC), 1,2-dimyristoyl-sn-glycero-3-phosphocholine (DMPC), 1,2-dimyristoyl-sn-glycero-3-[phospho-rac-(1-glycerol)], a salt thereof or a combination thereof.

In some embodiments, anionic lipids are used. Such anionic lipids are useful particularly when the bead or particle tends to have positively charged moieties, either because of the material used for the bead/particle or because the bead/particle has been coated with a cationic substance (e.g., a cationic polymer that can emit a detectable signal). Examples of anionic lipids include, for example, the phosphatidic acid (PA), phosphatidylserine (PS), and phosphatidylglycerol (PG), phosphatidylcholine (PC), 1,2-dimyristoyl-sn-glycero-3-[phospho-rac-(1-glycerol) (DMPG).

Cationic lipids are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. The head group of the lipid can carry a positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3[N—(N',N'-dimethylaminoethane) carbamoly]cholesterol (DC-Chol); and dimethyldioctadecylammonium (DDAB). The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

In another embodiment, the lipids are selected to achieve a specified degree of fluidity or rigidity, to control the stability of the supported lipid bilayer and/or to control the rate of release of the entrapped agent within the supported lipid bilayer. Lipid bilayers having a more rigid structure, or a liquid crystalline bilayer, are achieved by incorporation of a relatively rigid lipid, for example, a lipid having a relatively high phase transition temperature. Such a high phase transition temperature is generally above room temperature or above body temperature and can be as high as up to about 80° C. Saturated lipids can contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, for example, at or below room temperature, or at or below body temperature.

Vesicle-forming lipids having a main phase transition temperatures from approximately 2° C. to 80° C. are suitable for use as the primary lipids in the present supported lipid bilayers. In some embodiments of the invention, a vesicle-forming lipid having a main phase transition temperature of greater than about 20° C. to 37° C. are used. In other embodiments, lipids are selected so the main phase transition temperature is above about 37° C. is used as the primary lipid component of the liposomes. In other embodiments, lipids are selected so the supported lipid bilayer has a phase transition temperature between about 37° C. to 70° C.

By way of example, the lipid distearoyl phosphatidylcholine (DSPC) has a main phase transition temperature of 55.1° C. and the lipid hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NIST Standard Reference Database 34).

Figure 22:
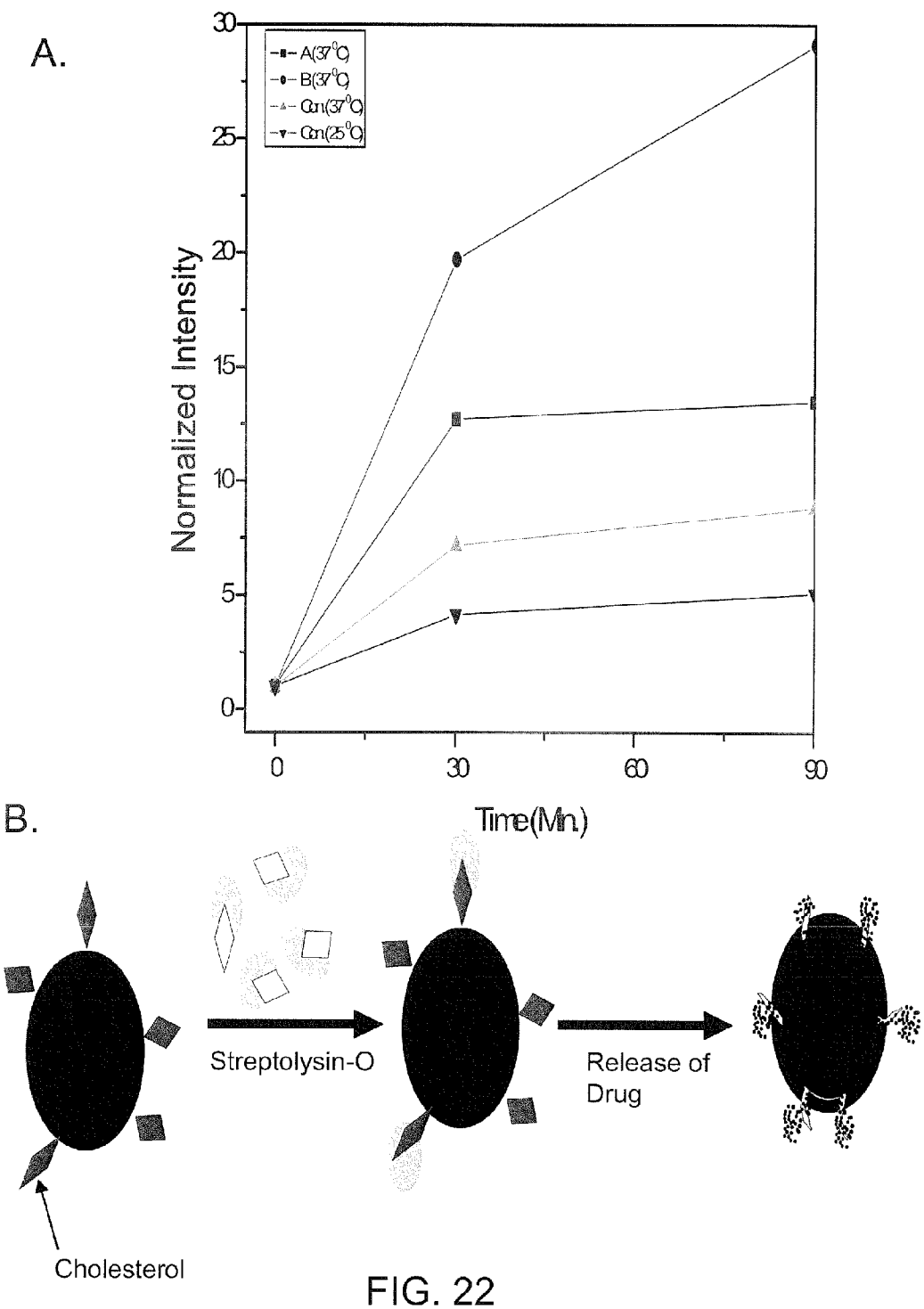
FIGS. 22A-B illustrate one aspect of the invention—drug and/or dye release from the present lipid-coated particles.

In some embodiments, lipids are selected so that no substantial amount of the detectable label leaks from the bead unless the bead is exposed to temperatures above about 30° C. In other embodiments, lipids are selected so that no substantial amount of the detectable dye leaks from the bead unless the bead is exposed to temperatures above about 25° C. FIG. 22 further illustrates the effect of temperature on dye and drug release.

The above-described lipids and phospholipids can be obtained commercially, or prepared according to published methods that are generally known in the art.

Manufacturing Methods

Supported lipid bilayers are readily made by forming lipid vesicles containing the selected lipids in a suitable aqueous medium, adding the selected beads and/or particles and vigorously mixing the lipid vesicles with the beads/particles.

The selected lipids may be stored or dissolved in an organic solvent to facilitate handling and accurate dispensing of desired amounts of a selected lipid. After the desired composition of lipids is generated, any organic solvent used to dissolve the lipids (or mixture of lipids) can be removed by available procedures such as by drying the lipids under a stream of inert gas (e.g., nitrogen) and/or use of a vacuum. The dry lipids can be hydrated by addition of an aqueous solution or buffer followed by the vigorous mixing (e.g., sonication) for a time sufficient not only to hydrate the lipids in the aqueous solution but also to form lipid bilayer vesicles (e.g., about 10-60 min.). In general, excessive heating is avoided and the hydration/vesicle forming procedure is performed at a temperature that is a few degrees (e.g., two degrees) above the transition temperature of the lipid components of the vesicle. Room temperature is a suitable temperature for hydration and vesicle formation of some lipids, for example, this temperature is generally suitable when egg phosphatidyl choline and/or shorter chain lipids are used. However, the temperature at which this procedure is performed should be adjusted to accommodate the type of lipid utilized with consideration for its glass transition temperature.

After formation of lipid vesicles, lipid bilayers are formed around beads/particles by vigorous mixing of the beads/particles with a suspension of lipid vesicles for a time sufficient to mix the beads/particles with the lipids (e.g., about 5 to 60 minutes, or in some embodiments about 15 to 45 minutes). The bead/particle suspension is then incubated without vortexing for a time sufficient to coat the beads/particles with lipid bilayers (about 2 to 20 minutes, or in some embodiments about 3 to 10 minutes). Excess lipids and other materials can be removed by rinsing or washing the lipid coated beads in a selected aqueous medium (e.g. a suitable buffer). Such rinsing or washing can be performed by repeated suspension of the lipid bilayer coated beads/particles in a selected aqueous medium, centrifugation of the lipid bilayer coated beads/particles, and decanting the aqueous supernatant.

Encapsulated Agents

The supported lipid bilayers provided by the invention represent a new form of vehicle for a broad range of applications, including therapeutic, pharmaceutical, agricultural, analytical and related applications. Thus, a large variety of agents can be incorporated into the lipid bilayer coated beads. For example, the supported lipid bilayers can be used to encapsulate any material chosen by one of skill in the art for targeted, slow, sustained or timed release. In other embodiments, the supported lipid bilayers can be used to encapsulate any detectable label chosen by one of skill in the art that is useful for detection and analysis of factors in the environment. The supported lipid bilayers can be used in any environment selected by one of skill in the art, for example, for therapy, for wound treatment, for immunoassays, for analytical assays and for agricultural formulations.

Materials encapsulated within the supported lipid bilayers of the invention include, for example, a therapeutic agent, a detectable label, a pharmaceutical, an antiseptic reagent, a chemical compound, a peptide, a protein, an antibody, an oligonucleotide, a nucleic acid, a lipid, a carbohydrate, a fertilizer, a herbicide, an insecticide, or any other molecule chosen by one of skill in the art.

In some embodiments, the supported lipid bilayers of the invention encapsulate therapeutic agents useful for treatment of inflammation, viral infection, bacterial infection, autoimmune diseases, heart disease, cancer and other diseases and conditions.

In other embodiments, the supported lipid bilayers of the invention encapsulate detectable labels to form reagents useful for detection of diseases and conditions such as inflammation, viral infection, bacterial infection, autoimmune diseases, heart disease, cancer and the like.

When release of a therapeutic agent is desired, a porous bead or particle is used and the bead or particle is mixed with the therapeutic agent prior to coating the beads or particles with lipid. The concentration of therapeutic agent is adjusted so that the bead becomes saturated with an appropriate amount of therapeutic agent. After incorporation of therapeutic agent and coating with lipid, the concentration of therapeutic agent in an encapsulation batch by available procedures. For example, an aliquot of the batch can be tested by removing the lipid bilayer, using a detergent such as TRITON X-100 detergent, and examining how much therapeutic agent is present. Appropriate dosages of the encapsulated agents can thus be prepared.

Targeted Release from Supported Lipid Bilayers

The agents incorporated into the lipid bilayer coated beads/particles of the invention can be targeted for release to specific tissues or sites in the body by incorporating "targeting agents." A "targeting agent" is a molecule that can bind or be bound by a tissue-specific, condition-specific or disease-specific factor. Thus, for example, an antibody can be a targeting agent if the antibody specifically recognizes and binds to a viral antigen. Similarly, an antigen can be a targeting agent if the antigen is specifically recognized by or is bound by an antibody that gives rise to an inflammatory response. Examples of targeting agents include antigens, antibodies, receptors, ligands and the like.

In one embodiment, the targeting agent is a receptor. The receptor is selected to bind to any ligand of interest to one of skill in the art. Thus, for example, the receptor can recognize any ligand that may be associated with a disease or condition that one of skill in the art chooses to treat. Examples of receptors that can be targeting agents include neurotoxin receptors, receptors recognized by viruses, receptors recognized by cytokines, receptors recognized by hormones, and the like.

In another embodiment, the targeting agent is an antibody. The antibody is selected to bind to any antigen of interest to one of skill in the art. Thus, the antibody can recognize or bind to antigens such as viral antigens, bacterial antigens, fungal antigens, cancer-associated antigens, and other antigens associated with specific diseases and conditions. However, antibodies can produce ozone and hydrogen peroxide (Lerner & Eschenmoser, Ozone in biology. Proc. Natl. Acad. Science 100(6): 3013-3015 (2003)), which are disruptive of lipid bilayers. Hence, when antibodies are attached to the encapsulated supported lipid bilayers of the invention, the antibody may produce ozone and/or hydrogen peroxide, which disrupts the lipid bilayer prior to binding with the target antigen at the disease site.

Therefore, in some embodiments, the targeting agent is an antigen rather than an antibody. Any antigen may be used. In some embodiments, the antigen is selected because it is recognized and bound by antibodies that are involved in undesirable immune responses. For example, antibodies that are involved in undesirable immune responses include antibodies involved in inflammation and other inflammatory disorders and conditions. Inflammation is defined as the reaction of vascularized living tissue to injury. As such, inflammation is a fundamental, stereotyped complex of cytologic and chemical reactions of affected blood vessels and adjacent tissues in response to an injury or abnormal stimulation caused by a physical, chemical or biological agent. Inflammation usually leads to the accumulation of fluid and blood cells at the site of injury, and is usually a healing process. However, inflammation sometimes causes harm, usually through a dysfunction of the normal progress of inflammation.

Inflammatory diseases are those pertaining to, characterized by, causing, resulting from, or becoming affected by inflammation. Examples of inflammatory diseases or disorders include, without limitation, asthma, bronchitis, lung inflammation, osteoarthritis, juvenile arthritis, rheumatoid arthritis, spondylo arthopathies, gouty arthritis, chronic granulomatous diseases such as tuberculosis, leprosy, sarcoidosis, and silicosis, nephritis, amyloidosis, ankylosing spondylitis, chronic bronchitis, scleroderma, systemic lupus erythematosus, polymyositis, appendicitis, inflammatory bowel disease, Crohn's disease, gastritis, irritable bowel syndrome, ulcerative colitis and for the prevention of colorectal cancer, Sjorgen's syndrome, Reiter's syndrome, psoriasis, pelvic inflammatory disease, orbital inflammatory disease, thrombotic disease, menstrual cramps, tendinitis, bursitis, psoriasis, eczema, burns, dermatitis and inappropriate allergic responses to environmental stimuli such as poison ivy, pollen, insect stings and certain foods, including atopic dermatitis and contact dermatitis. The methods of the invention are also useful for treating inflammation in vascular diseases, migraine headaches, periarteritis nodosa, thyroiditis, aplastic anemia, Hodgkin's disease, scleroderma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like.

In other embodiments, an antigen is selected as a targeting agent because it is bound by antibodies produced by a mammal in response to diseases such as viral infections, bacterial infections, cancer and the like. Thus, the antigen can be a viral antigen, a bacterial antigen or a cancer antigen.

These and other related conditions and diseases can be treated with the present compositions and methods. Moreover, the present compositions and methods can also be used to treat side effects of the conditions and diseases listed above, for example, the present compositions can be used an analgesic in the treatment of pain and headaches, or as an antipyretic for the treatment of fever.

Targeting agents are bound to the beads/particles or to the lipids that are used to form the lipid bilayer. Targeting agents can be directly linked to a bead/particle or a lipid molecule. Alternatively, the targeting agents can be attached to a linker that is attached to the bead/particle or the lipid.

Thus, the invention includes particles or beads that have targeting agents and therapeutic agents, which can be formulated into pharmaceutical compositions for administration to an animal.

Detection Systems

The invention is also directed to detection systems that can be used for detection of molecules of interest or for analysis of the effects of molecules on lipid bilayer structure and function. Thus, in some embodiments, the supported lipid bilayers of the invention are used for detection of molecules responsible for, or associated with, disease, pollution, or other phenomena of interest to the skilled artisan. In other embodiments, the supported lipid bilayers of the invention are used for analysis of membrane structure and/or function. In still other embodiments, the supported lipid bilayers of the invention are used for detection of whether and how a molecule can affect membrane structure and function. In further embodiments, the supported lipid bilayers are used for toxicity screening, for example, to ascertain whether a molecule can interact with or disrupt a lipid bilayer.

The detection systems of the invention include supported lipid bilayers on beads or particles that can respond to environmental factors and stimuli by emitting a detectable signal. Such a detectable signal can be produced by a detectable label that is incorporated into or onto the beads or particles and that is shielded in some respect from emitting a signal when the lipid bilayer is intact. Thus, for example, the bead can be impregnated with a detectable dye or label prior to coating with the lipid bilayer, and when the lipid bilayer is disrupted or stripped from the bead, the dye or label leaks out of the bead. In another embodiment, the bead is coated with polymeric dye that emits a signal when coated with the lipid membrane, but when the membrane is disrupted the signal is quenched, either because the dye is environmentally sensitive or because a quenching molecule is present in the solution surrounding the lipid coated (or uncoated) bead. Many variations of these two examples can be used and all are contemplated by the invention.

In some embodiments, the present lipid bilayer coated beads are used with a "detector molecule." In other embodiments, no such detector molecule is employed. A "detector molecule" is a molecule that binds to or responds to specific factors and stimuli in the environment, thereby lending specificity to the detection system. For example, the detector molecule may specifically bind to a molecule that disrupts the lipid bilayer, such that a detectable dye is released from the lipid coated particles. The detector molecule generally does not emit a signal. Instead, the detector molecule binds or interacts with a factor or stimulus in the environment, and that factor or stimulus alters the lipid bilayer so that a signal is emitted from a dye or label contained within the lipid coated beads.

Such detector molecules can be any molecule that is recognized, bound or structurally altered by a factor or a stimulus in the environment. Examples of detector molecules include antigens, antibodies, ligands, enzymes, receptors, specific binding agents, non-specific binding agents and the like. Examples of binding agents (other than antibodies and antigens) include biotin, streptavidin and IgG receptors (e.g., FcγR). For example, FcγRIIb (CD32) is a low affinity receptor for monomeric IgG, but FcγRIIb binds with high avidity to aggregated IgG such as those formed in immune complexes.

The detector molecules can be covalently or non-covalently attached either to the beads or to the lipids of the lipid bilayer. In some embodiments, the detector molecules are attached via a linker or spacer. Such a linker or spacer can help to optimally position the detector molecules for interaction with the environment or factors in the environment.

The detection systems of the invention can be used in numerous assays. Such assays can be immunoassays, ligand-receptor assays, or any other assay involving an environmental change or the juxtapositioning of a factor that can alter a lipid bilayer. In some embodiments, the presence of an analyte is directly detected by the present detector systems, for example, in a non-competitive immunoassay. In other embodiments, the assay is a competitive immunoassay. A competitive immunoassay refers to an immunoassay that is designed so that the analyte to be measured and a labeled analyte compete for a limited number of mutually exclusive binding sites. In these types of immunoassays the abundance of the analyte is inversely related to the binding of the labeled analyte. Examples of the types of detection assays that can be used with the present detection systems are given below.

Many of the assays contemplated by the present invention are based on disruption of the lipid bilayer. These assays utilize detectable labels that are incorporated into porous beads or coated onto non-porous beads. In another embodiment, mesoporous beads can be used where the detectable label (e.g., a fluorescent dye) is entrapped inside the porous beads. When the lipid bilayer is disrupted, the detectable label is released from porous beads into the environment, becomes apparent within mesoporous beads that entrap the detectable label, or the label coated on the non-porous beads undergoes a visible change in its signal.

Some studies described herein indicate that larger signal changes can be achieved when using a detection label-coated non-porous bead in a solution of a quenching substance, than when using a porous bead that can leak a diffusible dye. For example, the cationic polyelectrolyte poly(p-phenylene-ethynylene) derivative (PPE; from QTL) is a fluorescent molecule that emits a strong signal at 520 nm when coated with lipid bilayers and irradiated with light at 488 nm. However, the quencher 9,10-anthraquinone-2,6-disulfonic acid (AQS) will quench the PPE fluorescent signal, but only when the lipid bilayer is disrupted so AQS can interact with the PPE. Thus, the invention contemplates lipid bilayer disruption assays that involve observing whether a fluorescent signal from lipid-coated beads is extinguished or diminished by a test agent when the lipid coated beads are in solution with a quenching molecule that can quench the fluorescent signal from the lipid coated beads.

Thus, one aspect of the invention is a sensitive assay for membrane biointeractions based on fluorescence superquenching using beads coated with a superquenchable polymer. Because the superquenchable polymer emits the signal from the lipid coated beads and, in some embodiments does not leak from the beads even when the lipid bilayer is disrupted, the presence or absence of lipid bilayer disruption can be detected by flow cytometry, or simply by observing the fluorescence intensity of the bead suspension.

Using the superquenching of fluorescent polymer coated lipid bilayer beads, total disruption of the bilayer was observed with some membrane-lytic peptides (e.g. streptolysin O's interaction with cholesterol-containing lipids, and mellitin's interaction with anionic lipids) or with lipolytic enzymes such as phospholipase $A_2$. On the other hand, some test agents may only lead to gaps or smaller interruptions of the lipid bilayer, for example, as a result of insertion of a channel- or pore-forming proteins such as gramicidin and hemolysin. In either case, the result is either complete or partial superquenching of the fluorescent polymer. In general, non-porous beads are used for such quenching assays because the quenchable polymer is preferably coated onto the beads and is not impregnated into the beads.

Assays based on disruption of lipid bilayers supported on porous beads can also utilize an encapsulated detectable label that is not adsorbed or covalently attached to the beads. Upon disruption of the lipid bilayer, the label is released from the bead and can be detected in the solution surrounding the lipid-coated beads. In these instances, the assay can be performed by suspending the lipid bilayer beads in solution, adding the test agent and periodically removing an aliquot of the suspension for analysis. The analysis can involve centrifugation of the aliquot and observation of whether dye is present in the supernatant. Alternatively, flow cytometry could be used for analysis of suspended beads, or the lipid-coated beads can be placed into a column (or microcolumn) and the test agent can be applied to the column. If dye is released and washed through with the eluent, then membrane disruption has occurred.

The present lipid bilayer coated beads for use in lipid bilayer disruption assays can have a covalently or non-covalently attached "detector molecule" as described above. These detector molecules may specifically bind to a molecule that disrupts the lipid bilayer, such that a detectable dye is released from the lipid coated particles or the signal from a quenchable coating on the beads is quenched by a quencher present in the solution surrounding the beads. The detector molecule can be an antigen, antibody, ligand, enzyme, receptor, ligand, specific binding agent, non-specific binding agent and the like. FIGS. 22-31 illustrate specific examples of detector molecules, including cholesterol (recognized by streptolysin-O, which can lyse membranes), antigens, antibodies, biotin, streptavidin, IgG receptors (e.g., FcγR, which can bind IgG, especially aggregated IgG) and combinations thereof.

One type of molecule that can be a detector molecule or can bind to a detector molecule is an antibody. Antibodies, regardless of their source or antigenic specificity, catalyze the generation of ozone and peroxide by a water oxidation pathway (Lerner & Eschenmoser., *Ozone in biology*. Proc. Natl. Acad. Sci. 100(6): 3013-3015 (2003)). The only requirement for antibodies to mediate this reaction is a source of singlet molecular oxygen, which can be provided by near ultraviolet (UV) irradiation, or by addition of substances that generate singlet oxygen (e.g., hematoporphyrin or methelyne blue). The formed ozone, and to a lower extent hydrogen peroxide lead to peroxidation of lipid bilayers and formation of free radicals, resulting in disruption of the lipid bilayer and leakage of the contents of the beads or some other change in signal from the beads (e.g. quenching of a signal from the beads if a quencher is present in the solution surrounding the beads).

Figure 23:
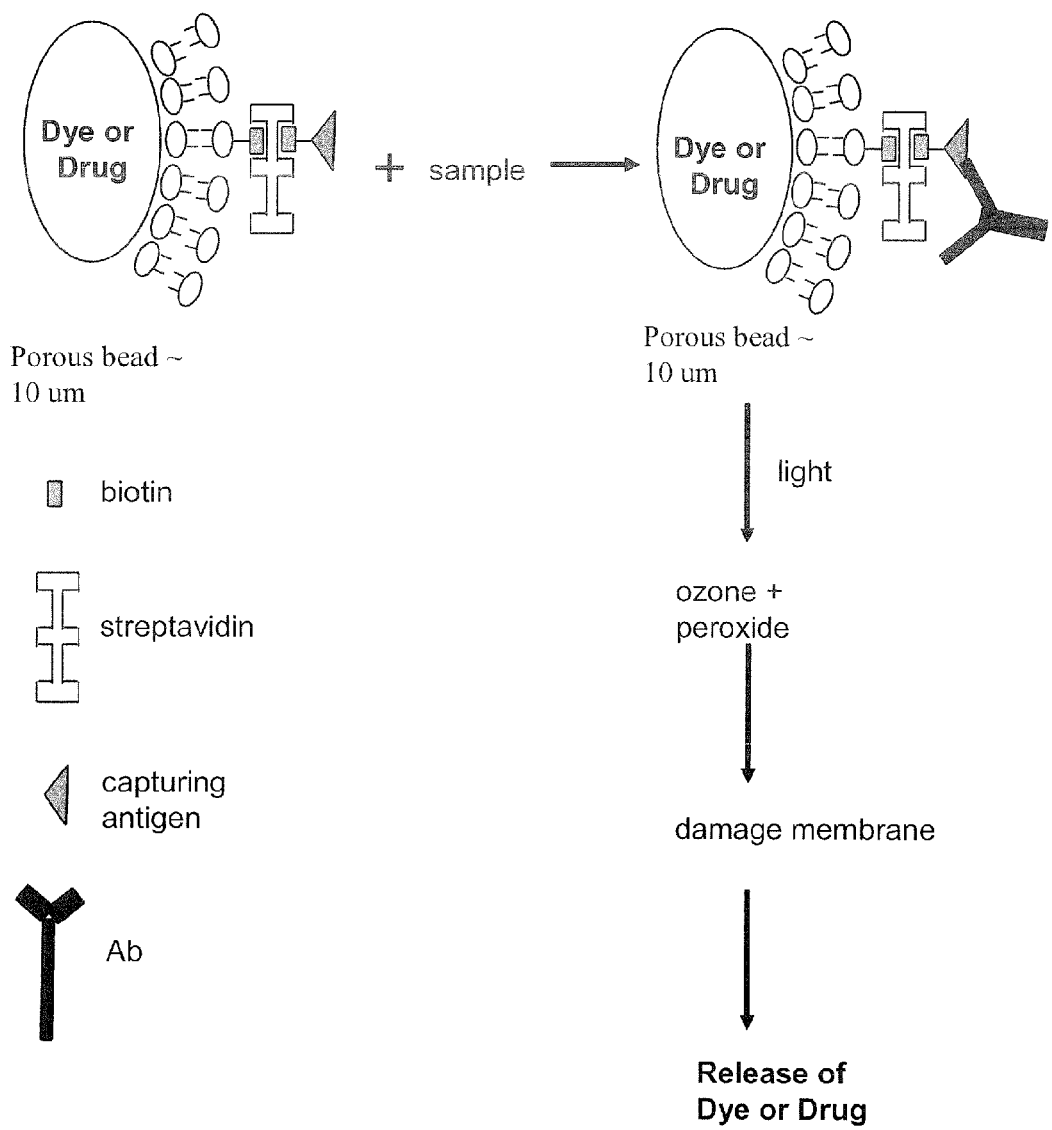
FIG. 23 illustrates an immunoassay or delivery system of the invention. An antigen immobilized on the lipid bilayer-supported beads. The antigens incorporated into the supported lipid bilayer can be any antigen selected by one skilled in the art, for example, HIV antigens, and antigens associated with autoimmune diseases. If an antibody is present, for example, in an in vitro test sample or at the site of inflammation in vivo, the antibody will bind to the antigen. The assay mixture can be exposed to ultraviolet light to facilitate antibody-generated generation of ozone or hydrogen peroxide that can disrupt the lipid bilayer, thereby releasing the materials encapsulated within the lipid-bilayer supported beads (e.g. a dye or a drug). Therefore, drugs can be delivered in a site-specific manner, for example, to sites of inflammation where antibodies specific to the immobilized antigen are present.
Figure 24:
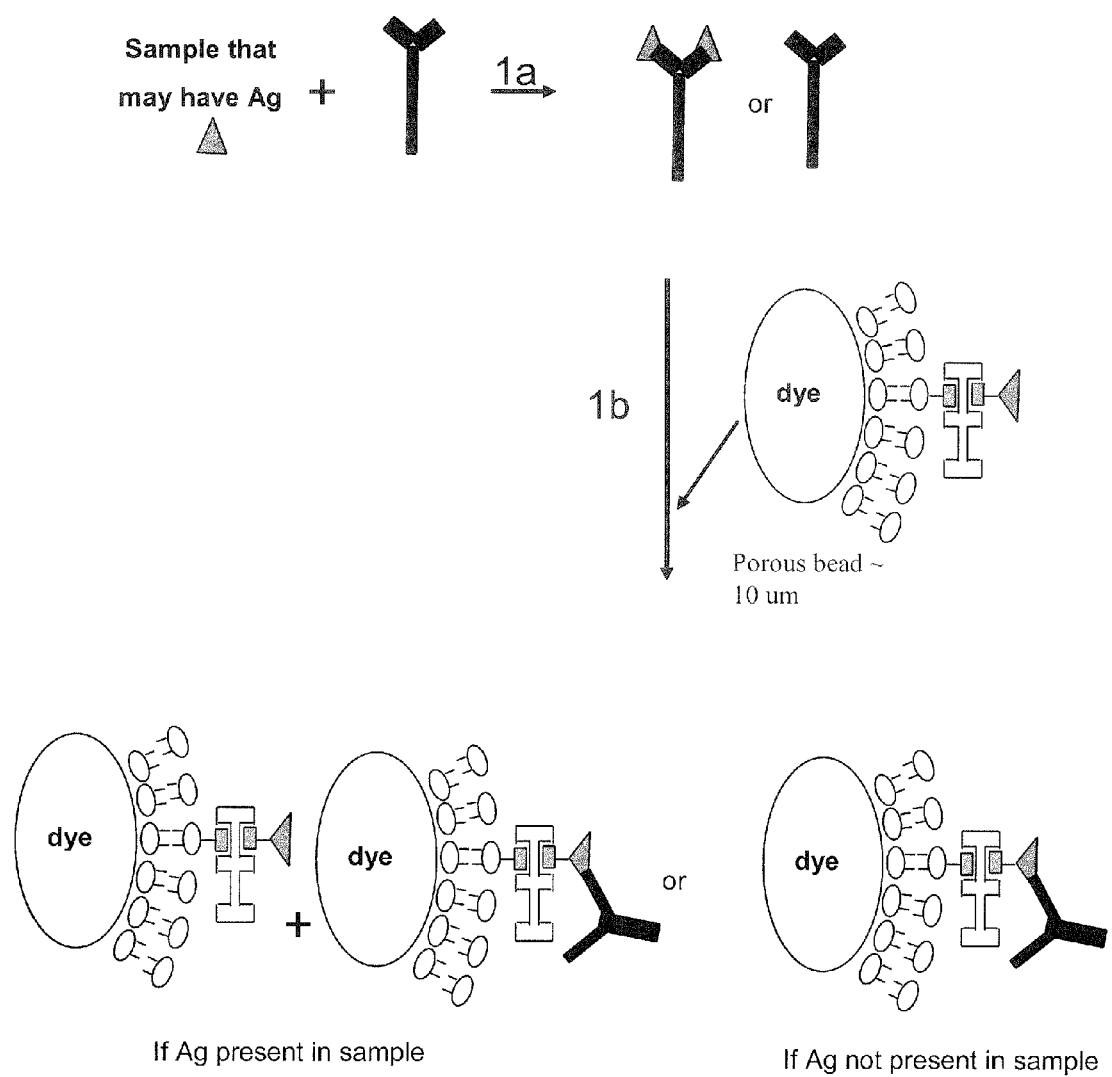
FIG. 24 illustrates a competitive assay for detection of antigen in samples by competition for antibody binding between the free antigen in the sample and an immobilized antigen. In step 1a, a sample that may contain an antigen of interest is mixed with known amount of antibody. If the sample has antigen, an antibody-antigen complex forms that reduces the amount of free antibody available. The amount of free antibody is detected by addition a supported lipid bilayer linked to an antigen via streptavidin-biotin (step 1b) (see FIG. 23). The assay mixture can be exposed to ultraviolet light to facilitate antibody-catalyzed generation of ozone or hydrogen peroxide. The ozone/hydrogen peroxide disrupts the lipid bilayer, permitting release of the dye that within the lipid bilayer coated beads. Note that steps 1a and 1b can be done simultaneously or sequentially. If done sequentially, the outcome is either that the beads will capture the antibody or will not, and if no antibody is captured, no fluorescence will be detected outside of the beads.

In some embodiments, biotin and/or streptavidin are used with the present lipid bilayer coated beads. The biotin and/or streptavidin can be used either as a spacer to which a detector molecule can be attached, or as a detector molecule that can capture analytes. For example, as shown in FIGS. 23 and 24, biotin and/or streptavidin are used as spacers to which an antigen is attached. In FIG. 23, the biotin attached to the lipid is complexed with a streptavidin-linked antigen, thereby allowing the lipid coated beads to display an antigen. This antigen-displaying bead can be used to detect antibodies that react with the displayed antigen. Thus, the antigen-displaying bead is incubated with a test sample and if the antibody is present in the test sample, an antigen-antibody complex will be bound to the lipid coated beads. The antibodies produce ozone and/or hydrogen peroxide (Lerner & Eschenmoser., *Ozone in biology*. Proc. Natl. Acad. Sci. 100(6): 3013-3015 (2003)), which disrupts the lipid bilayer, leading to an altered signal from the lipid bilayer coated beads. Therefore, the presence of antibodies in a test sample can be detected by the present lipid bilayer coated beads, when those beads display and antigen to which the antibody can bind.

In FIG. 24, biotin is similarly attached to a lipid bilayer coated bead and a streptavidin-linked antigen is bound to the biotin. The antigen immobilized on the bead will bind and capture a selected antibody if the antibody has a free binding site for the antigen. A test sample is mixed with a limiting amount of the same antibody that can bind to the antigen displayed by the lipid coated beads, and the mixture is incubated to permit antigen-antibody complexes to form. The lipid bilayer coated beads that display the antigen are then added to the mixture. These beads will then bind any antibody that is not already bound to free antigen from the test sample. Large amounts of antibodies will be bound if the test sample has little or no competing antigen, whereas only small amounts of antibodies will be bound to the lipid coated beads if the test sample contains large amounts of competing antigen. Antibodies produce ozone and/or hydrogen peroxide (Lerner R A and Eschenmoser A., Ozone in biology. PNAS 100(6): 3013-3015 (2003)), which disrupts the lipid bilayer, leading to an altered signal from the lipid bilayer coated beads. Thus, the signal from the beads will be greater if lesser amounts of antigen are present in the test sample, than if greater amounts of antigen are present in the test sample.

Figure 25:
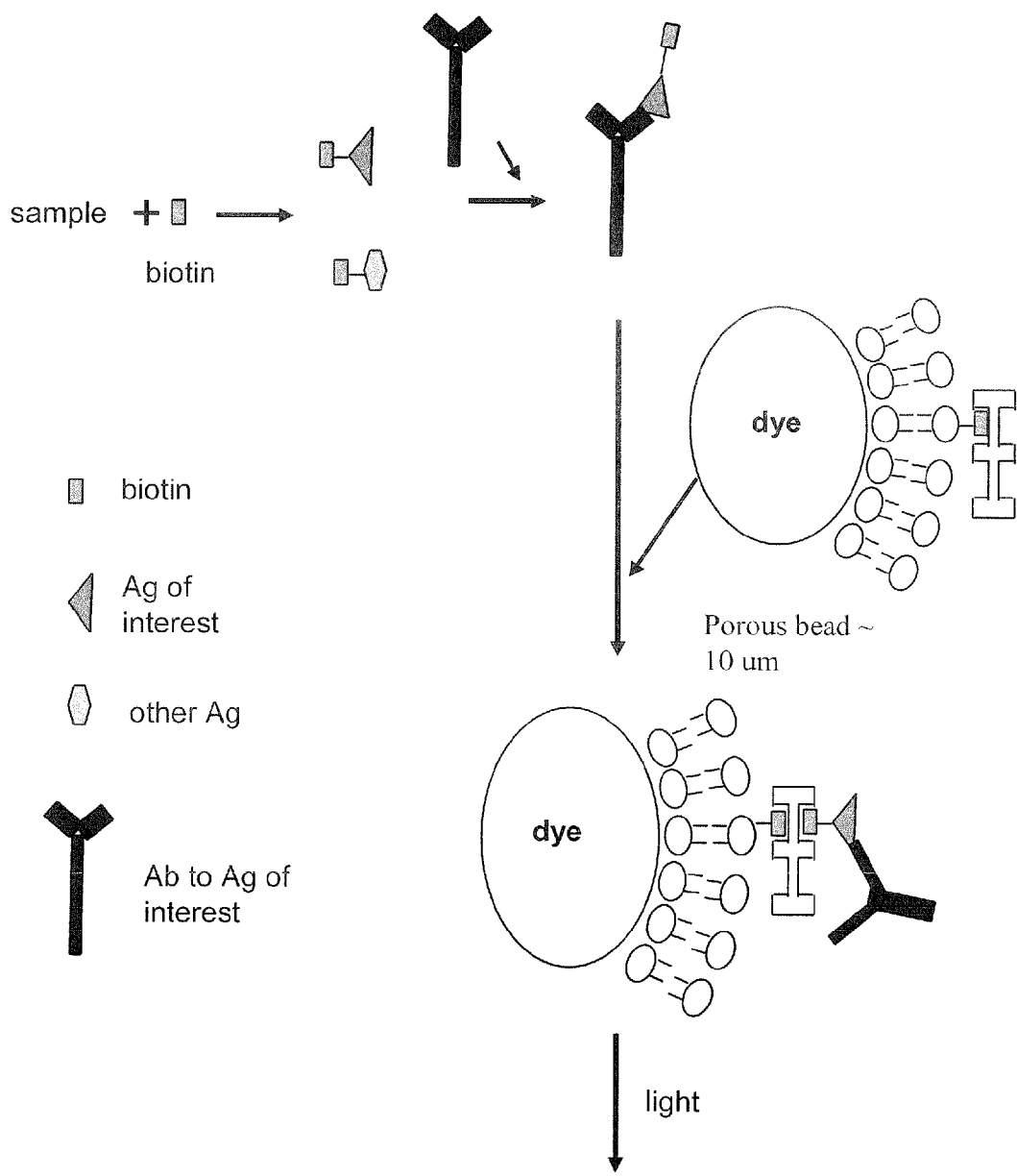
FIG. 25 illustrates another immunoassay contemplated by the invention, which includes capture of immune complexes of biotinylated antigen. An antigen sample is biotinylated and then exposed to an antibody that specifically binds to an antigen of interest. Streptavidin-labeled lipid bilayer-supported beads are added that will bind biotinylated antigens. If the antigen of interest is present in the sample, the antibody will also be bound to the lipid bilayer coated beads. The ozone/hydrogen peroxide generated by the antibody (e.g., upon exposure to ultraviolet light) will disrupt the lipid bilayer and release materials (e.g. a dye) within the lipid bilayer-supported beads.
Figure 26:
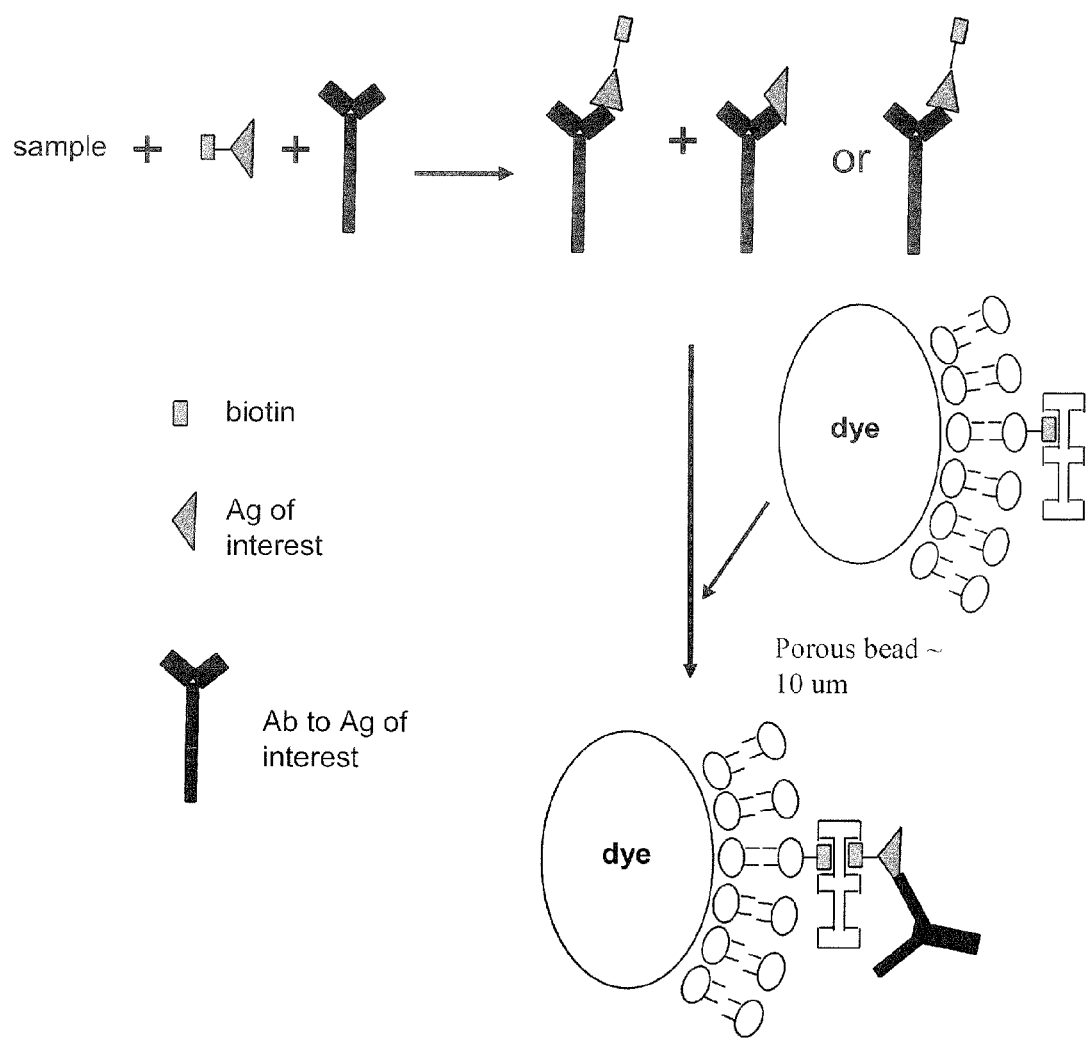
FIG. 26 illustrates capture of immune complexes using competition of antigen in sample with biotinylated antigen. Sample is mixed with biotinylated antigen and then exposed to an antibody that binds both the antigen of interest and the biotinylated antigen. The streptavidin-lipid bilayer coated beads are added and the amount of fluorescence detected (e.g., after exposure to ultraviolet light) is directly related to the amount of antibody bound. The binding of the biotinylated immune complex will be reduced if antigen is present in the sample because the sample antigen is not biotinylated.

When used as a detector molecule, biotin and streptavidin have utility in numerous immunoassays contemplated by the invention. For example, biotin and streptavidin can effectively capture both an analyte or antibody of interest and a competing analyte or antibody of the same or similar structure. This is illustrated in FIG. 25, where the lipid-coated beads display streptavidin, which can bind biotin and any molecule to which biotin is attached. Thus, all antigens in a test sample can be bound to biotin. Then an antibody that reacts with only one selected antigen is missed with the test sample. Thus, the only antigen-antibody complexes formed are those that contain the selected antibody, which recognizes and binds to the antigen of interest. After incubation, a limiting amount of the streptavidin displayed lipid coated beads shown in FIG. 25 are added to the mixture. The lipid coated beads will bind to the biotin linked antigens from the test sample. If a large proportion of the antigens are bound to the selected antibody, then a substantial proportion of the lipid coated beads will be complexed with antigen-antibody complexes, giving rise to a large signal change because the bound antibodies produce ozone and/or hydrogen peroxide that disrupts the lipid bilayers surrounding the dye-impregnated or dye-coated beads.

In some embodiments, additional factors can be added to the assay or attached to one of the molecules used in the assay to modulate the signal or the kinetics of signal production. For example, a source of singlet oxygen can be added to the assay when antibody oxidative disruption of the lipid bilayer is used (see, e.g., FIG. 29). The source of singlet oxygen promotes antibody catalyzed ozone and hydrogen peroxide generation thereby increasing lipid bilayer disruption. Sources of singlet oxygen include, for example, hematoporphyrin and methelyne blue.

Figure 27:
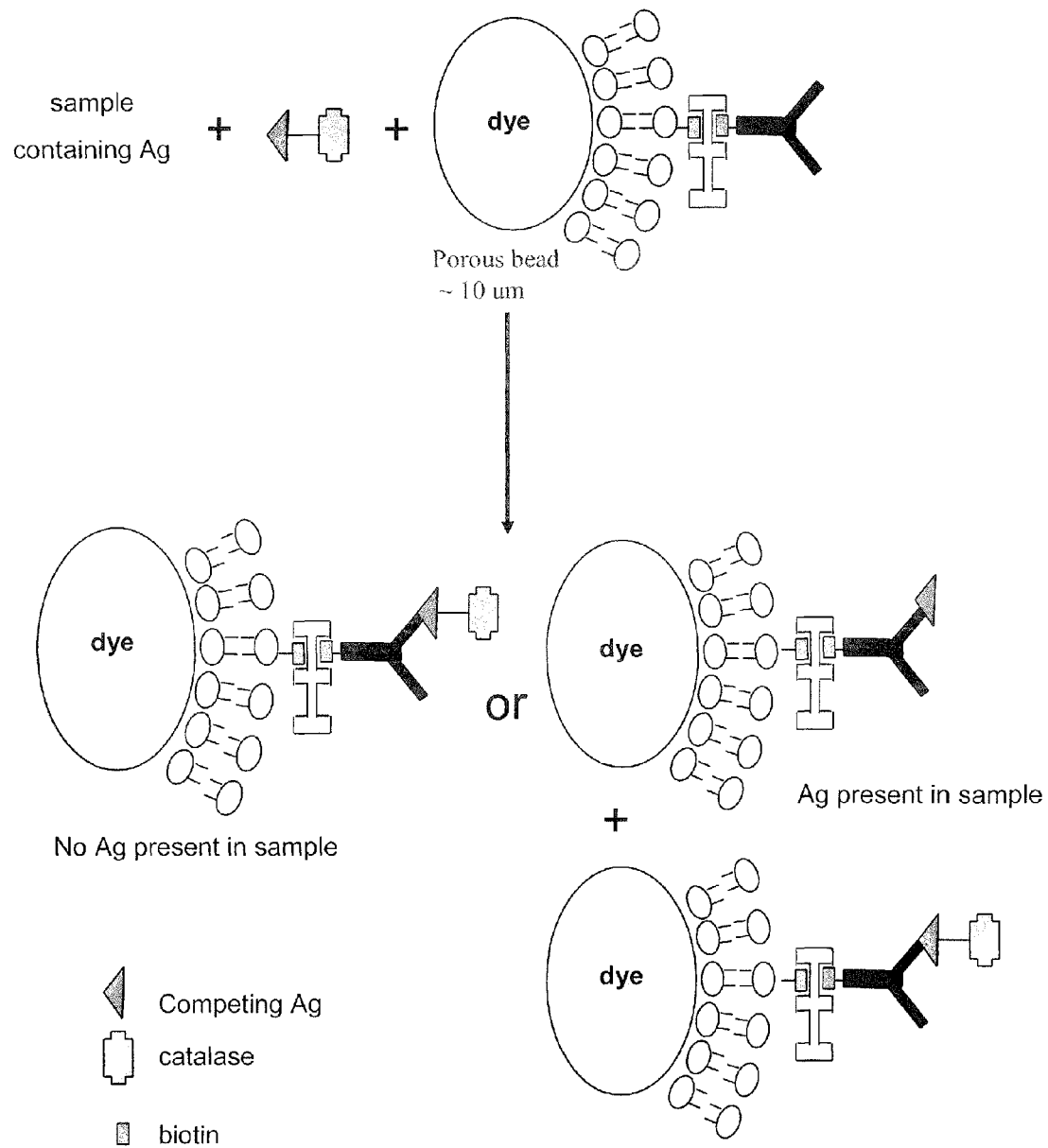
FIG. 27 illustrates an immunoassay of the invention. This immunoassay illustrates use of a catalase-conjugated antigen to compete with antigen in a test sample for binding to an immobilized antibody. Thus, an antibody is immobilized onto lipid bilayer-supported beads. This antibody can recognize a specific antigen that may be present in a test sample. A sample of the same antigen is linked to catalase to form a competing antigen preparation. Catalase can completely attenuate the production of ozone and/or hydrogen peroxide by antibodies. Thus, if no antigen is present in a test sample, the antibody will bind the antigen-catalase conjugate and no ozone or hydrogen peroxide will be generated. However, if antigen is present in the sample, some of the immobilized antibodies will bind free antigen and will generate ozone or hydrogen peroxide, which will disrupt the lipid bilayer, thereby releasing the contents (e.g. a dye) of the lipid bilayer-supported beads. When no antigen is present in the sample, the substantially none of the contents of the lipid bilayer-supported bead will be released.
Figure 28:
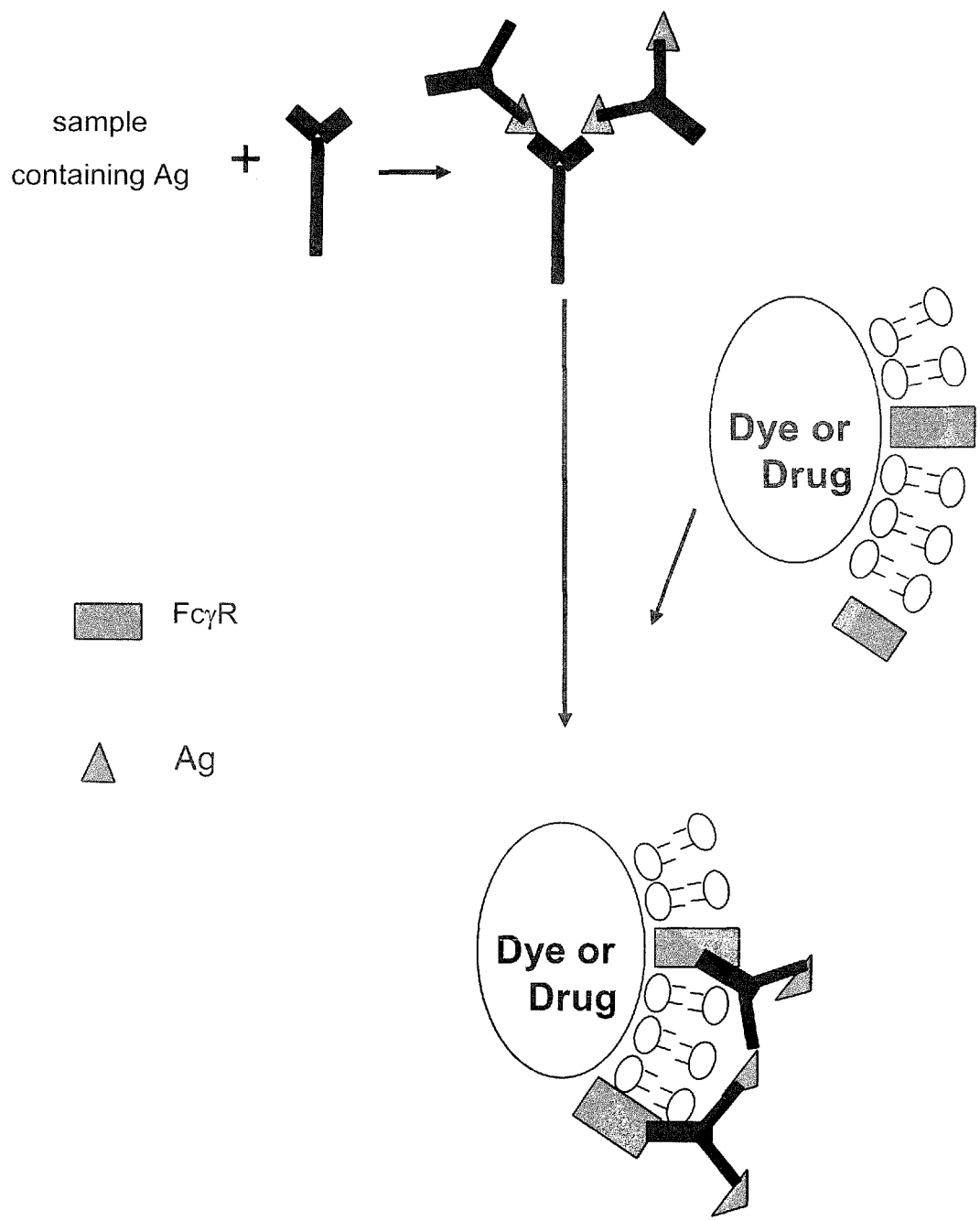
FIG. 28 illustrates immunoassays and delivery systems of the invention that utilize lipid bilayer-supported beads with immobilized FcγRIIb. FcγRIIb (CD32) is a low affinity IgG receptor that can bind monomeric IgG with a $K_D$ of about $10^{-6}$ M. However FcγRIIb binds aggregated IgG with high avidity. Thus, when aggregated immune complexes are present, due to the presence of high amounts of antigen, more IgG will be bound by the immobilized FcγRIIb. FcγRIIb binds to immune complexes containing IgG1 or IgG3. FcγRIIb has a single polypeptide chain with a molecular weight of about 34043 daltons (310 amino acids) and is therefore small enough to be easily made by recombinant procedures and can readily be immobilized onto lipid bilayer-supported beads so that the binding domain is available for binding IgG in the solution surrounding the lipid bilayer-supported beads. When large numbers of IgG are bound, more disruption of the lipid bilayers occurs (e.g., after exposure to ultraviolet light) and more of the contents (e.g., a dye or a drug) encapsulated within the lipid bilayer-supported beads are released.
Figure 29:
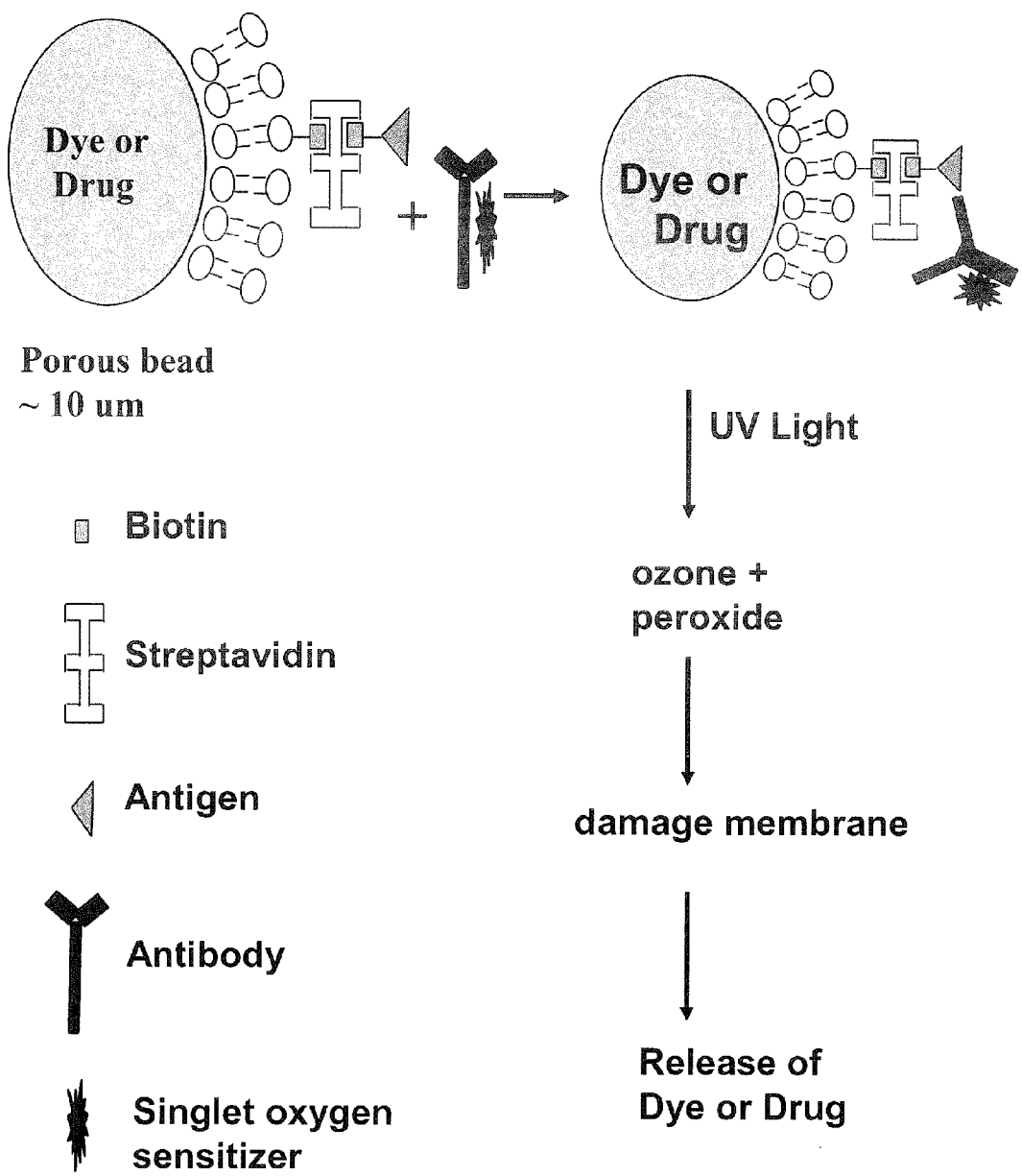
FIG. 29 illustrates immunoassays and delivery systems where the production of ozone and/or hydrogen peroxide is enhanced by addition of a singlet oxygen photosensitizer such as hematoporphyrin or methelyne blue. Thus, a selected antigen is immobilized onto lipid bilayer-supported beads. This preparation of antigen-immobilized lipid bilayer-supported beads is mixed or administered with a singlet oxygen photosensitizer. If antibody is present and binds to the immobilized antigen, the production of ozone and/or hydrogen peroxide by the antibody (e.g. after exposure to ultraviolet light) is enhanced by the singlet oxygen photosensitizer. This enhanced ozone/hydrogen peroxide generation further disrupts the lipid bilayer and increases the release of encapsulated materials within the lipid bilayer-supported beads.

In other embodiments, the added factor is attached to a competitive analyte and can reduce the signal from the encapsulated dye if the competitive analyte binds to the lipid-coated bead. For example, as shown in FIG. 27, catalase can be used to reduce the signal of a competitive analyte (i.e. an antigen) because catalase can completely attenuate the production of ozone and/or hydrogen peroxide by antibodies. Thus, if no antigen is present in a test sample, the antibody will bind the competitive analyte, which is an antigen-catalase conjugate, and insubstantial amounts of ozone or hydrogen peroxide will be generated when this competitive analyte binds to the antibodies immobilized on the lipid-coated beads because the catalase inhibits such ozone/hydrogen peroxide production. When significant amounts of antigen are present in the test sample, the antibodies immobilized on the beads will bind free antigen from the sample. Because no catalase is present on the test sample antigen, antibodies bound thereto will generate ozone or hydrogen peroxide, which will disrupt the associated lipid bilayer, thereby releasing the contents (e.g. a dye) of the lipid bilayer-supported beads.

Figure 30:
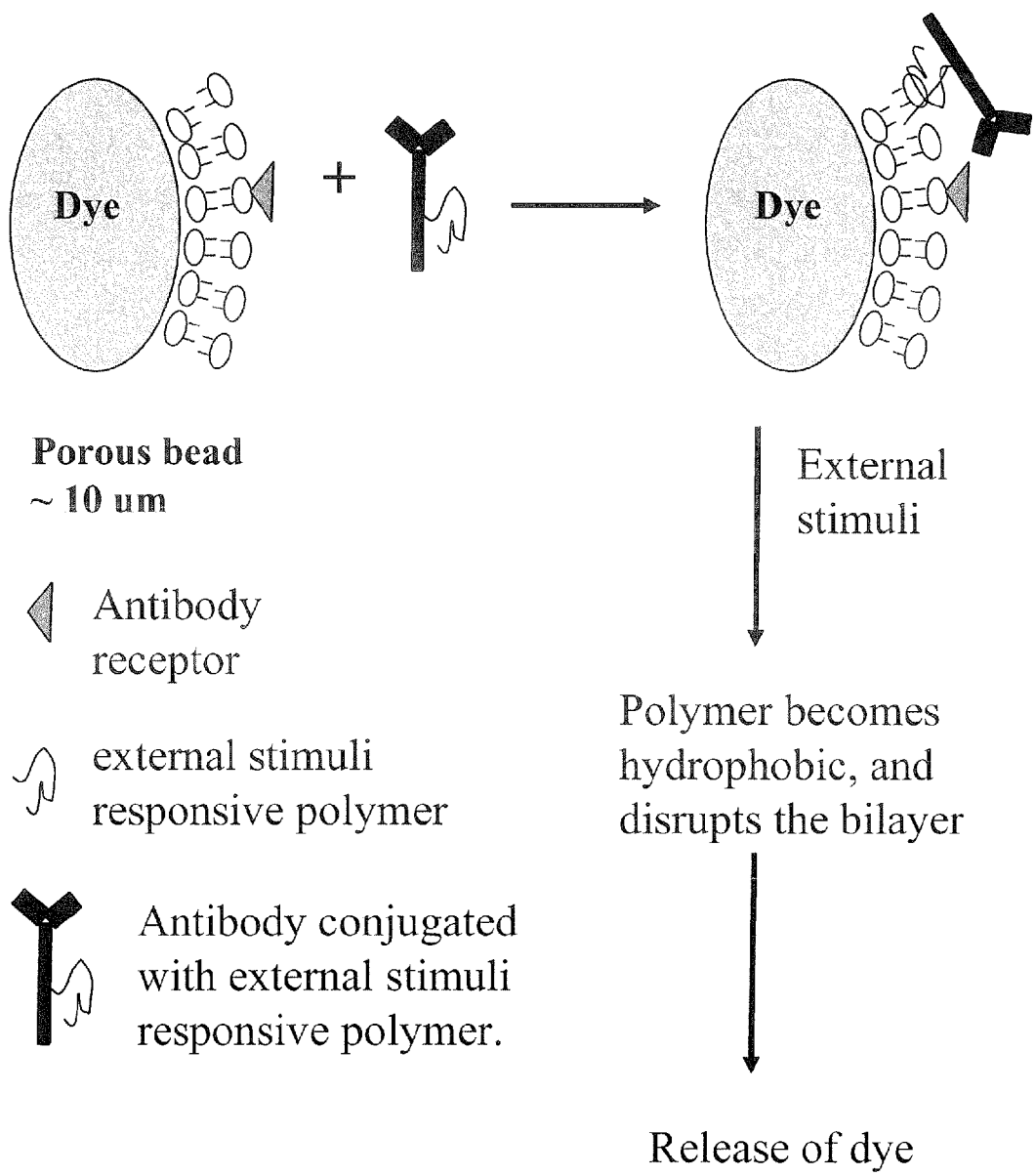
FIG. 30 illustrates immunoassays of the invention that are based on damage of lipid bilayer by external stimuli responsive polymers. The polymers respond to external stimuli in the environment such as change in temperature, changes in hydrophilicity/hydrophobicity, changes in pH and/or changes in light. When conjugated to an antibody, the polymer can be used to detect binding of the antibody to an antigen immobilized onto lipid bilayer-supported beads, because upon binding, the polymer will interact with the lipid bilayer and promote disruption of the lipid bilayer, thereby increasing release of encapsulated materials within the lipid bilayer-supported beads.

In yet another embodiment, a polymer that is responsive to the environment can be attached to an analyte or antibody (see, e.g., FIG. 30). Such an environmentally sensitive polymer changes its conformation when exposed to an environment with a different pH, different hydrophobicity, different hydrophilicity or different solvent conditions. This change in conformation can disrupt the lipid bilayer and lead to a larger signal.

FIG. 27 illustrates an immunoassay of the invention. This immunoassay illustrates use of a catalase-conjugated antigen to compete for binding to an immobilized antibody. Thus, an antibody is immobilized onto lipid bilayer-supported beads. This antibody can recognize a specific antigen that may be present in a test sample. A sample of the same antigen is linked to catalase to form a competing antigen preparation. Catalase can completely attenuate the production of ozone and/or hydrogen peroxide by antibodies. Thus, if no antigen is present in a test sample, the antibody will bind the antigen-catalase conjugate and no ozone or hydrogen peroxide will be generated. However, if antigen is present in the sample, some of the immobilized antibodies will bind free antigen and will generate ozone or hydrogen peroxide, which will disrupt the lipid bilayer, thereby releasing the contents (e.g. a dye) of the lipid bilayer-supported beads. When no antigen is present in the sample, the substantially none of the contents of the lipid bilayer-supported bead will be released.

Detectable Labels

A "detectable label" is any labeling or signaling moiety known to one of skill in the art including chemicals, fluorescent dyes, ion-sensitive dyes, pH-sensitive dyes, proteins, peptides, biotin, radionuclides, enzymes, radioisotopes, chemiluminescent molecules, contrast agents, signaling agents, and chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Detectable labels can be optically detectable, fluorescently detectable, radioactively detectable, magnetically detectable, immunologically detectable, ionically detectable, chromatographically detectable, thermally detectable, and/or enzymatically detectable. Thus, for example, column of beads can be prepared and if the lipid layer is disrupted the detectable label can be detected in the solutions eluted from the column (eluent). The beads can be suspended in solution and after contact with the test sample, aliquots of the suspension can be removed and tested to see if there is detectable label in the solution. Flow cytometry can also be used, for example, when a dye is adsorbed onto or covalently attached to the bead and disruption of the lipid bilayer causes the dye to be exposed to a factor that alters its signal (e.g., a fluorescence quenching molecule, or a change in pH or a change in ionic concentration).

The analytical methods and assays of the invention can detect small amounts of released label, for example, as little as about 1%, 2%, 5%, 10%, 15%, 20% or 25% of the detectable label encapsulated within the supported lipid bilayers of the invention.

One advantage of attaching detectable labels to beads or impregnating beads with detectable label for screening purposes is that numerous molecules of the detectable label become attached per bead. The resulting multiplicity of label molecules concentrates the label in one location (the bead) and can increase the signal from the bead.

A "test sample" as used herein, refers to any substance which may contain the analyte of interest. A sample can be biological fluid, such as whole blood or whole blood components including red blood cells, white blood cells, platelets, serum and plasma, ascites, urine, cerebrospinal fluid, and other constituents of the body which may contain the analyte of interest. Optionally, samples may be obtained from water, soil, vegetation, or solid surfaces such as work benches.

Compositions

The supported lipid bilayers of the invention can be formulated to contain a therapeutic agent and prepared as a pharmaceutical composition that can be administered to a mammalian host, such as a human patient. Such compositions can be adapted to the chosen route of administration. Administration can be oral, parenteral, intravenous, intramuscular, topical, transdermal or subcutaneous.

The compositions of the invention that include a therapeutic agent encapsulated by a supported lipid bilayers can be administered in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and so forth. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and so forth. The proteinoid microsphere composition may be suspended in a syrup or elixir that can contain sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed.

The supported lipid bilayers compositions that contain therapeutic agents may also be administered intravenously or intraperitoneally by infusion or injection. Suspensions of the supported lipid bilayers can be prepared in water or saline or buffered aqueous solution, and mixtures thereof. Under ordinary conditions of storage and use, these preparations may also contain a preservative to prevent the growth of microorganisms.

The pharmaceutical dosage forms suitable for injection or infusion can include sterile aqueous solutions or dispersions or sterile powders comprising the therapeutic agent encapsulated by the supported lipid bilayers and adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, sugars, physiological salts, buffering agents and the like. The proper fluidity can be maintained, for example, by the maintenance of the required particle size in the case of dispersions or by adjusting the concentration of lipid coated beads in the formulation. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions may be prepared by incorporating the active compound in the required amount in the appropriate solvent with various of the other ingredients enumerated above, as required, followed by filter sterilization.

For topical administration, the therapeutic supported lipid bilayers may be applied directly to the skin or the wound or suspended in an appropriate liquid and then applied. The proteinoid microspheres can also be administered to the skin as compositions or formulations, in combination with a dermatologically acceptable carrier, which may be a solid or a liquid.

Useful solid carriers include wound dressings, bandages, and the like that can have an absorbent material into which the supported lipid bilayers compositions of the invention are impregnated. Useful liquid carriers include water, physiological buffers, sugar solutions, salt solutions and mixtures thereof, in which the present therapeutic supported lipid bilayers are dispersed at effective levels. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, modified celluloses or modified mineral materials can also be employed with liquid carriers to form spreadable pastes, gels, ointments, soaps, and so forth, for application directly to the skin of the user.

Useful dosages of the therapeutic agents within the supported lipid bilayers of the invention can be determined by comparing their in vitro activity, and in vivo activity in animal models. Methods for the extrapolation of effective dosages in mice, and other animals, to humans are known to the art.

Generally, the concentration of therapeutic supported lipid bilayers in the compositions is from about 0.1% to about 95% by weight. More desired concentrations of therapeutic supported lipid bilayers are from about 10.0% to about 85% by weight. Even more desired concentrations of therapeutic supported lipid bilayers are from about 25% to about 75% by weight. The concentration in a semi-solid or solid composition such as a gel or a powder will be about 10% by weight to about 99% by weight, preferably about 50% by weight to about 95% by weight.

The amount of therapeutic agent required for use in treatment will vary not only with the route of administration, the nature of the condition being treated and the age and condition of the patient and will be ultimately at the discretion of the attendant physician or clinician.

The therapeutic supported lipid bilayers are conveniently administered in unit dosage form; for example, containing 5 µg to about 100 mg, conveniently about 10 µg to about 50 mg, most conveniently, about 100 µg to about 10 mg therapeutic agent per unit dosage form.

Ideally, the therapeutic agent is administered to achieve sustained peak plasma concentrations of from about 0.1 to about 10 nM, desirably, about 0.2 to 10 nM, most desirably, about 0.5 to about 5 nM. This may be achieved, for example, by the intravenous injection of a 0.05 to 5% suspension of the therapeutic supported lipid bilayers, optionally in saline, or orally administered as a bolus containing about 1-100 mg of the therapeutic supported lipid bilayers. Desirable blood levels are maintained by the sustained low level release of the therapeutic agent from the therapeutic supported lipid bilayers. Intermittent infusion or administration of the encapsulated therapeutic agent can be performed as needed, for example, once or twice daily when the plasma level of the therapeutic agent declines to suboptimal levels.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations such as multiple topical applications in order to optimize treatment of a wound or skin condition.

The invention will be further described by reference to the following detailed examples, which are given for illustration of the invention, and are not intended to be limiting thereof.

Example 1

Lipid Bilayers on Porous Beads

Used in Suspension and in Packed Microcolumns

This Example shows that porous silica beads are a robust, new substrate for lipid bilayers. The lipid bilayer microbeads formed as described herein are sufficiently stable to be used in model membrane disruption studies when the beads are in suspension and in microcolumns. This Example also shows that compounds and/or dyes can be encapsulated into the porous beads coated with lipid bilayer membranes.

Materials

Egg phosphatidyl choline (EPC), 1,2-dimyristoyl-sn-glycero-3-phosphocholine (DMPC), and 1,2-dimyristoyl-sn-glycero-3-[phospho-rac-(1-glycerol)] (sodium salt) (DMPG) were purchased from Avanti Polar Lipids (Albaster, Ala.). The cationic polyelectrolyte poly(p-phenylene-ethynylene) derivative (PPE), and the quencher 9,10-anthraquinone-2,6-disulfonic acid (AQS) were obtained from QTL Biosystems (Santa Fe, N. Mex.). Porous silica beads (50 Angstrom pore, 10 µm diameter) were from Macherey-Nagel (Easton, Pa.). Non-porous silica beads (5 µm diameter) were purchased in dry form from Duke Scientific (Palo Alto, Calif.). Fluorescein sodium salt, TRITON X-100 detergent and melittin were purchased from Sigma. α-Toxin was from Calbiochem (San Diego, Calif.). $NH_4OH$, $H_2O_2$ and HCl were purchased from VWR (West Chester, Pa.). Deionized ultra pure water (Barnstead International, Dubuque, Iowa) was used throughout all experiments.

Methods

Preparation of Fluorescein Soaked Bead.

Known amounts of silica beads were cleaned and treated with a mixture of 4% $NH_4OH$ and 4% $H_2O_2$ at 80° C. for 10 minutes. The beads were then rinsed in distilled water once and treated with a mixture of 4% HCl and 4% $H_2O_2$ at 80° C. for 10 min. Beads were rinsed in distilled water five times and suspended in a known volume of distilled water. Portions of beads (10 mg) were suspended in micro-centrifuge tubes containing 300 µL of 10 mM fluorescein in Tris buffer (100 mM Tris, 150 mM NaCl, pH 7.4) for a minimum of 3 days.

Coating Non-Porous Silica Beads with PPE Polymer.

The fluorescent cationic polyelectrolyte poly(p-phenylene-ethynylene) (PPE) was coated onto silica beads using sufficient polymer (based on an estimated molecular area and an extinction coefficient of 35,100 L/mol*cm per polymer repeat unit (PRU)) to provide 1.2 times monolayer coverage. The silica beads were suspended in ultrapure water and stirred at room temperature for 30 minutes. Bead suspensions were separated from the solution by centrifugation and the colorless supernatant was discarded. The PPE-coated microspheres (MS-PPE) were rinsed with ultrapure water using four cycles of rinsing, centrifuging, decanting and resuspension.

Formation of Lipid Bilayers on Beads.

Fluorescein-soaked beads were separated from fluorescein solution by centrifugation and coated with a single, lipid bilayer. The lipid (or mixture of lipids) in chloroform was dried under a stream of nitrogen followed by vacuuming for half an hour. Unilamellar vesicles were prepared by hydrating the dry lipids with Tris buffer followed by the sonication (Aquasonic, Model 500, VWR) for 20 min. Ice was added to the sonicator bath if necessary to maintain ambient temperature. Lipid bilayers were formed around the beads by vigorous vortexing of the beads with a suspension of unilamellar vesicles for 5 minutes followed by 25 minutes incubation without vortexing. Excess lipids and fluorescein dye released from the porous beads during the formation of bilayer were removed by rinsing the lipid coated beads in Tris buffer at least 15 times.

Preparation of Microfluidic Channels.

PDMS microchannels were constructed using soft lithographic techniques available in the literature. The microfluidic channels were fabricated with weirs to hold the beads in place. The dimensions of the microchannel were: 2 cm (length)×250 µm (width) 60-70 µm (height). In order to trap beads, near the outlet the depth of the channel was limited to 12-15 µm. The prepared PDMS channel was irreversibly sealed onto a glass slide after exposing both to an Ar plasma.

SEM and Confocal Scanning Laser Microscopy.

The porous silica beads were characterized by scanning electron microscopy (Hitachi S5200, 1 kV). Lipid coated fluorescein containing beads were imaged using a confocal scanning laser microscope (Zeiss LSM510) equipped with an argon ion laser.

Suspension Studies.

Long Term Stability of Lipid-Coated Porous Beads.

Fluorescein encapsulated bead samples (5 mg) in 200 µL of Tris buffer and in micro-centrifuge tubes were kept for a period of one month at 25° C. and at 4° C. Stability of lipid bilayer coatings was measured by monitoring the leakage of dye into the supernatant. The fluorescence intensity of the supernatant was measured using a Model Fluorolog-3 SPEX fluorometer (Instruments S.A., Edison, N.J.). Bilayers on beads were disrupted with 10% (w/v, in Tris) TRITON X-100 detergent at the end of a one month period. The control experiments were carried out using three samples containing lipid bilayer coated blank beads and 1 µM fluorescein solutions kept at 25° C. and at 4° C. Fluorescence intensity of all samples were measured at 25° C.

Disruption of Bilayers by TRITON X-100 Detergent.

Lipid coatings on beads were disrupted using 10% TRITON X-100 detergent. Each sample in micro-centrifuge tubes contained 5 mg of lipid bilayer coated, fluorescein entrapped beads in 200 µL of Tris buffer. Samples were centrifuged and 100 µL aliquots of supernatant were mixed with either 100 µL of Tris buffer or 100 µL of 10% TRITON X-100 detergent in separate centrifuge tubes. The fluorescence intensity of each mixture was immediately (time=0) recorded. Each mixture was mixed with its respective bead sample in centrifuge tube and incubated at 25° C. in the dark. After 30 min, samples were centrifuged and fluorescent intensity of the supernatants was measured. Beads were resuspended in their respective supernatants. Fluorescence intensity was again measured at 90 and 150 min.

Interaction of Membrane Active Proteins and Peptides with Supported Bilayer Membranes.

Experimental procedures were similar to the TRITON X-100 detergent based analysis. For experiments with α-toxin, three different toxin concentrations: 15, 45 and 250 µg/mL were used at 37° C. and 25° C. Beads coated with EPC were used. In the experiments with melittin, 220 µM melittin was used with beads coated with either 100% EPC, 10:90 (molar ratio) mixture of DMPG and EPC or an 80:20 mixture of DMPG and DMPC. All melittin experiments were conducted at 25° C.

Microfluidic Studies

Detection of Membrane Interactions by Release of Dye.

To create a packed microcolumn of lipid coated beads containing fluorescein, 2 µL of silica bead (diameter=20 µm) containing suspension (0.05 mg/µL) was injected into a microfluidic channel by applying vacuum at the outlet port of the microchannel, followed by the injection of 10 µL of fluorescein-entrapped bead (diameter=10 µm) containing suspension (0.05 mg/µL). The bead packed microchannel was mounted onto a vertical translational stage located in the sample holder space of the fluorimeter. Just below the bead segment, the microchannel was irradiated with an Argon ion laser ($\lambda$=488 nm, 8-10 mW) excitation. The inlet of the column was connected to a buffer reservoir while the outlet was connected to a vacuum source. As the fluorescence intensity at 520 nm was monitored, several microliters of Tris buffer was passed through the microchannel before the injection of TRITON X-100 detergent. By irradiating just beneath the bead segment, we can monitor the disruption of bilayers by monitoring the diffusion of fluorescein from the porous beads into the buffer stream without exposing the fluorescent beads to the laser. After about half an hour, 10 µL of 10% TRITON X-100 detergent was injected into the column through the inlet silicon tubing using a Hamilton syringe.

Detection of Membrane Interactions by Release of Reagent.

A microchannel was packed with a segment (about 1 mm) of streptavidin coated beads to which a non saturating amount of fluorescein biotin had been bound. This was followed by a segment (about 1 mm) of blank silica beads and a segment (about 2 mm) of lipid coated porous beads containing biotin. The blank silica beads were served as the spacer to prevent mixing of fluorescein biotin beads with biotin encapsulated beads. Biotin (25 mM) was encapsulated (according to the same procedure for fluorescein) with a 80:20 (molar ratio) mixture of DMPG and DMPC. A 10 µL aliquot of either 10% TRITON X-100 detergent or 220 µM melittin was injected to the column. The fluorescein biotin bead segment was irradiated at 488 nm and its fluorescence emission intensity was measured at 520 nm every 10 minutes.

Detection of Membrane Interactions by Fluorescence Superquenching.

The preparation of microcolumns with PPE-coated, silica beads was similar to that of with fluorescein containing beads. A 10 µL aliquot of 120 µM AQS was injected to the column. After a certain period of time, a 10 µL aliquot of 1:1 mixture of 120 µM AQS and 220 µM melittin was injected. During this process, the PPE-coated silica bead segment was irradiated at 488 nm and its fluorescence emission intensity was measured at 520 nm every 10 minutes. This experiment was repeated, while injecting 220 µM melittin first, and then 120 µM AQS.

Results

Characterization of Beads with SEM and Confocal Microscopy.

SEM of the porous beads used in this study shows that the beads are spherical and polydisperse with average diameter of about 9 µm. Samples of the beads were crushed, and fractured surfaces were observed by SEM that exhibited very high porosity. The manufacturer specifies the average pore diameter as 50 Angstrom. However, the SEM images indicate that the pores are not regular in size and also that the beads contain a fraction of pores that are much bigger than 50 Angstrom.

Silica beads are negatively charged at pH 7.5. Though fluorescein is also negatively charged at this pH, by incubating the porous beads in a highly concentrated solution of the dye for at least 3 days, the pores were filled with sufficient amounts of dye. After coating them with lipid bilayers, the beads were rinsed with Tris buffer at least 15 times to remove excess lipids and excess dye from the bead suspension. Confocal fluorescence images of the beads packed into a microchannel indicated that dye was encapsulated inside the beads.

Long Term Stability of Lipid-Coated Porous Beads.

The stability of lipid bilayers on the porous silica beads was studied by measuring the leakage of dye from lipid coated beads over a period of one month. Since temperature can influence the fluorescence intensity, the fluorescence of the bead suspension supernatant was always measured at room temperature. The traces with open symbols in FIG. 1 show the leakage of dye during the one month period. The total fluorescence intensity increase at the end of one month period was about 7.2 fold at 25° C., and about 2.5 fold at 4° C. The traces with closed symbols represent the percentage of leakage of the dye, assuming that 100% leakage will occur when the bilayers are disrupted by TRITON X-100 detergent. All the intensities were normalized to the intensity at day one, and corrected for any possible fluctuations in efficiency of fluorescence excitation or emission detection during the experimental period by using fluorescein solutions (1 µM, 4° C., 25° C.) as controls according to Equation (1).

$$I = \left(\frac{I_i - I_o}{I_o}\right) - \left(\frac{I_{flc} - I_{flc,o}}{I_{flc,o}}\right)$$

Here I is the normalized and corrected intensity of the supernatant, for each day, $I_i$ is the fluorescence intensity measured for the supernatant each day, $I_o$ is the fluorescence intensity of the supernatant day one, $I_{flc}$, and $I_{flc,o}$ are the intensities of the control fluorescein solutions on each day and on day one, respectively. The observed fluctuation in intensity of the controls was negligible. The percent leakage was calculated according to Equation (2):

$$\% \text{ Leakage} = \left(\frac{I_i - I_o}{I_{Trt}}\right) 100$$

where $I_{Trt}$ is the total release of dye due to the disruption by TRITON X-100 detergent. The percentage leakage after 30 days of the lipid coated beads kept at 25° C. was about 6.9% and that of beads kept at 4° C. was about 2.4%. It is known that at lower temperatures the membranes can be more stable. The greater amount of fluorescein leakage through the bilayer coating observed at 37° C. may be due to increased lateral diffusion of lipid molecules, as well as the increased rate of diffusion of fluorescein. For the purpose of the assays described here, this leakage may be considered negligible in comparison to the total dye release from the porous beads. However, if less leakage is desired, use of saturated and/or unsaturated lipids with similar molecular sizes and phase transition temperatures may be used. (Note that the EPC employed is a mixture of saturated and unsaturated lipids with different molecular sizes and phase transition temperatures.) Leakage might be further minimized by using suitable lipid composition with appropriate phase transition temperatures. The phase transition temperature of the membrane used in this study (EPC) is below 0° C., and at both 25° C. and 4° C., the membrane is in a fluid phase.

These data indicated that the lipid membranes on beads are relatively stable for well over one month. In comparison, lipid vesicles cannot be stored for more than one week without a substantial loss of encapsulated compounds, and preparation of fresh vesicle samples is often required for long term studies. Thus, the use of lipid bilayer coated porous beads improves the stability and shelf life of lipid bilayer systems, thereby lowering the costs of producing encapsulated formulations.

Suspension Studies

Previous suspension studies on disruption of lipid bilayers have been performed with small unilamellar vesicles where disruption of the lipid bilayer membranes was detected by monitoring the unquenching of a highly concentrated, encapsulated dye. In the present work disruption was monitored via release of fluorescein dye from porous beads, by measuring the increase in fluorescence intensity of the supernatant at 520 nm. Beads were first suspended in Tris buffer containing the disruptor. After selected time periods, beads were sedimented by centrifuging and a portion of the supernatant was taken for the measurement. The measured portion was added back to the bead sample to permit continuous monitoring. The scattering effect that was present in vesicle based studies was minimized by measuring only the supernatant after centrifugation of the beads.

Disruption of Bilayers by TRITON X-100 Detergent.

Figure 2:
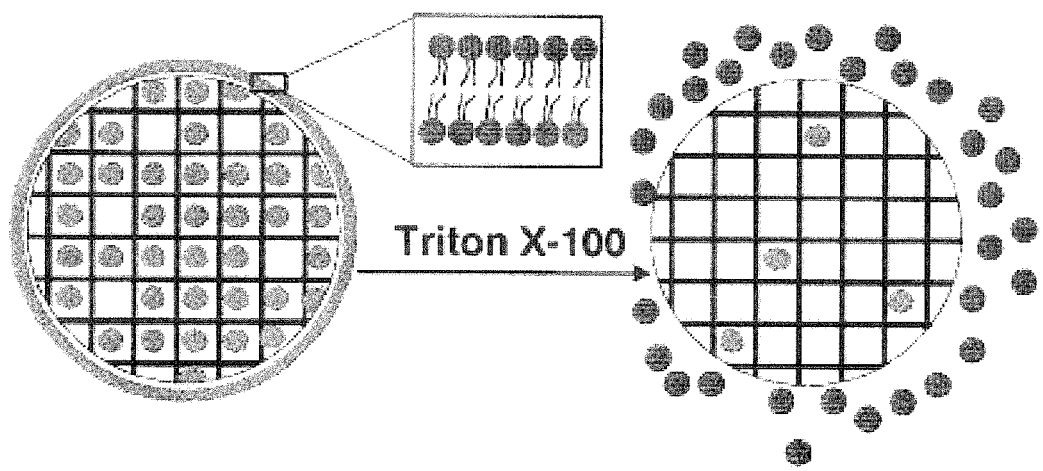
FIG. 2 is a schematic representation of total disruption of phospholipid bilayer coated onto a porous silica bead that contains fluorescein dye. TRITON X-100 detergent solubilizes the entire bilayer while membrane active peptides and proteins form channels or pores through the membrane.
Figure 3:
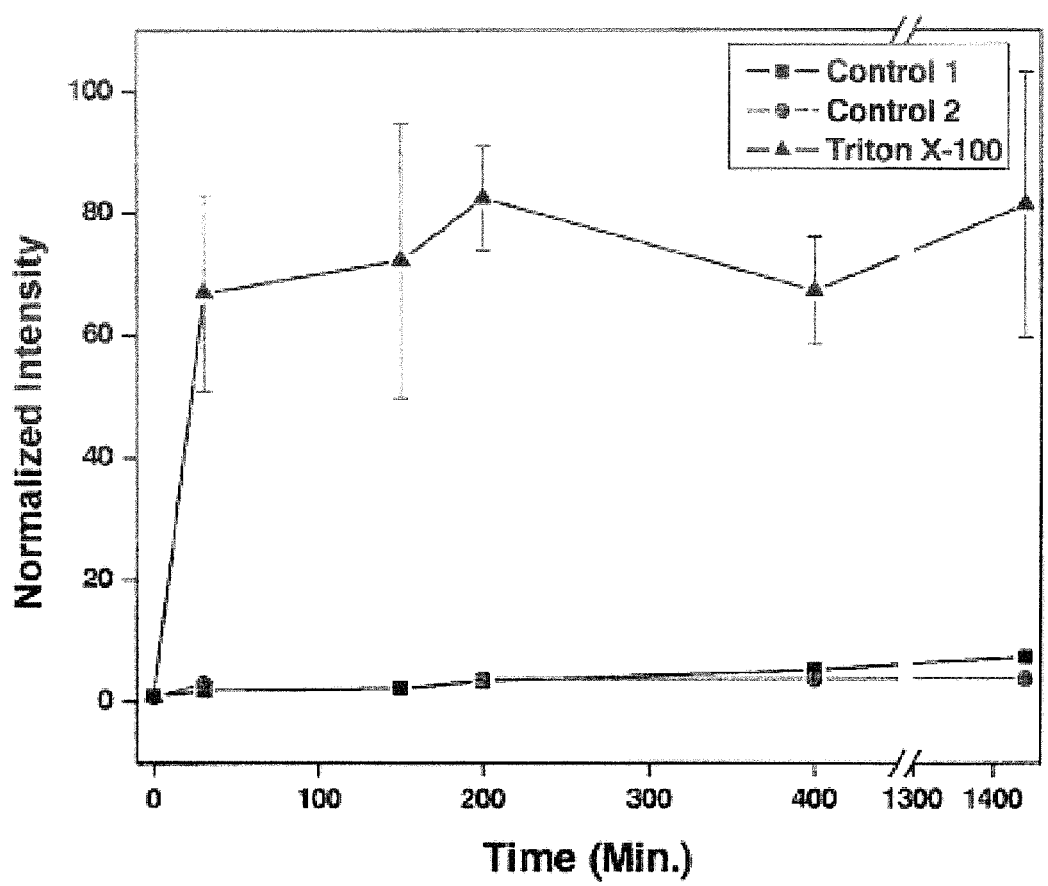
FIG. 3 graphically illustrates the release of dye from lipid bilayer coated microbeads after disruption by TRITON X-100 detergent. The normalized fluorescence intensity is plotted versus time for suspension studies involving EPC bilayer disruption by TRITON X-100 detergent.

TRITON X-100 detergent can disrupt lipid membranes within milliseconds. As the schematic in FIG. 2 shows, dye is released when the lipid bilayer is solubilized by TRITON X-100 detergent. The normalized fluorescence intensity of released dye in the supernatant vs. time is shown in FIG. 3. The disruption of membranes on dye containing beads by TRITON X-100 detergent caused an increase of more than 70 fold in fluorescence intensity of the supernatant during the first 30 min. There was no significant change in the fluorescence intensity of the supernatant after 30 min, suggesting relatively rapid equilibration of release of the dye. The leakage in the absence of TRITON X-100 detergent is shown in the trace with rectangles. The trace with filled circles represents a control sample containing lipid coated porous beads without the dye. These results suggest that TRITON X-100 detergent is an efficient disruptor of lipid membranes supported on porous silica beads and that release of dye fairly rapid and can be viewed as an effective measure of membrane disruption.

Membrane Active Proteins and Peptides within Supported Bilayers.

Alpha-Toxin.

α-Toxin is a membrane active protein secreted by *Staphylococcus aureus*, and has a molecular weight of ~33 kDa. It forms heptameric pores of about 1-2 nm in diameter in phospholipid bilayers. The poration of membranes by α-toxin does not depend on the charge of the lipids and the toxin is most reactive at 37° C. Studies in suspensions were performed at 25° C. and 37° C. for three different toxin concentrations: 15, 45 and 250 µg/mL. The release of fluorescein dye (FIG. 4B) upon exposure of the beads to α-Toxin was much less than that observed after exposure to TRITON X-100 detergent. This is not unusual, considering the toxin's mechanism of membrane interaction. The increase in fluorescence intensity after 150 min was about 6.5 fold at 37° C., and about 3 fold at 25° C. for all three concentrations (data for 45 µg/mL of toxin are not shown in the figure for clarity). The toxin concentrations used in this study were higher than has been used in many published works. The release of similar quantities of dye for all three concentrations indicates the presence of an adequate amount of α-toxin in the medium. The data further suggest the enhanced activity of the toxin at 37° C. The addition of TRITON X-100 detergent after 150 min causes total disruption of bilayers, resulting in an increase in fluorescence intensity of 50 fold. This indicates that a large amount of dye remains in the porous beads after exposure of the bilayers to α-toxin.

These results indicate that although the increase in supernatant fluorescence is significant, showing that fluorescence changes can be used to measure poration, the amount of dye released is relatively low, and the rate of release is slow. Such slow release of dye is likely due to the size, and the number of pores formed by the toxin in the lipid membranes. Only 27% of dye encapsulated in EPC vesicles was released upon incubation with α-toxin. It has been reported that, for lipid vesicles, α-toxin will not disrupt the membranes sufficiently to release all the encapsulated dye. Several different lipid formulations were investigated where the quantities of cholesterol and phosphatidyl ethanolamine along with EPC were varied in an effort to enhance the disruption by α-toxin. None of the different lipid mixtures enhanced the degree of dye leakage beyond that observed with EPC alone (data not presented).

Figure 4A:
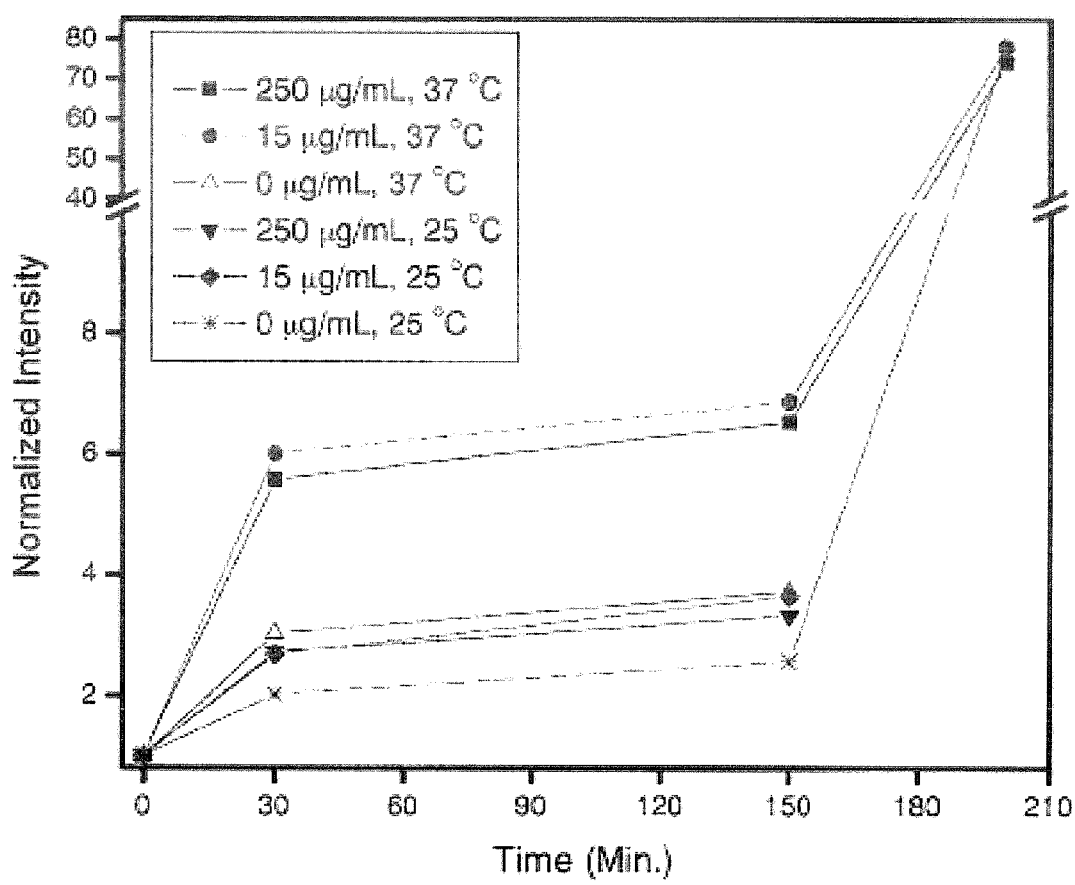
FIGS. 4A-B illustrates the effects of alpha-toxin on lipid bilayer integrity.
Figure 4B:
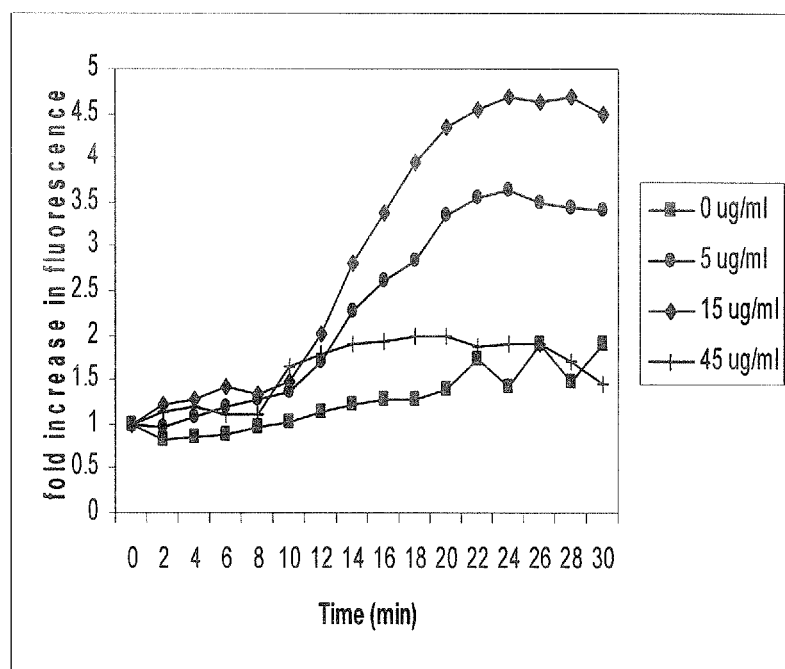

In another experiment a lipid bilayer surrounding a porous bead that contains a pH-reactive molecule (fluorescein) was exposed to α-toxin. The pH outside the beads was adjusted to 11.0, whereas inside the beads the pH was 2.6. The kinetics of disruption of supported lipid bilayer by α-toxin were monitored by recording changes in fluorescence intensity every 2 minutes by flow cytometry. For the first 8 minutes there was no significant change in fluorescence intensity (FIG. 4B). However, after 8 minutes there was a gradual increase in fluorescence intensity (FIG. 4B) resulting from insertion of α-toxin into the supported lipid bilayer thus forming channels permeable to hydrogen cations and hydroxyl ions, which reduces the difference in the pH outside and inside the microspheres. As shown in FIG. 4B, the increase in fluorescence intensity was dependent on the concentration of α-toxin, and it reached its maximum at a concentration of 15 µg/mL of α-toxin. On the other hand, adding α-toxin at a concentration of 45 µg/mL did not cause a change in fluorescence intensity different from the baseline. This can be attributed to insertion of many α-toxin channels at this high concentration leading to disruption of the lipid bilayer and immediate equilibration of the pH inside and outside the porous microspheres.

Melittin.

Melittin, the principal toxic component in bee venom is an antimicrobial peptide with 26 amino acid residues that strongly interacts with negatively charged lipids in a concentration-dependent manner. At low concentrations, melittin tends to form pores in lipid membranes with zwitterionic or negatively charged lipids, while at higher concentrations, it can disrupt membranes on negatively charged lipids in a "detergent-like" action.

Figure 5:
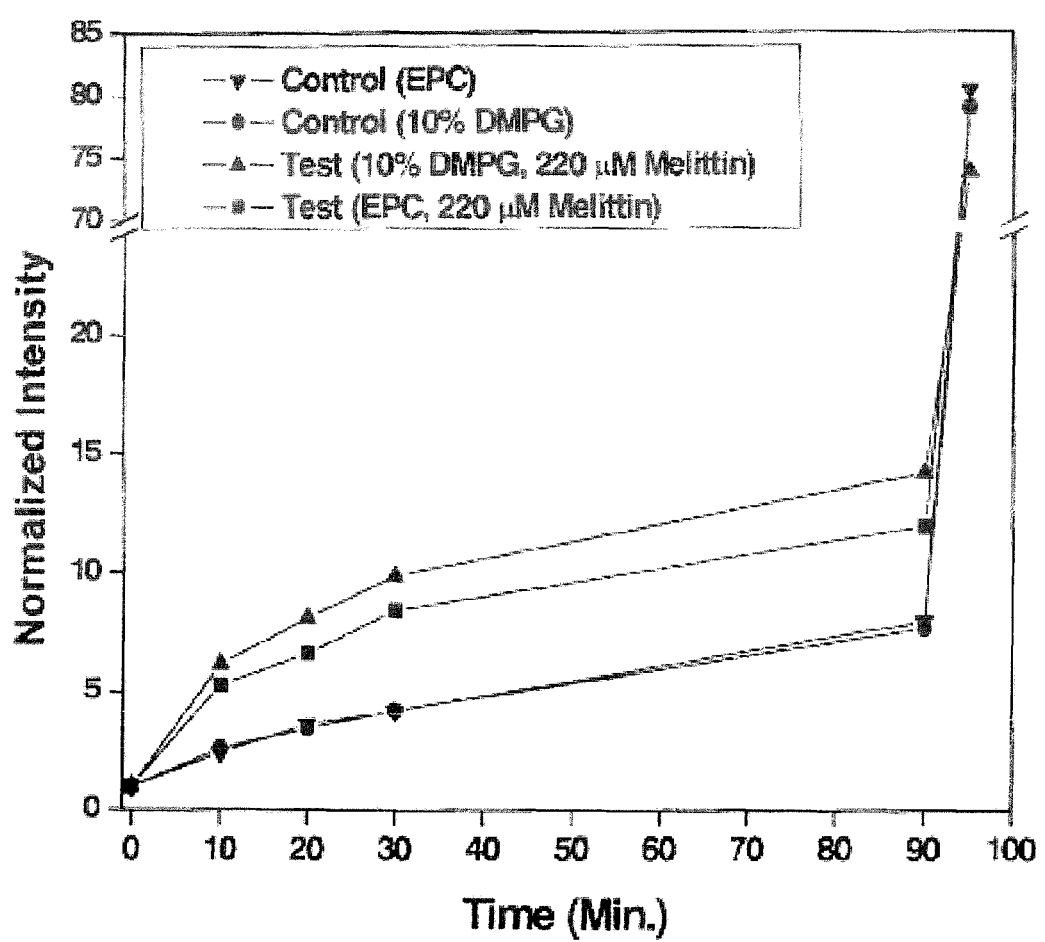
FIG. 5 graphically illustrates dose-dependent release of fluorescent dye from a lipid bilayer coated microbead after introduction of different concentrations of melittin, an antimicrobial peptide that can disrupt membranes if used at sufficient concentration. The graph shows normalized fluorescence intensity (at 520 nm) as a function of time after introduction of 220 pM melittin to bead suspensions. Beads were coated either with EPC or a 10:90 (molar ratio) mixture of DMPG and EPC. 10% Triton was added at 90 minutes.

The interaction of highly concentrated melittin solutions was examined with membranes supported on fluorescein containing porous beads, where the membranes contained 100% EPC or a 90:10 mixture (molar ratio) of EPC and DMPG (a negatively charged lipid). As shown in FIG. 5, the release of dye from porous beads coated with EPC/DMPG, was slightly higher than that observed when the beads were coated with 100% EPC. In the absence of peptide, the amount of dye leakage from the EPC/DMPG beads was similar to that for EPC coated beads.

These observations indicate that high concentrations of melittin and the presence of DMPG in bilayers lead to increased release of encapsulated dye from porous beads through enhanced toxin-membrane interactions.

Figure 6:
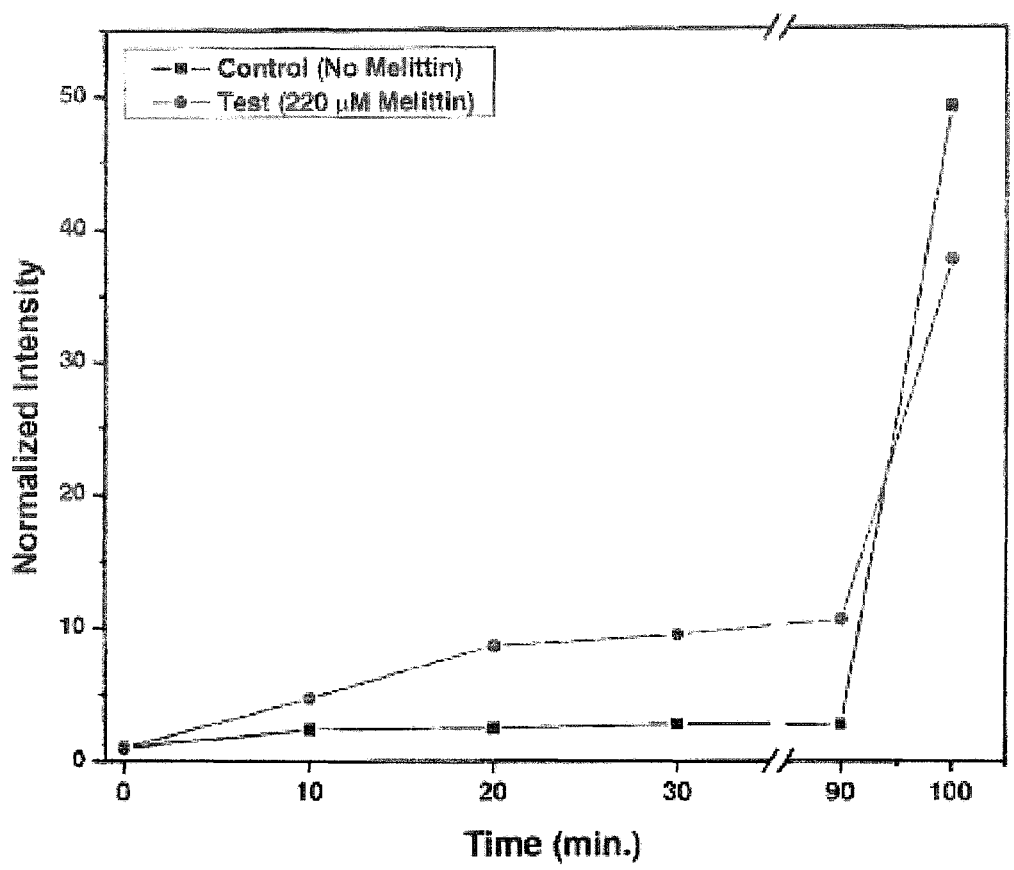
FIG. 6 graphically illustrates that melittin substantially increases dye leakage from membranes containing DMPG. The graph shows normalized fluorescence intensity (at 520 nm) as a function of time for DMPG coated beads suspended in 220 pM melittin. Beads were coated 80:20 (molar ratio) mixture of DMPG and DMPC. 10% Triton was added at 90 min.

In view of the results shown in FIG. 5, the effects of melittin on other mixtures of lipids were examined. FIG. 6 shows that an increase in DMPG content and the inclusion of DMPC instead of EPC in the membranes have a significant influence on melittin action and leakage. A 80:20 mixture (molar ratio) of DMPG and DMPC was used to form the lipid bilayers used in this experiment. The increase in fluorescence intensity due to the membrane-melittin interaction, which results in the release of dye from porous beads was about 10 fold. Although this release was not as high as that observed when using TRITON X-100 detergent, it is notable in comparison to the release with α-toxin.

This experiment also demonstrates that bilayers with negatively charged lipids on negatively charged porous silica beads can be formed. Although higher molar fractions of DMPG were used than DMPC, there is a possibility that the membranes formed had DMPG rich outer leaflets. This may happen because excess amounts (~10 fold, in comparison to the amount of lipids needed to coat the beads) of lipid were used during the coating of silica beads. The composition of lipids on the beads can be ascertained by spectroscopic studies.

The leakage of dye from porous beads, in the absence of melittin was greatly reduced when using the 80:20 mixture (molar ratio) of DMPG and DMPC, relative to that observed when EPC membranes were used. This may be due to the fact that the DMPG and DMPC lipids are of comparable size and have approximately the same phase transition temperature. The reduction in leakage in the absence of toxins, is important as these beads can be used in studies for longer period of time, without losing their sensitivity.

Effect of Supports on Membrane-Toxin Interaction

Although previous studies have shown that the disruption of lipid membranes either by membrane active peptides or proteins can release large amount of encapsulated compounds from unilamellar vesicles, this was not observed with lipid coated porous silica beads. It was possible that the beads employed had multilayers of lipid bilayers around the beads because excess amount of lipids were during the coating, so that the membrane active peptides or proteins may not have penetrated through all the layers to form continuous pores or channels. This possibility was tested by using just enough lipid in the coating procedure to form a single bilayers around the beads. Using these "single bilayer beads" no significant change in release of dye was observed upon exposure to toxin, although increased leakage of dye was observed when no toxin was present, indicating that excess amounts of lipids are needed to effectively coat the beads and to obtain defect-free supported membranes.

Microfluidic Studies

Experiments were designed to explore development of microfluidic methods to study the membrane-toxin interactions. These microfluidic studies on membrane-toxin interactions were based on on-column detection of released dye and reagent from porous beads, and superquenching of fluorescent polymers coated on to solid beads.

Detection of Membrane Interaction by Release of Dye

Figure 7:
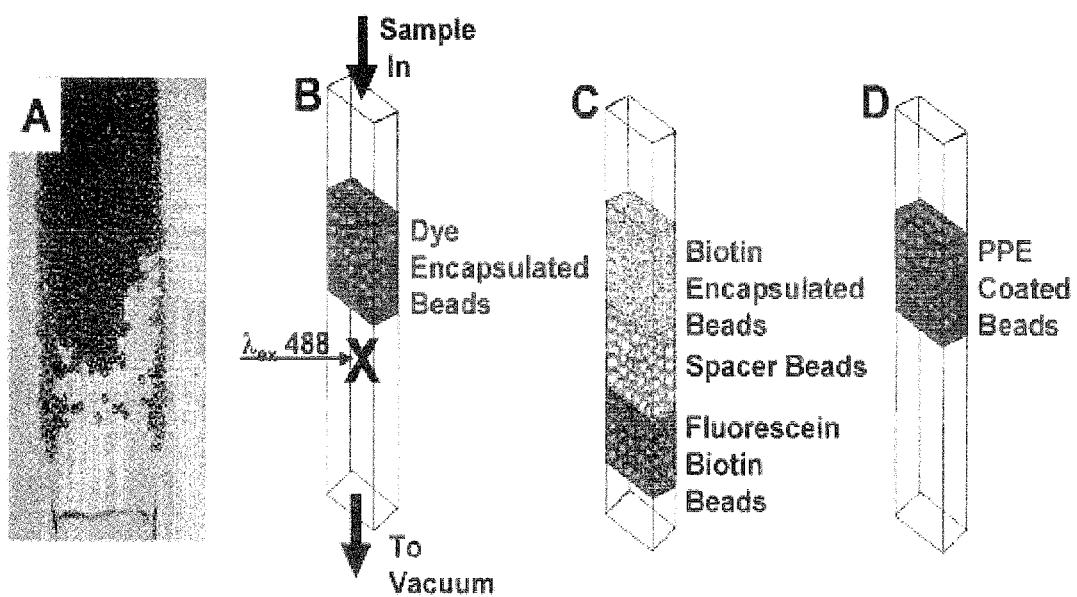
FIGS. 7A-D illustrates microcolumn configurations for membrane interaction analyses.
Figure 8:
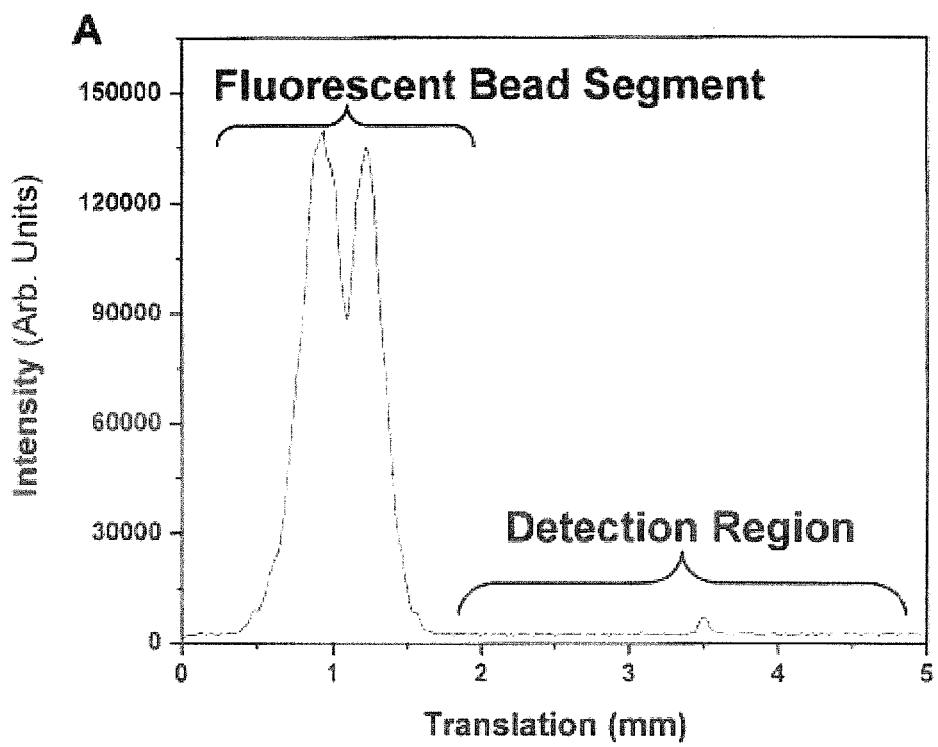
FIG. 8A illustrates alignment of the bead packed microchannel for fluorimetry experiments, showing that the detection region is downstream of the packed beads so that dyes or other compounds released from the beads can be detected.
FIG. 8B shows that little or no dye is released from the beads packed into microcolumns, as detected by a microfluidic stability study. The very low intensity indicates the stability of lipid coated beads when packed in the microchannel.
FIG. 8C illustrates release of dye from microbeads packed into a microcolumns during a microfluidic disruption study using TRITON X-100 detergent to disrupt the lipid bilayer membranes on microbeads. The first broad peak occurred in the presence of buffer flow through the column. The second peak occurred when no buffer was allowed to flow through the column.
Figure 8:
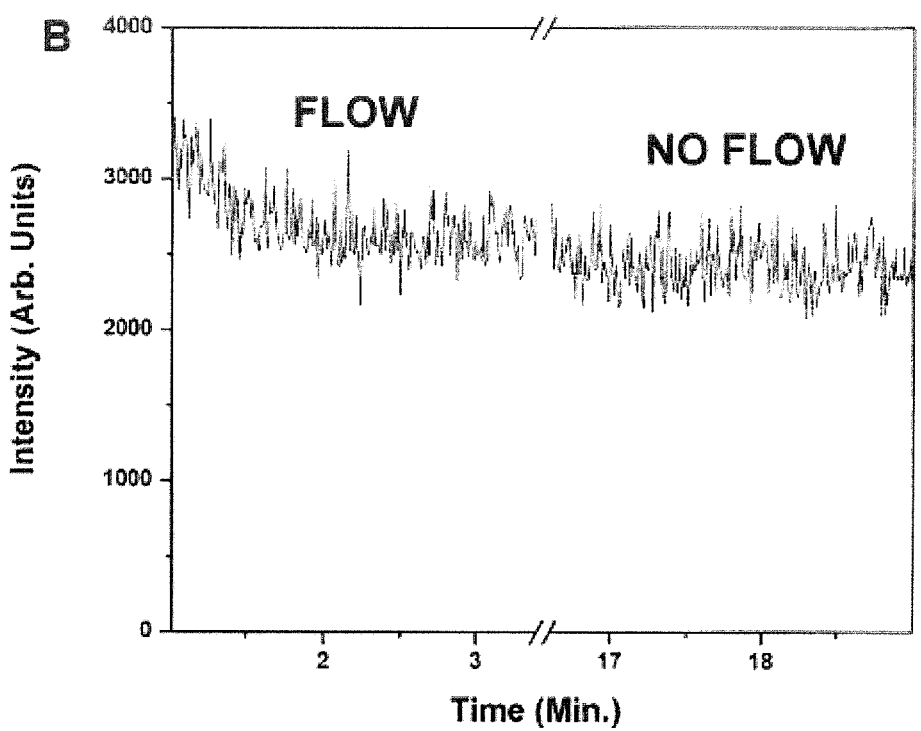

FIG. 7A shows the optical micrograph of a fluorescent (fluorescein encapsulated) bead packed microcolumn. The packed segment was about 2 mm long. The disruption of the membranes on porous silica beads (containing fluorescein dye) by TRITON X-100 detergent was detected by monitoring the release of the dye from the beads, at a point just below the bead segment as indicated in FIG. 7B. A region that was originally non fluorescent was used so that alignment of the microcolumn with the excitation source and the detector was initially challenging. To overcome this, the fluorescent bead segment was first aligned with the beam from an Argon ion laser and the detector, then the column was moved vertically to a suitable region while monitoring the fluorescent signal from the microcolumn, as shown in FIG. 8A. The detection region should be downstream from the bead segment, and the signal should not interfere with the one that arises from adjacent fluorescent beads. The microcolumn was irradiated at 488 nm and fluorescence intensity was monitored at 520 nm.

One concern about lipid membrane-coated beads during microcolumn studies is the stability of the lipid membrane. Lipid membranes might be damaged during packing, and the close contact of beads after the packing may disrupt the membranes. The stability of lipid membranes on porous beads, containing fluorescein dye was examined by monitoring the leakage of the dye from beads before the injection of TRITON X-100 detergent. FIG. 8B shows the fluorescence intensity of the detection region, at flow and no flow conditions. Tris buffer was used a eluent and the column was washed with this buffer using a flow rate of about 1.2 μL/min for about 15 min. The flow was then stopped for another 15 min. Had the dye leaked out to a significant extent, it would have diffused into the buffer stream and increased the fluorescence intensity at the detection region. No such increased fluorescence signal was observed, indicating that the bilayers are stable enough to withstand packing into a microcolumn and that no significant leakage of dye occurs from the lipid membrane-coated porous particles.

Fast disruption of lipid membranes by TRITON X-100 detergent should result in a rapid and large release of entrapped dye from porous silica beads. After injecting 10 μL of 10% TRITON X-100 detergent into the fluorescein-encapsulated bead-containing microcolumn, flow through the column was reduced to zero and the beads in the column were incubated with TRITON X-100 detergent at no flow condition for about 5 min. Flow through the column was then resumed and any released fluorescein dye moved through the detection point. As FIG. 8C shows, a fold increase in fluorescence intensity was observed. The following gradual decrease in fluorescence intensity is due to the dilution of the released dye in the transport buffer. In the absence of flow ($2^{nd}$ peak), the intensity is nearly constant. This suggests that the dye is relatively immobile in the absence of buffer flow. The initial signal ($1^{st}$ peak) obtained here is ~80% less than that of observed in suspension studies. This is mainly due to the fact that we are monitoring the continuous release of dye in the microcolumn, whereas in suspension studies, we monitored the total dye that was accumulated for a certain period of time. Another factor that can contribute to the reduced signal is the dilution of dye due to the mixing with the buffer stream. The initial high fluorescence intensity can be due to the release of dye that was trapped between the interface of silica bead and inner leaflet of the lipid bilayer. After a certain period, the fluorescence intensity becomes less due to the slow diffusion of dye from bead pores and the near complete removal of dye from porous beads.

Detection of Membrane Interaction by Release of Reagent

In this study the membrane-toxin interaction was investigated using the microcolumn system by monitoring a bimolecular reaction on downstream beads. An ostrich quenching-unquenching phenomena was employed with detection of a fluorescein biotin-streptavidin interaction to monitor lipid membrane interactions of TRITON X-100 detergent and melittin. The unquenching of fluorescence was the signal for the disruption. When a suitable amount of fluorescein-labeled-biotin was bound to streptavidin, fluorescein interacted with cis biotin-binding pocket on streptavidin. This results in quenching of its fluorescence intensity, which is known as ostrich quenching. Introduction of free biotin displaced the fluorescein from the cis binding pocket thus unquenching the fluorescence signal. As shown in FIG. 7C, a segment of fluorescein-biotin coated streptavidin beads (diameter=20 μm) was packed at the bottom of the microfluidic channel. Packed on top of that was a segment of blank silica (no porous) beads followed by lipid coated porous silica beads that contained biotin. Once the lipid membrane on the biotin containing porous beads was disrupted, biotin was released and bound to the streptavidin downstream, replacing the fluorescein (tagged to biotin) from biotin-binding pockets, thus increasing the fluorescence intensity of the fluorescein-biotin segment.

Figure 9:
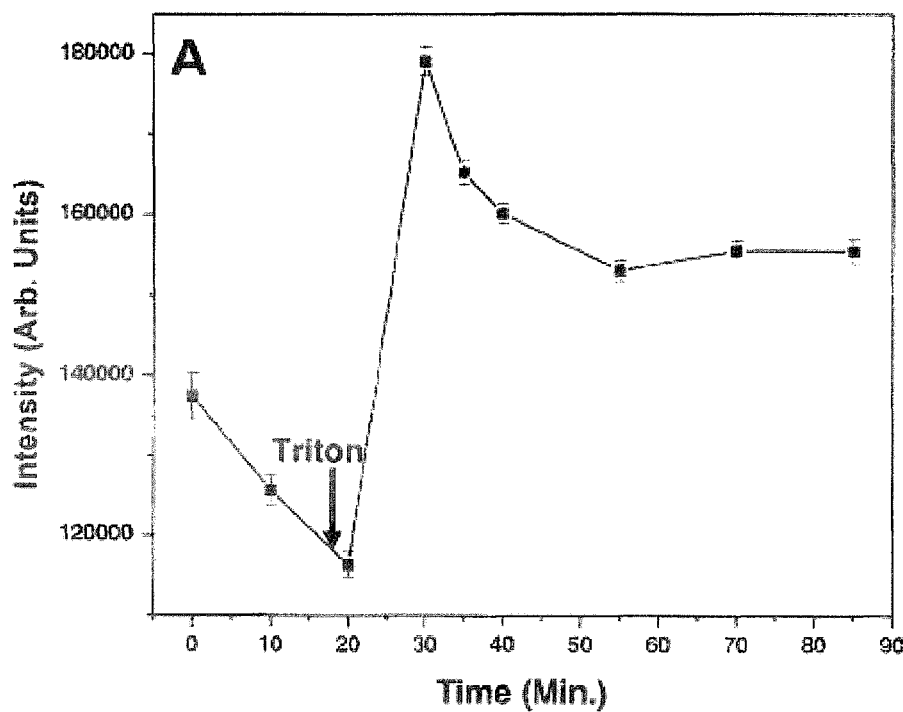
FIGS. 9A-B graphically illustrate release of dye from lipid-bilayer coated beads after exposure to TRITON X-100 detergent (FIG. 9A), and melittin (FIG. 9B).
Figure 9:
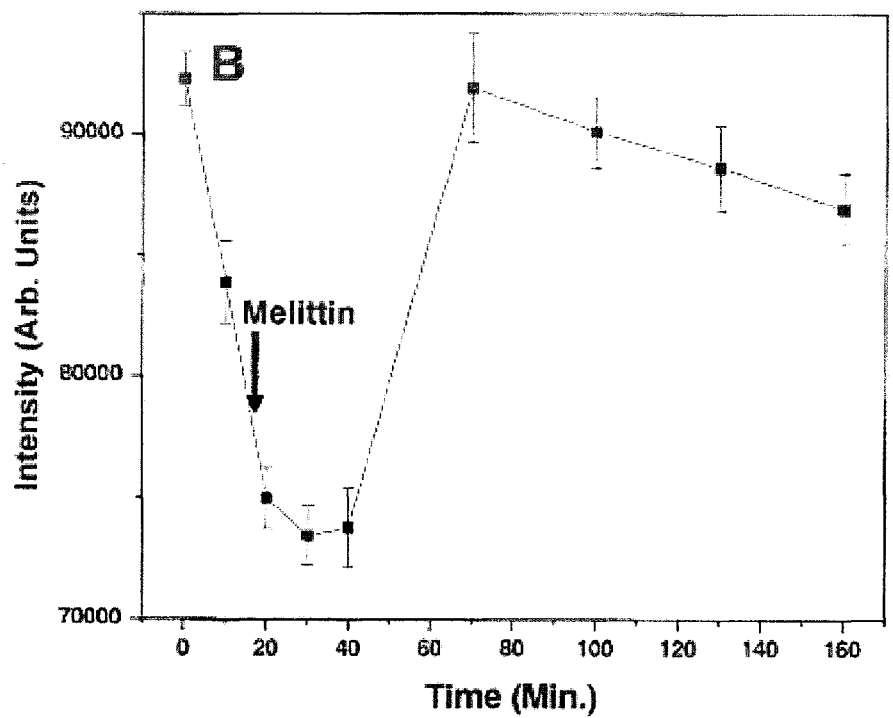

FIG. 9A shows disruption of lipid membranes with TRITON X-100 detergent in the microcolumn system described above. The initial decrease in fluorescence intensity was due to the photo bleaching, resulting from exposure of the fluorescein-biotin segment to the Ar ion laser. To minimize the photo bleaching, the bead segment was scanned only for 30 seconds at 10 min intervals. At 18 min, 10 μL of TRITON X-100 detergent (10% w/v) was injected. The flow rate was about 1.2 μL/min and the dead volume from injection point to the detection point was about 10 μL. As shown in FIG. 8C, the porous beads initially released a large amount of entrapped compound. The release of biotin (10 mM) from porous beads unquenched the fluorescein, which corresponds to the high fluorescence intensity observed at 30 min (FIG. 9A). In the presence of excess biotin, fluorescein-biotin also can be dissociated from streptavidin, thus the decrease in fluorescence intensity after 30 min, may be due to the combined effects from photobleaching and the dissociation of some fluorescein-biotin from streptavidin.

FIG. 9B shows release of biotin (10 mM) as a result of melittin interaction with supported membranes on microbeads in the microcolumn system. 20 μL of melittin (220 μM) was injected to the bead packed microchannel at 18 min. The flow rate was maintained at ~1.2 μL/min. The initial fluorescence intensity decrease is again due to photobleaching, resulting from exposure of the fluorescein-biotin segment to the Ar ion laser. At this point the frequency of laser scanning of the column was decreased from 10 min to 30 min, to prevent excess photobleaching. Because the disruption of bilayers by melittin will create only a slow release as observed in the suspension studies, photobleaching can have a significant effect on the detection of fluorescence intensity. The increase in fluorescence intensity was not as high as that observed for Triton TRITON X-100 detergent, which is in accordance with the results obtained in the suspension studies.

Detection of Membrane Interaction by Fluorescence Superquenching

The feasibility of using superquenching as a method of detecting membrane-toxin interactions in microcolumns was also investigated. The fluorescence intensity of the cationic polyelectrolyte poly(p-phenylene-ethynylene)polymer (PPE) can be super-quenched by the quencher 9,10-anthraquinone-2,6-disulfonic acid (AQS). The exposure of fluorescent PPE-coated beads to the laser caused photobleaching as seen in the first 90 min in FIG. 10A. The absence of quenching of fluorescence intensity after the injection of AQS (120 μM) into the microcolumn indicated that the membranes around the PPE-coated bead were stable. Upon injecting 10 μL of a 1:1 mixture of AQS and melittin (120 μM, 220 μM) at about 110 min, there was a slight rise in fluorescence intensity followed by a significant decrease. It has been observed in flow cytometric studies that formation of DMPG membranes on PPE-coated beads will quench the PPE fluorescence to some extent. The initial rise in fluorescence intensity was probably due to the unquenching of the PPE, due to the removal of lipid bilayers from PPE-coated beads through melittin interaction, whereas the decrease in fluorescence corresponded to superquenching of PPE by AQS after disruption of DMPG bilayer by melittin.

Figure 10:
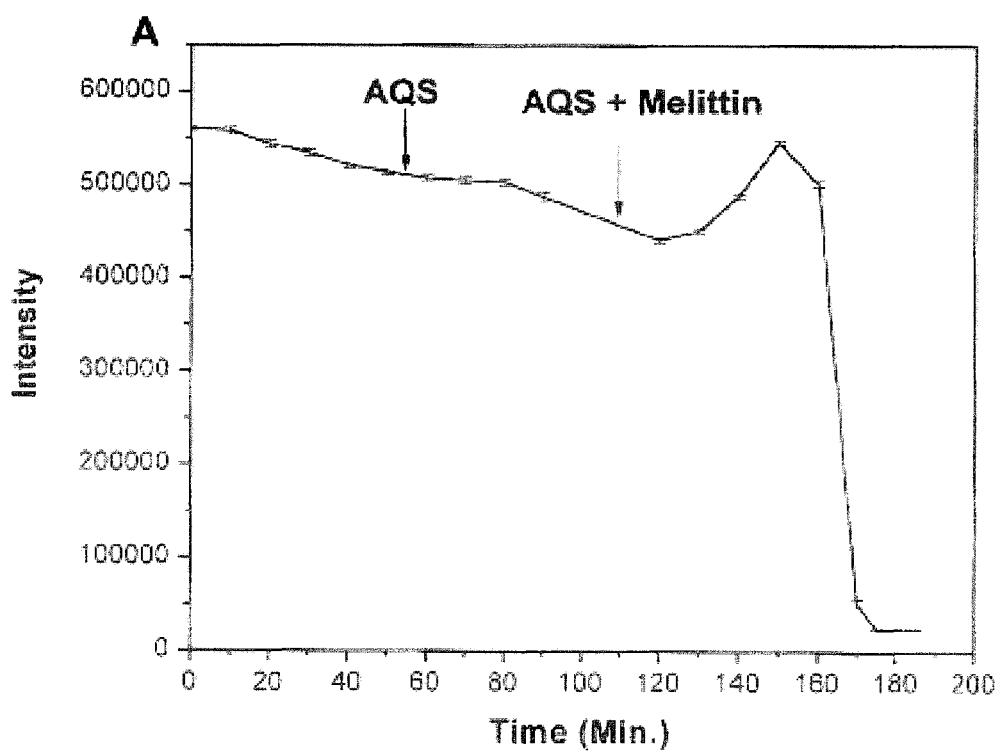
FIGS. 10A-B illustrate membrane interaction analyses by fluorescence superquenching.
Figure 10:
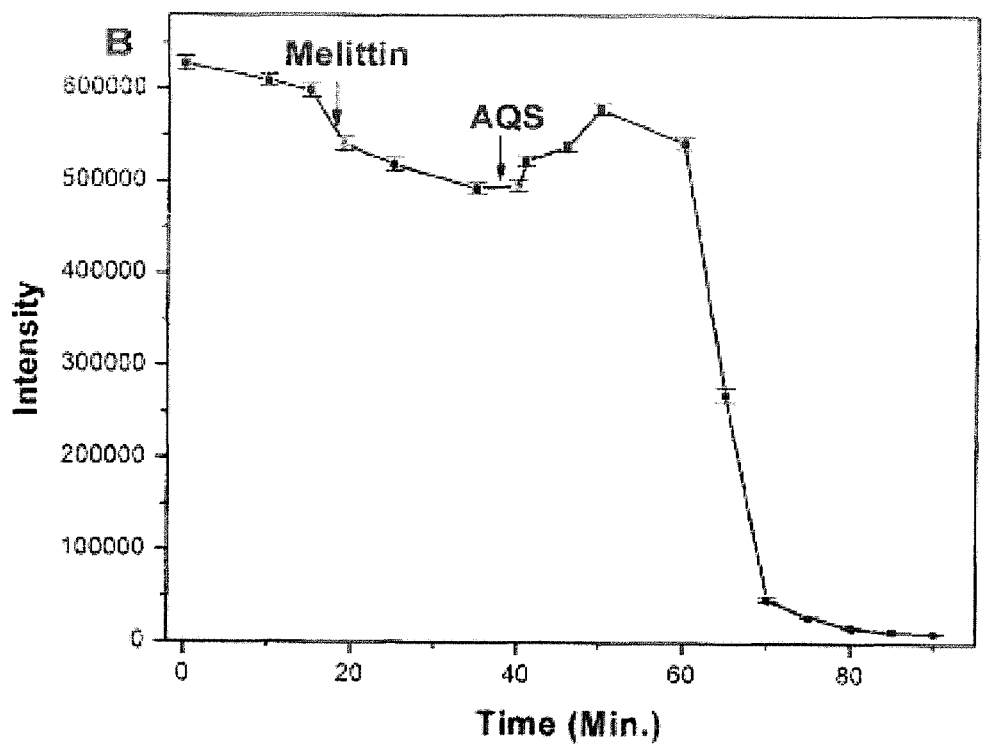

The delayed response time matches the time that reagents take to reach the bead segment in the microchannel from the point of injection. Since melittin is positively charged, whereas AQS is negatively charged, there is a possibility that AQS, but not melittin, is initially repelled by the anionic bilayer, which results in initial interaction of melittin with the bilayer, causing an increase in fluorescence. When the lipid bilayer is disrupted by melittin, AQS can interact with the polymer resulting in superquenching. To verify that the rise was due to melittin, we next injected melittin alone, and after about 20 min AQS was injected, as shown in FIG. 10B. In this case the time delay between the point of sample injection and the packed beads was about 25 min. A rise in fluorescence at about 25 min after injecting melittin was detected, followed by a significant decrease in fluorescence ~25 min after injecting AQS. This suggests that the rise in fluorescence is indeed due to disruption of DMPG bilayer on PPE coated beads as indicated by flow cytometric studies. On the other hand, the dramatic decrease in fluorescence corresponding to superquenching of PPE by AQS shows the usefulness of superquenching technique as a sensitive detection method to study the membrane-toxin interactions in microfluidic devices.

These studies illustrate the feasibility of using lipid coated porous silica beads as a new platform for studies of membrane-detergent and membrane-toxin interactions. Fluorescein dye was successfully encapsulated into porous silica beads by forming a phospholipid bilayer around the beads after the beads were saturated with dye. Membrane interaction studies on supported lipid membranes on porous silica beads were performed using bead suspensions and microcolumns of beads. Membrane interaction with detergents and membrane active peptides in microcolumns was detected as: (i) release of dye (ii) release of reagents and (iii) superquenching of fluorescent polymers. Membrane disruptors tested included TRITON X-100 detergent, α-toxin and melittin. Phospholipid bilayers containing negatively charged lipids were also formed on porous silica beads and these membranes were very stable for a long period of time. These negatively charged phospholipid bilayers on porous silica beads can endure experimental conditions necessary for their incorporation into packed microcolumns while maintaining the bilayer integrity and functionality.

Example 2

Superquenching as a Detector for Microsphere-Based Flow Cytometric Assays

This Example illustrates that superquenching of fluorescent polymers can be used in conjunction with flow cytometry, thus combining the advantages of superquenching with those of flow cytometry. This Example also illustrates the formation and disruption of a supported lipid bilayer in mediating superquenching and how the illustrated procedures can be used in new biosensing applications.

Materials

The cationic polyelectrolyte poly(p-phenylene-ethynylene) derivative (PPE), and the quencher 9,10-anthraquinone-2,6-disulfonic acid (AQS) (see below) were obtained from QTL Biosystems (Santa Fe, N. Mex.) (Kushon et al. Langmuir 18:7245-7249 (2002)). Borosilicate glass microspheres (5 μm diameter) were purchased in dry form from Duke Scientific (Palo Alto, Calif.). A Quantum MESF kit was purchased from Bangs Laboratory, Inc. (Fishers, Ind.). 1,2-dipalmitoyl-sn-glycero-3-phosphatidylcholine (DPPC), egg phosphatidylcholine (egg-PC), and 1,2-dimyristoyl-sn-glycero-3-[phosphor-rac-(1-glycerol)]sodium salt (DMPG) were obtained from Avanti Polar Lipids, Inc (Alabaster, Ala.). Phosphate buffer saline (PBS) and TRITON X-100 detergent were obtained from Sigma (St. Louis, Mo.).

The structure of the cationic polyelectrolyte poly(p-phenylene-ethynylene) derivative (PPE) is shown below.

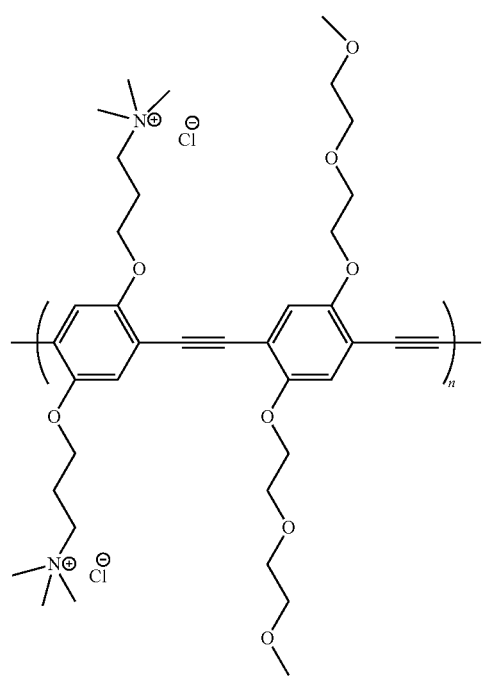

The structure of the quencher 9,10-anthraquinone-2,6-disulfonic acid (AQS) is also shown below.

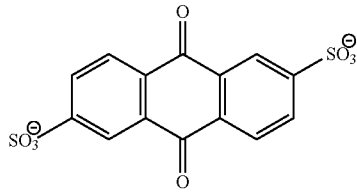

Methods

Coating Borosilicate Microspheres with Polymer.

Cationic PPE has an approximate surface area of 280 square angstroms per polymer repeat unit (PRU). From simple calculations based on using 5 μm diameter beads (assuming a smooth spherical shape), with a density of 1.96 g/mL, and a calculated surface area, it was determined how much polymer was needed to provide monolayer coverage to a given amount of beads. The actual coating solution was used at a level sufficient to provide 1.2 monolayers of PPE per bead. The concentration was determined from the peak absorbance (432 nm) using the measured extinction coefficient of PPE (35,100 L/mol*cm per PRU). The silica beads were suspended in ultrapure water (60 mg dry beads in 1.2 mL water) and stirred rapidly. The calculated amount of polymer solution was added. Coating was essentially instantaneous. However the mixture was allowed to stir at room temperature for 30 minutes. The suspension was centrifuged, and the clear supernatant was decanted and discarded. The PPE-coated microspheres (MS-PPE) were resuspended in water and the washing cycle of centrifuging, decanting and resuspension was repeated four times.

Preparation of Unilamellar Lipid Vesicles.

Small unilamellar vesicles (SUVs) were prepared using a 2 mM solution of DPPC, 1 mM egg-PC, or 2 mM DMPG in chloroform. The lipid was dried by nitrogen gas followed by vacuum. The dried lipid was resuspended in phosphate buffer saline (PBS), pH 7.4, and incubated at 37° C. for 10 min, then sonicated to optical clarity in a sonication bath (Branson Cleaning Equipment Co., Shelton, Conn.).

Preparation of Microsphere-Supported Lipid Bilayers.

Lipid bilayers were assembled on microspheres as previously described (Buranda et al. Langmuir 19:1654-1663 (2003); Bayerl & Bloom, Biophys J 58:357-362 (1990)). Briefly, the small unilamellar vesicles were incubated at 37° C. for 5 min, and PPE-coated microspheres were added to them, and mixed at room temperature using a vortex mixer for 30 min, followed by incubation at 37° C. for 5 min without mixing. The lipid-coated PPE-coated microspheres were washed by suspension in PBS followed by centrifugation, where the clear supernatant was decanted and discarded. The cycle of resuspension, centrifugation, and decanting, was repeated four additional times. Finally, the lipid-coated PPE-coated microspheres were resuspended in PBS.

Disruption of Lipid Bilayers.

Lipid bilayers were disrupted by adding TRITON X-100 detergent to the bead suspension to a final concentration of 0.25% (w/v).

Fluorimetry.

Fluorescence measurements of bead suspensions were performed using a Wallac 1420 Multilabel counter, PerkinElmer (Shelton, Conn.) by excitation at 485 nm and collection of emission at 535 nm using top counting mode. A 96-well plate was used, where 200 μL samples containing either PPE polymer in solution or $1.2 \times 10^6$ PPE-coated microspheres±AQS were analyzed using a counting time of 2 seconds per well.

Fluorescence Microscopy.

$2.5 \times 10^5$ PPE-coated microspheres in 200 μL PBS with and without coating with DMPG were treated with 10 μM quencher, and immediately after preparation, images were taken with an Olympus BH2-RFCA fluorescence microscope (Melville, N.Y.).

Flow Cytometry.

Bead suspensions of $2.5 \times 10^5$ PPE-coated microspheres in 200 μL PBS were analyzed using a FACScan flow cytometer (Becton-Dickinson, Sunnyvale, Calif.) with excitation at 488 nm. Fluorescence signals were acquired on the FL-1 channel (525 nm) using log amplification and analyzed with the CellQuest software.

Results

Coating of Silica Microspheres with PPE.

Figure 11:
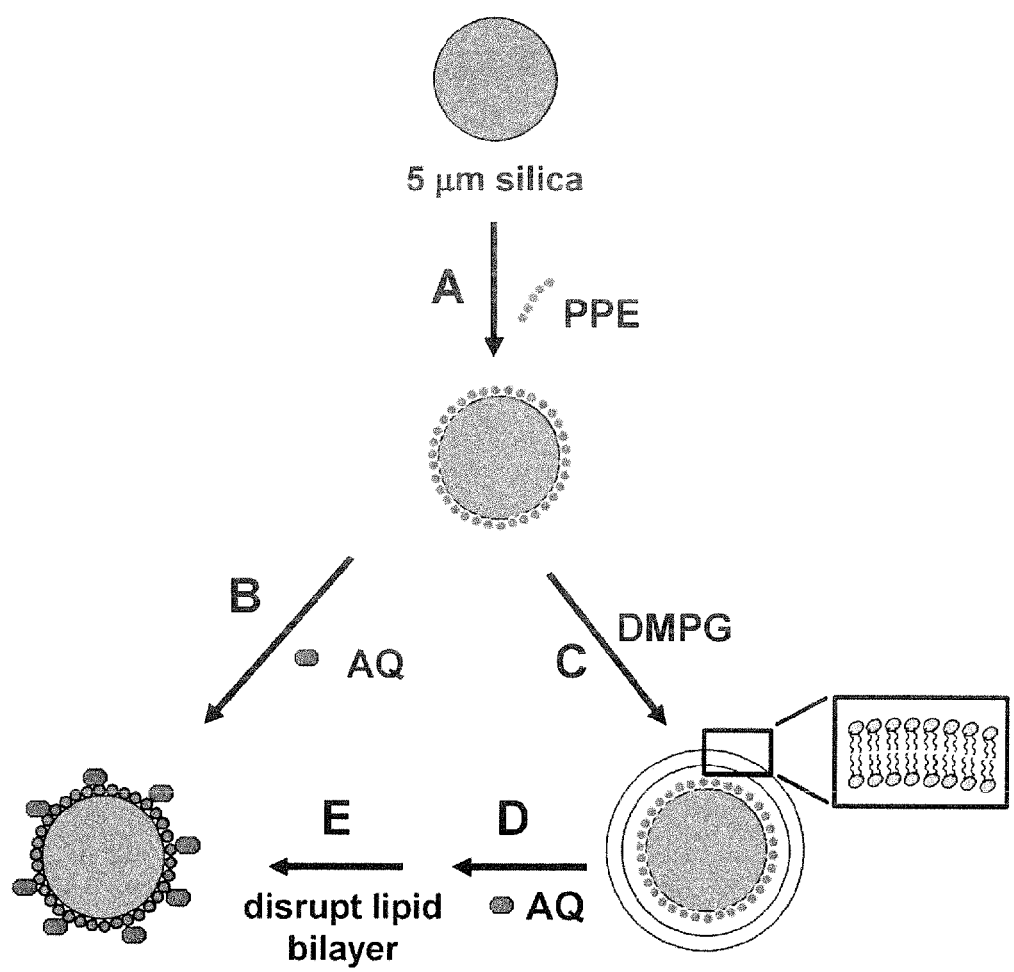
FIG. 11 illustrates the strategy for investigation of superquenching of fluorescent microspheres using flow cytometry. Steps A-E illustrate the procedures that have been and can be used. In step (A) 5 μm silica microspheres were coated with PPE, followed by either step (B), which involves adding the quencher AQS, or step (C), which involves forming a lipid bilayer around the MS-PPE, then step (D) may be performed, which involves adding the quencher AQS, and a test agent or a lipid bilayer disruption agent can be added as depicted for (E) where the lipid bilayer is disrupted.
Figure 12:
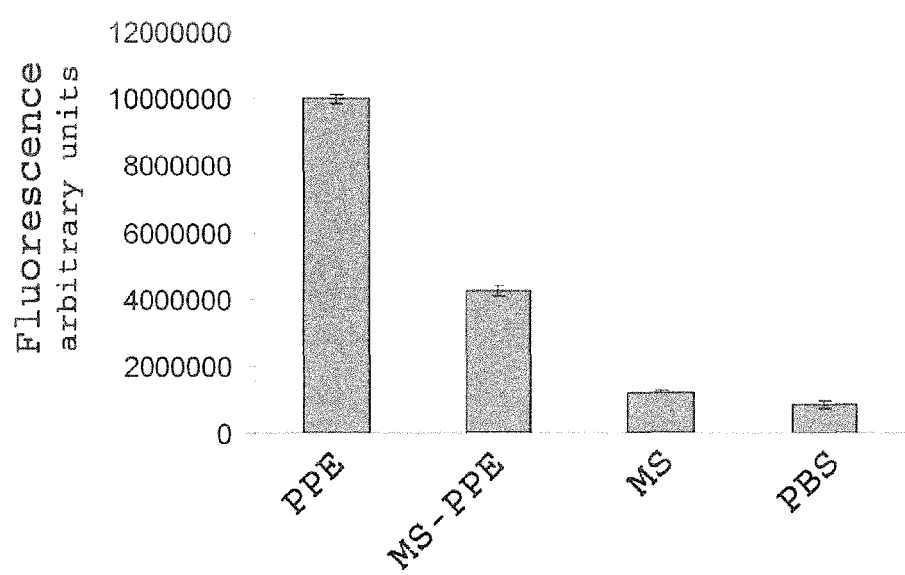
FIG. 12 graphically illustrates that the number of polymer repeat units (PRU) per bead can be estimated by comparing the fluorescence of the PPE-coated microspheres to a known concentration of PPE polymer in solution using fluorimetry. PPE=PPE polymer in solution (4.5 μM), MS-PPE=PPE-coated microspheres ($2.4 \times 10^6$), MS=microspheres without coating ($2.4 \times 10^6$), PBS=phosphate buffer saline.

Silica microspheres (5 μm average diameter) were coated with about 1.2 monolayer of PPE as described above (see also, FIG. 11A). The number of polymer repeat units (PRU) per bead was estimated by comparing the fluorescence of the PPE-coated microspheres to a known concentration of PPE polymer in solution using fluorimetry (FIG. 12). It was determined by fluorimetry that there are about 0.14 fmoles of PRU per PPE-coated microsphere. When examined by flow cytometry, the MS-PPE maintained stable fluorescence for over six months while stored in ultrapure water at room temperature. Next the fluorescence intensity of the MS-PPE was compared by flow cytometry to calibrate microspheres from a Quantum MESF kit. These studies showed that each MS-PPE had a fluorescence intensity equivalent to that of about 38,000±5,000 fluorescein isothiocyanate molecules in solution.

Superquenching of PPE on Silica Microspheres with AQS.

Figure 13:
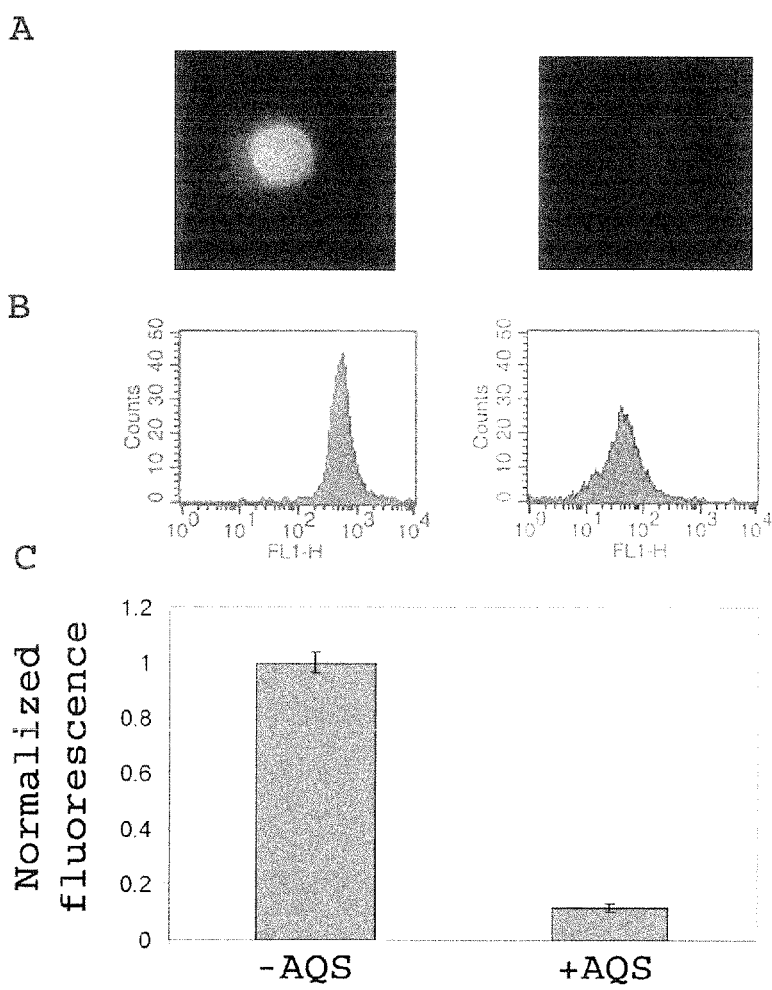
FIGS. 13A-C illustrates detection of $2.5 \times 10^5$ MS-PPE in 200 μL PBS in absence (left panels), and in presence (right panels) of 10 μM of the quencher AQS.

The potential for superquenching of fluorescent polymers during flow cytometry was evaluated as a detection tool. Examination of the bead suspensions under a fluorescence microscope showed that the fluorescence of the MS-PPE was quenched upon addition of AQS (FIG. 13A). FIG. 13B shows the fluorescence intensity distribution histograms of MS-PPE obtained by flow cytometry. Upon treatment with AQS the mean fluorescence intensity decreased dramatically. Normalizing the fluorescence intensities of mean channel fluorescence to that without treatment showed that treatment with AQS lead to a 90% reduction in fluorescence (FIG. 13C).

Figure 14:
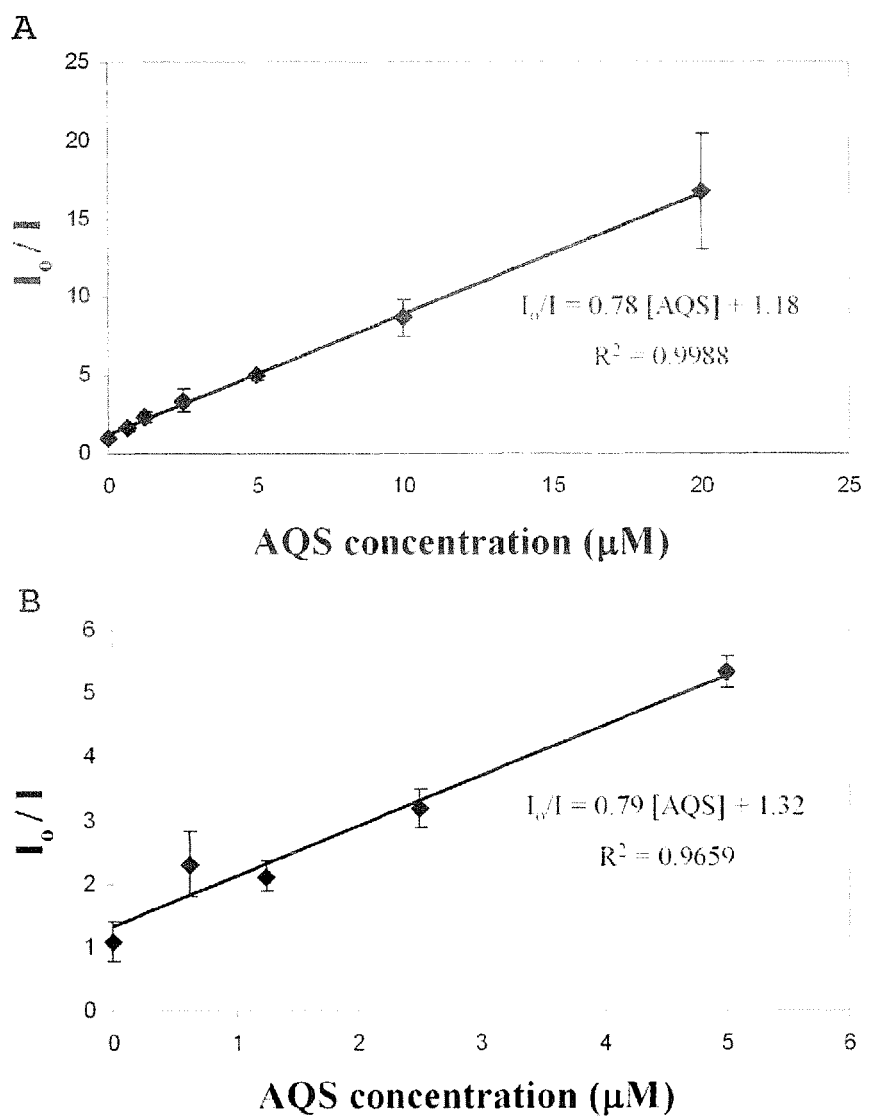
FIGS. 14A-B shows Stern-Volmer plots for quenching of MS-PPE by AQS detected by (A) flow cytometry, and (B) fluorimetry. For flow cytometry, the error bars represent the standard deviation of the ratio of means of the fluorescence intensity histograms obtained for four replicate measurements.
Figure 15:
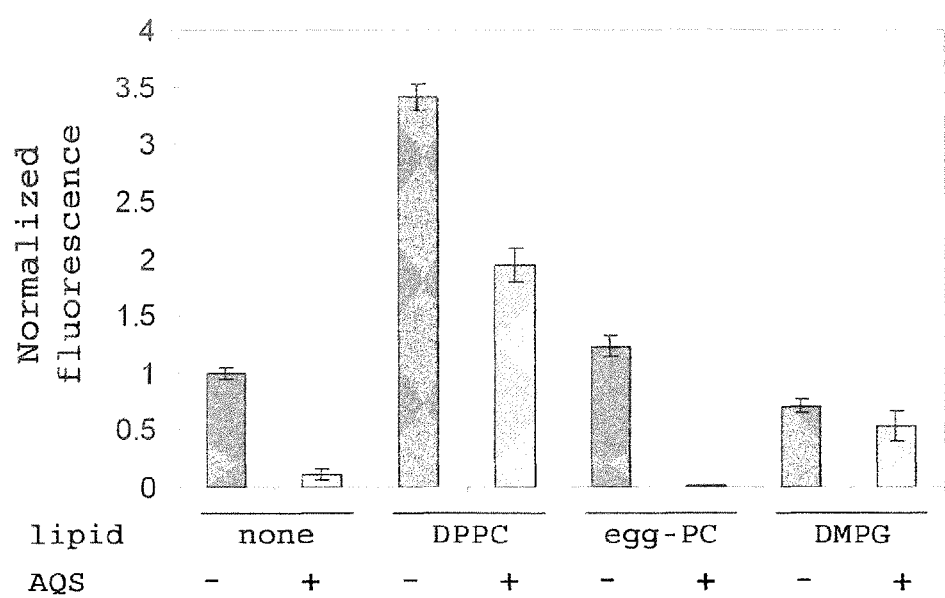
FIG. 15 graphically illustrates flow cytometric evaluations of different lipids that involved formation of supported lipid bilayers on MS-PPE for the purpose of forming a barrier to quenching by AQS. Lipids tested were 2 mM DPPC, 1 mM egg-PC, and 2 mM DMPG. Fluorescence was normalized to that of MS-PPE without lipids and in absence of AQS. −AQS and +AQS refer to absence and presence of 10 μM AQS. The errors bars represent SD of means of normalized histograms obtained for triplicates.
Figure 16:
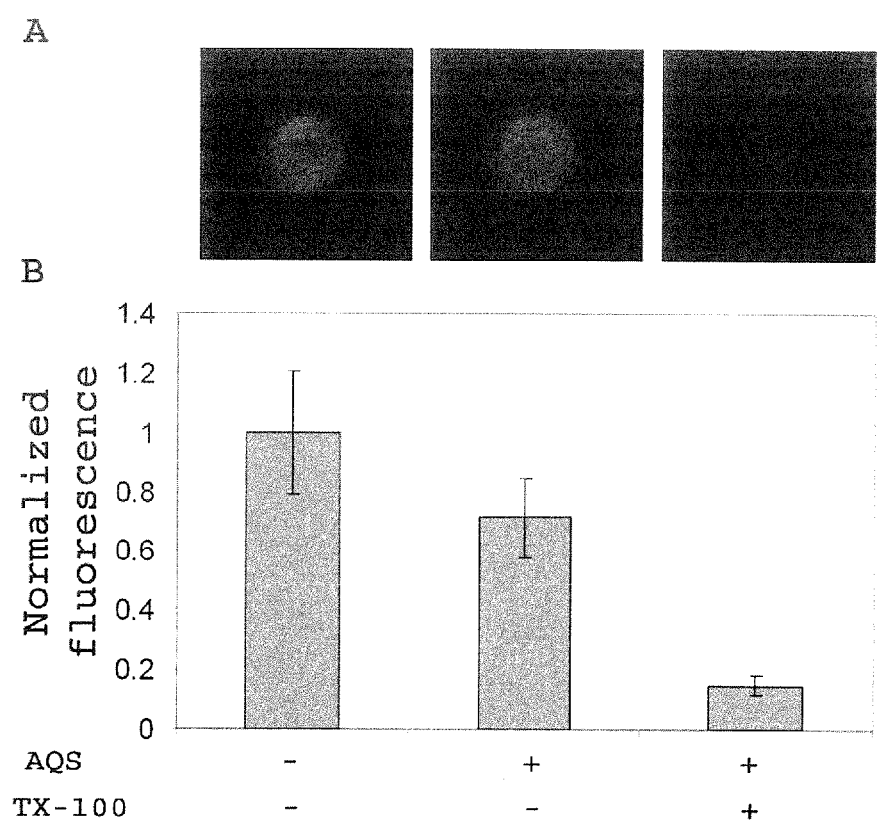
FIGS. 16A-B illustrates the effect of forming and disrupting anionic lipid bilayers around the MS-PPE. $2.5 \times 10^5$ MS-PPE supporting DMPG lipid bilayers in 200 μL PBS were examined in absence (−) and in presence (+) of 10 μM AQS, and with addition of TRITON X-100 detergent (TX-100) to a final concentration of 0.25% (w/v) after adding the quencher by (A) fluorescence microscopy and by (B) flow cytometry. Fluorescence was normalized to that observed for untreated MS-PPE with DMPG lipid bilayers.

The effect of the quencher, AQS, on the fluorescence of MS-PPE was determined by adding different concentrations of AQS and immediately reading the fluorescence by flow cytometry (FIG. 14A) or by fluorimetry (FIG. 14B). Adding AQS to the suspension of MS-PPE decreased the fluorescence emission intensity in an AQS-concentration-dependent manner (FIGS. 14A and B). The quenching of the MS-PPE as detected by both fluorimetry and flow cytometry, could be described by a conventional Stern-Volmer equation:

$$I_o/I = 1 + K_{SV}[Q]$$

where $I_o$ and $I$ represent the fluorescence intensities in the absence and in presence of the AQS, and $K_{SV}$ is the Stern-Volmer quenching constant. However, the fluorimeter was not sensitive enough to detect the lower fluorescence (higher quenching) when AQS was added to MS-PPE at concentrations higher than 5 μM. The values of $K_{SV}$ obtained by flow cytometry and fluorimetry were $0.78 \times 10^6$ $M^{-1}$, and $0.79 \times 10^6$ $M^{-1}$, respectively. The correlation coefficient for the more sensitive flow cytometry was higher than that obtained by fluorimetry. In subsequent experiments, described below, AQS was used at a concentration of 10 μM.

Lipid Bilayers as Barriers to Superquenching.

Molecular assemblies were investigated to ascertain whether they could act as barriers between the fluorescent polymer and quencher, thus mediating superquenching in assays carried out by flow cytometry. Lipid bilayers were chosen as barriers because supported lipid bilayers can be easily formed on microspheres and because they have been used in a variety of biosensing schemes, either in the form of liposomes, or as supported lipid bilayers that incorporate receptors, ion channels, or porins. Additionally, lipid bilayers can be used to either immobilize biomolecules or to incorporate biomolecules to generate biologically relevant environments, useful for analytical testing and screening procedures. Such biologically relevant environments can influence the stability and activity of biomolecules incorporated therein as well as modulating the interactions of biomolecules and test agents.

The feasibility of using the zwitterionic lipids DPPC and egg-PC to form supported lipid bilayers on MS-PPE was assessed (FIG. 15). Coating DPPC onto MS-PPE resulted in a significant increase in the fluorescence from the polymer. Addition of AQS produced an almost 40% reduction of the polymer fluorescence, yet the fluorescence of the DPPC bilayer coated MS-PPE in the presence of the AQS quencher was still almost 10-fold higher than that of MS-PPE and quencher without the lipid. Coating MS-PPE with egg-PC resulted in less modulation of the polymer fluorescence, however addition of AQS caused nearly complete quenching of the polymer fluorescence (~98%) from egg-PC coated MS-PPE. Thus, these zwitterionic lipids did not act as sufficient barriers to superquenching.

The PPE polymer is positively charged. Therefore, PPE might interact more stably with an anionic lipid than with the zwitterionic lipids tested above. The anionic lipid DMPG was used to test this theory by assessing whether it could prevent superquenching of the MS-PPE by AQS. Different concentrations of DMPG liposomes were tested (ranging from 1 to 10 mM). It was found that addition of the anionic lipid led to some attenuation of the fluorescence of MS-PPE. However when using 2 mM DMPG, the modulation of polymer fluorescence was relatively small (FIG. 15). In particular, DMPG produced a lipid bilayer that effectively blocked the quenching of the polymer by 10 μM AQS. Thus, upon addition of quencher to MS-PPE after treatment with DMPG ~70% of fluorescence of the PPE was retained (FIGS. 16A and 16B). Disruption of the lipid bilayer by 0.25% (w/v) TRITON X-100 detergent in the presence of 10 μM AQS (as shown in FIG. 11 by steps C, D and E) resulted in reduction of fluorescence to ~10% of the original fluorescence value (FIGS. 16A and 16B), which is a level that is similar to what was observed in the absence of lipid bilayer (FIG. 15).

These experiments demonstrate that flow cytometry can be used as a sensitive and quantitative method for the detection of superquenching of the fluorescence of MS-PPE. Additionally, these experiments show that DMPG lipid bilayers can protect against superquenching of PPE fluorescence and that disruption of the DMPG lipid bilayer leads to superquenching of PPE fluorescence (as outlined in FIG. 11).

In this Example, a cationic conjugated polyelectrolyte was adsorbed onto anionic silica microspheres. The coated beads exhibited good stability and the coating procedure employed was highly reproducible. After coating the beads to produce MS-PPE, the beads were uniformly fluorescent when observed by fluorescence microscopy exhibited a relatively narrow distribution by cytometry. The Stern-Volmer quenching constant that was measured ($0.8\times10^6$ $M^{-1}$) for the coated MS-PPE system was the same, within experimental error, when measured by simple fluorescence intensity or by flow cytometry. The value is somewhat lower than that measured for some other fluorescent conjugated polyelectrolytes coated onto beads when using energy transfer quenchers, but very comparable to the $K_{SV}$ obtained for a structurally similar polyelectrolyte, cationic poly(p-phenylene-co-thiophene) when quenched by AQS in aqueous solution (Ramey et al. Macromolecules 38: 234-43 (2005)).

Given the versatile structure of conjugated polyelectrolytes, it is reasonable to expect that many possibilities exist for constructing superquenching based assays for use in flow cytometry. For example, employment of surface modified silica would allow for the use of anionic polymers and cationic quenchers. It is also possible that other surface properties could be used to attach either, or both the polymer and related sensor components.

The finding that DMPG interacts with MS-PPE to provide a fluorescent particle that is largely protected against superquenching indicates that this system can be used for membrane disruption assays. As noted above, some of the lipids coated onto MS-PPE do result in modulation of the polymer fluorescence. Modification of the fluorescence of conjugated polyelectrolytes by addition of oppositely charged surfactants in solution has been previously observed. However, in most studies of the polymer in supported formats, relatively little modification of polymer fluorescence is observed.

On the other hand, if the lipid forms an ordered charged or zwitterionic bilayer overcoat of the surface-adsorbed polymer, some modification of the polymer photophysics may occur upon exposure to agents that disrupt such an ordered but charged or zwitterionic bilayer. The neutral phospholipid DPPC enhances polymer fluorescence; while there is significant quenching of the polymer fluorescence upon adding AQS, the reduction of quenching in the presence of the lipid indicates that some protection against superquenching is provided.

In contrast egg-PC provides no protection against superquenching of the polymer by AQS. It may be that egg-PC does not form an intact bilayer over the MS-PPE. The observation that DMPG and DPPC do not fully protect the polymer from quenching by AQS suggests that, even with these lipids, there may be defect zones in the coating that allow access of AQS to the polymer. Nonetheless, the striking increase in quenching that occurs when the DMPG bilayers are exposed to TRITON X-100 detergent suggests that sensitive membrane disruption assays may be developed.

This Example has demonstrated that flow cytometry may be as useful or more useful than fluorimetry when examining superquenching on microspheres. Flow cytometry displayed higher sensitivity and accuracy in detecting fluorescence of MS-PPE in comparison to fluorimetry. Generally, using flow cytometry offers high sensitivity measurements of particle fluorescence. Therefore, several assays based on fluorescence superquenching or unquenching can be adapted for use in flow cytometry applications. Existing assay strategies where the effective concentration of the quencher is increased in the vicinity of the fluorescent polymer upon specific biointeraction, for example by tethering the quencher to a ligand, can be easily adapted for use with flow cytometry. New strategies in which bio specific interactions lead to transport of quenchers across lipid bilayer assembly (e.g., through membrane disruption, opening of a pore or channel, or by change in the membrane permeability) are also amenable to implementation with flow cytometric measurements.

As illustrated in this Example, stable lipid bilayer assemblies are readily generated that are useful in assays for monitoring molecules that disrupt lipid bilayers, or that are wellsuited for integrating transmembrane proteins, including ion channels and drug targets, to perform functional assays for sensor applications, and investigation of molecular interactions.

Example 3

Development of Sensitive Assays for Membrane Biospecific Interactions Based on Fluorescence Superquenching This Example illustrates assays for biospecific interactions of molecules with supported lipid bilayers using fluorescence superquenching. A conjugated cationic polymer was adsorbed to silica microspheres, which were then coated with an anionic lipid bilayer. The lipid bilayer attenuated superquenching by acting as a barrier between the conjugated polymer and its quencher. Biointeractions of the lipid bilayer with a membrane lytic peptide were detected and quantified by superquenching of the conjugated polyelectrolyte in flow cytometric- and microfluidic-bioassays.

Materials

The cationic polyelectrolyte poly(p-phenylene-ethynylene) derivative (PPE), and the quencher 9,10-anthraquinone-2,6-disulfonic acid (AQS) (see Example 2) were obtained from QTL Biosystems (Santa Fe, N. Mex.). Borosilicate glass microspheres (5 μm diameter) were purchased in dry form from Duke Scientific (Palo Alto, Calif.). 1,2-dimyristoyl-sn-glycero-3-[phosphor-rac-(1-glycerol)]sodium salt (DMPG) was obtained from Avanti Polar Lipids, Inc (Alabaster, Ala.). Phosphate buffer saline (PBS), TRITON X-100 detergent, and synthetic and natural melittin were obtained from Sigma (St. Louis, Mo.).

Coating Borosilicate Microspheres with Polymer.

The fluorescent cationic PPE was coated onto borosilicate microspheres using sufficient polymer (based on an estimated molecular area and an extinction coefficient of 35,100 L/mol*cm per polymer repeat unit (PRU)) to provide 1.2 times monolayer coverage. The silica beads were suspended in ultrapure water and stirred at room temperature for 30 minutes. Bead suspensions were separated from the solution by centrifugation and the colorless supernatant was discarded. The PPE-coated microspheres (MS-PPE) were rinsed with ultrapure water by four cycles of rinsing, centrifuging, decanting and resuspension.

Preparation of Unilamellar Lipid Vesicles.

Small unilamellar vesicles (SUVs) were prepared using a 2 mM solution of DMPG in chloroform. The lipid was dried by nitrogen gas followed by vacuum. The dried lipid was resuspended in phosphate buffer saline (PBS), pH 7.4, and incubated at 37° C. for 10 min, then sonicated to optical clarity in a sonication bath (Branson Cleaning Equipment Co., Shelton, Conn.).

Preparation of Microsphere-Supported Lipid Bilayers.

Lipid bilayers were assembled on microspheres as previously described. Briefly, the small unilamellar vesicles were incubated at 37° C. for 5 min, the MS-PPE were added and this combination was mixed at room temperature using a vortex mixer for 30 min, followed by incubation at 37° C. for 5 min without mixing. The lipid-coated MS-PPE were washed by suspension in PBS followed by centrifugation, and the clear supernatant was decanted and discarded. The cycle of resuspension, centrifugation, and decanting, was repeated four additional times. Then, the lipid-coated MS-PPE were resuspended in PBS.

Flow Cytometry.

Bead suspensions of $2.5 \times 10^5$ DMPG-coated MS-PPE in 200 μL of PBS were analyzed using a FACScan flow cytometer (Becton-Dickinson, Sunnyvale, Calif.) with excitation at 488 nm. Fluorescence signals were acquired on FL-1 channel (525 nm) using log amplification and analyzed with the CellQuest software. Kinetic analysis of disruption of supported lipid bilayer by melittin was performed by acquiring real-time data with continuous mixing of samples ($10^6$ MS-PPE in 800 μl of PBS) using a magnetic stirrer. The raw data were analyzed using IDL Query software developed by Bruce Edwards (Cancer Center, University of New Mexico, Albuquerque, N. Mex.).

Fluorimetry.

Fluorescence measurements of bead suspensions were performed using a Wallac 1420 Multilabel counter, PerkinElmer (Shelton, Conn.) by excitation at 485 nm and collection of emission at 535 nm using top counting mode. A 96-well plate was used, where 200 μL samples containing either PPE polymer in solution or MS-PPE±AQS were analyzed using a counting time of 2 seconds per well.

Fabrication of Microchannels.

PDMS microchannels were constructed using soft lithographic techniques basically as described in Duffy et al. (*Anal. Chem.* 70: 4974-4984 (1998)) with adaptations. The microfluidic channels were fabricated with weirs to hold the beads in place as described in Piyasena (*Anal. Chem.* 76, 6266-6273 (2004)). The dimensions of the microchannel were: length 2 cm, width 250 μm, and height 60-70 μm. In order to trap beads near the outlet, the depth of the channel was limited to 12-15 μm. The prepared channel was irreversibly sealed on to a glass slide using an Ar plasma.

Packing of Microchannels with MS-PPE.

Microchannels were packed with DMPG coated MS-PPE. 5 μL aliquots bead solutions were injected into the column by applying a vacuum at the outlet. The length of the bead segment was about 5 mm. Bead-packed channels were kept wet with TRIS buffer (100 mM Tris, pH 7.5, 150 mM NaCl) that was allowed to continuously percolate through the column under gravity until ready for use.

Disruption Assays in Microchannels.

The bead packed microchannel was mounted onto a motorized vertical translational stage located in the sample holder space of a Model Fluorolog-3 SPEX fluorometer (Instruments S.A.; NJ). The bead segment was irradiated with 488 nm laser excitation. The inlet of the column was connected to a buffer reservoir, while the outlet was connected to a vacuum source. Several microliters of TRIS buffer were passed through the microchannel before the injection of the sample. While applying the vacuum at the outlet, 10 μL of 120 mM quencher was injected directly into the column through the inlet silicone tubing using a 10 μL Hamilton syringe. After 55 minutes, 10 μL of, 1:1 mixture of 309 μM melittin and 120 μM Quencher was injected. The interactions of the melittin and quencher were monitored as the change in the original intensity of fluorescence signal of PPE coated beads at 520 nm.

Results

Stern-Volmer Quenching Constants by AQS for Free PPE and MS-PPE.

Silica microspheres (5 μm average diameter) were coated with ~1.2 monolayer of PPE, which was equivalent to 0.14 fmole of polymer repeat unit (PRU) per MS-PPE as determined previously by fluorimetry. In order to compare the Stern-Volmer constant ($K_{SV}$) for PPE polymer in solution to that of MS-PPE, fluorescence was determined, by fluorimetry, after adding AQS at different concentrations to $9 \times 10^5$ fmoles PPE in solution, or to its equivalent of MS-PPE suspension (6.4×10⁶ MS-PPE). The quenching of both PPE and MS-PPE followed a conventional Stern-Volmer equation:

$$I_o/I = 1 + K_{SV}[Q]$$

where $I_o$ and $I$ represent the fluorescence intensities in the absence and in presence of the AQS. However, the adsorption of PPE to the microspheres led to a higher $K_{SV}$. The $K_{SV}$ obtained for PPE in solution was $0.29 \times 10^6$ M$^{-1}$, whereas for MS-PPE it was $0.81 \times 10^6$ M$^{-1}$. This finding is consistent with other reports of enhanced superquenching of conjugated polymers when collected on nano- and micro-particles (Jones et al. *Proc. Nall. Acad. Sci. USA* 2001, 98, 14769-14772 (2001)). The increased $K_{SV}$ of PPE-MS indicates higher sensitivity in detection over PPE in solution. The $K_{SV}$ values for PPE and MS-PPE are lower than that of other fluorescent conjugated polyelectrolytes on beads with energy transfer quenchers, but are very comparable to the $K_{SV}$ obtained for a structurally related polyelectrolyte, cationic poly(p-phenylene-co-thiophene), when quenched by AQS in aqueous solution (Ramey et al., *Macromolecules* 38, 234-243 (2005)).

Superquenching in a Flow Cytometric Assay for Biointeraction of Melittin with Microsphere-Supported Lipid Bilayer.

The previous Examples demonstrated that flow cytometry can be used as a sensitive and quantitative method for the detection of superquenching of the fluorescence of MS-PPE. The previous Examples also demonstrated that formation of lipid bilayers around MS-PPE could attenuate superquenching in assays carried out by flow cytometry. Evaluation of different lipids led to the selection of DMPG as the lipid of choice for mediating the quenching of MS-PPE, where it blocked the quenching of MS-PPE by 10 µM AQS. Disrupting the DMPG lipid bilayer by adding 0.25% (w/v) TRITON X-100 detergent in the presence of 10 µM AQS results in reduction of fluorescence to a level comparable to that obtained in absence of a lipid bilayer, which corresponds to ~18% of the fluorescence of DMPG-coated MS-PPE in the absence of quencher.

To assess the potential of using superquenching as a detector in assays for biospecific interactions with lipid bilayers, superquenching of MS-PPE was adapted for detecting disruption of a supported lipid bilayer by melittin. Melittin (MLT) is a bee venom cationic membrane-lytic peptide whose interaction with a lipid bilayer is dependent on the peptide concentration and the lipid composition of the bilayer (Bechinger, B. Crit. Rev. *Plant Sci.* 23, 271-292 (2004)). MLT usually forms pores in zwitterionic lipid vesicles (Ladokhin et al., *Biophys. J.* 72, 1762-1766 (1997)), whereas with anionic lipid vesicles it exhibits a detergent-like action in disrupting the lipid bilayer (Ladokhin & White, S. H. *Biochim. Biophys. Acta* 1514, 253-260 (2001)).

Figure 17A:
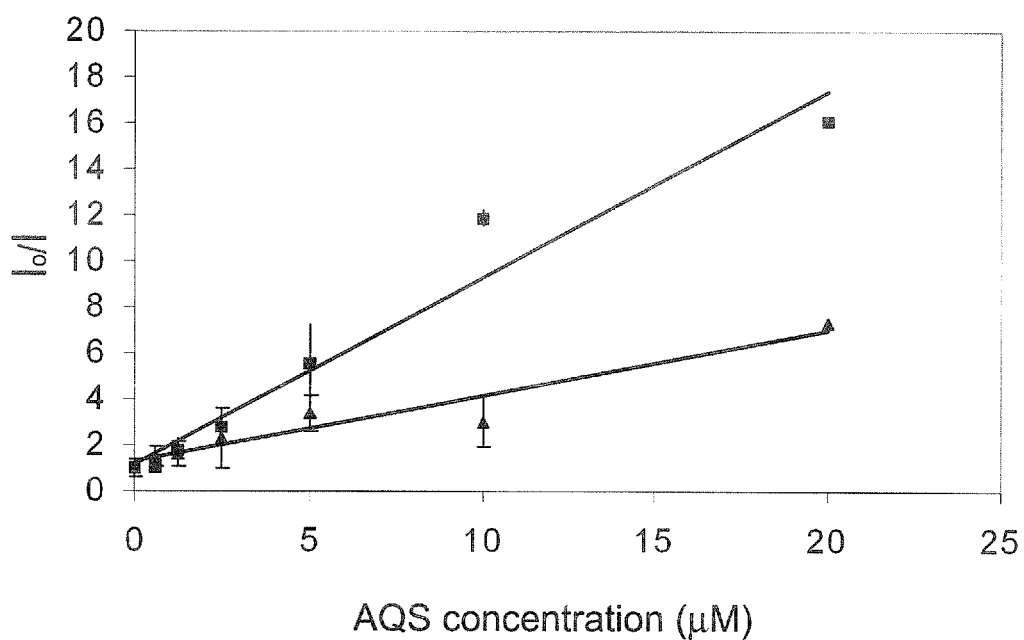
FIGS. 17A-C illustrate superquenching as a result of disruption of lipid bilayer with MLT.
Figure 17:
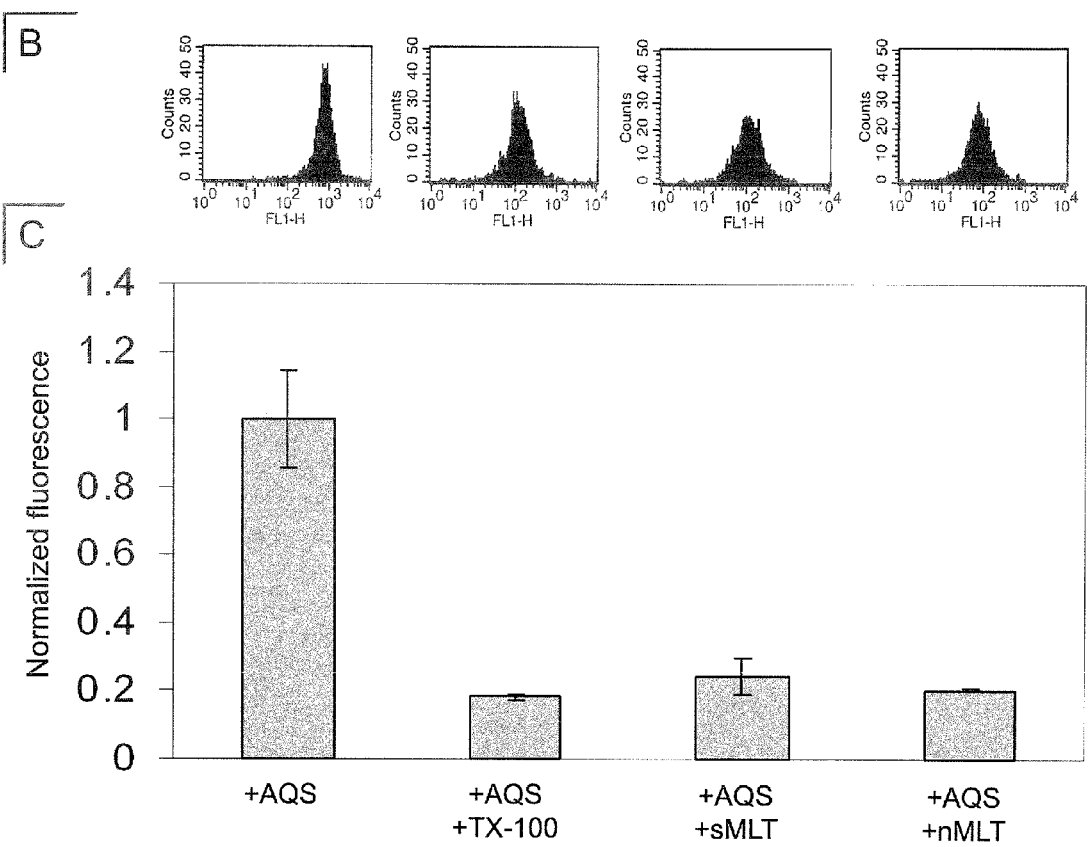

Because an anionic lipid was used to form a lipid bilayer around MS-PPE, it was expected that MLT will disrupt the DMPG lipid bilayer by such a detergent-like action. This was tested by adding 10 µM AQS to DMPG-coated MS-PPE followed by treatment with one of the following: TRITON X-100 detergent, synthetic MLT (sMLT), or natural MLT (nMLT) and immediately reading the fluorescence by flow cytometry. FIG. 17B shows the fluorescence intensity distribution histograms obtained by flow cytometry for the DMPG-coated MS-PPE with the different treatments. These histograms resemble the ones reported previously for MS-PPE, without a lipid coating, in absence and in presence of AQS. FIG. 17C shows that adding either sMLT or nMLT resulted in quenching of the MS-PPE to a level comparable to that occurring on addition of TRITON X-100 detergent, but at very low concentrations of sMLT or nMLT. These results confirm that addition of small amounts of MLT may lead to anionic lipid bilayer disruption.

Figure 18:
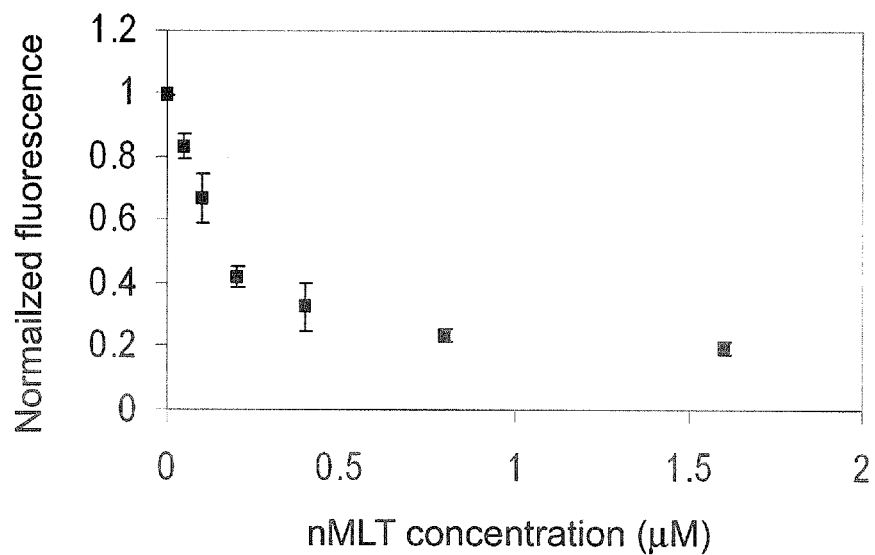
FIGS. 18A-B show binding curves for MLT-disruption of supported lipid bilayer by natural MLT (nMLT.
Figure 18:
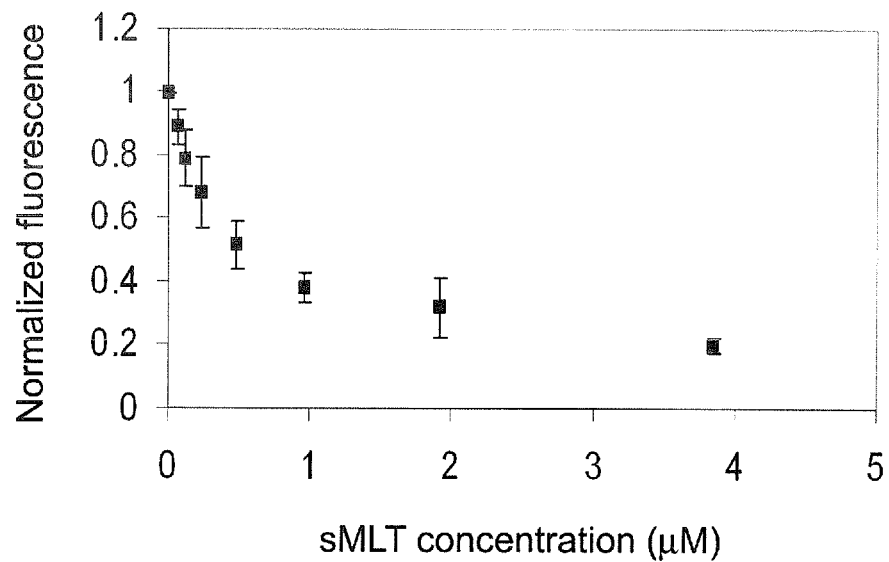

Experiments were performed to demonstrate the use of superquenching in flow cytometric assays for establishing the binding curves of sMLT and nMLT to DMPG supported on MS-PPE (FIG. 18). From FIG. 18, the association constant (corresponding to the reciprocal of the point of half saturation) for nMLT and sMLT with DMPG were $5 \times 10^6$ M$^{-1}$ and $1.7 \times 10^6$ M$^{-1}$, respectively. These association constants are comparable to the association constant of $2 \times 10^6$ M$^{-1}$ reported for association of sMLT with immobilized anionic DMPG membranes using surface plasmon resonance (Lee et al., *J. Peptide Res.* 58, 464-476 (2001)). Lower concentrations of nMLT, in comparison to sMLT, were required to disrupt the DMPG lipid bilayer. This might be attributed to the fact that nMLT contains some phospholipase $A_2$ (PLA$_2$) as a contaminant. PLA$_2$ has a high affinity for anionic phospholipids, with an association constant of $0.5 \times 10^{10}$ M$^{-1}$ (Kim et al., *Anal. Chem.* 250, 109-116 (1997)), which is about 3000 fold higher than that of MLT. Although PLA$_2$ activity requires calcium, which is not present in the experimental system, it has been reported that even upon addition of EDTA to natural MLT, PLA$_2$ maintains its activity, probably due to formation of a tight complex with calcium with PLA$_2$ (Dempsey, C. E. *Biochim. Biophys. Acta* 1990, 1031, 143-161). Thus, the results suggest that the small amount of PLA$_2$ present with nMLT is participating in bilayer disruption.

Existing assays for MLT that employ anionic unilamellar vesicles and conventional quenchers detect MLT lytic activity at concentration ranging from 35 to 140 µM (Ladokhin & White, *Biochim. Biophys. Acta* 1514, 253-260 (2001); Constantinescu & Lafleur, *Biochim. Biophys. Acta* 1667, 26-37 (2004)), and in one study incubating with MLT was for 20 hr (Ladokhin & White (2001)). In this Example, the increased sensitivity as a result of using superquenching and the use of flow cytometry improved the sensitivity for detecting MLT lysis of lipid bilayer at lower concentrations than reported in the literature and without the need for incubating MLT with the membranes.

Figure 19:
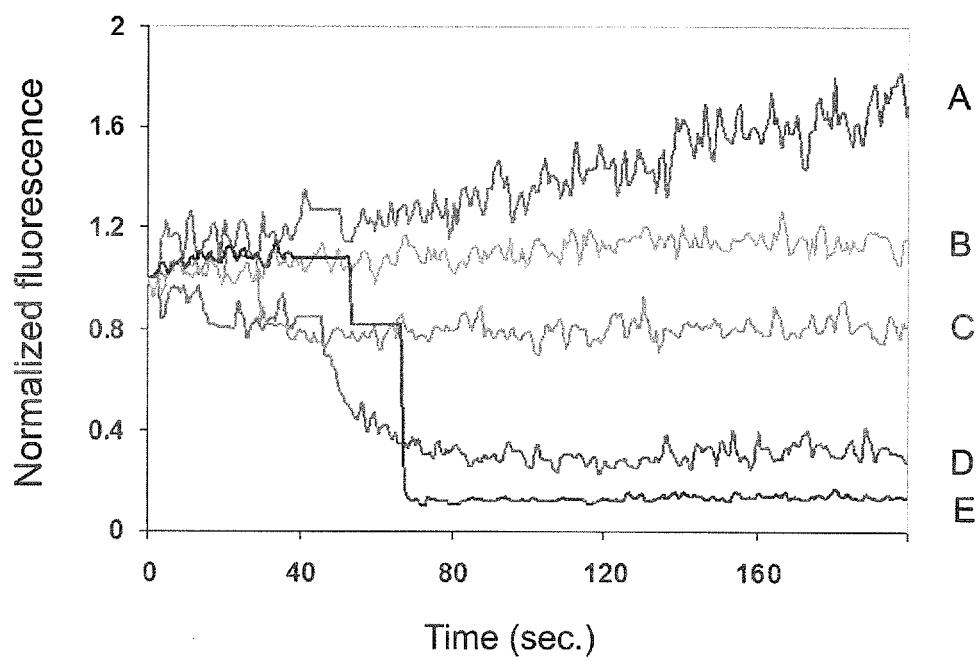
FIG. 19 illustrates the kinetics of supported lipid bilayer disruption by MLT as analyzed by flow cytometry. Trace A illustrates treatment of $2.5\times10^5$ DMPG-coated MS-PPE in 200 µL PBS with synthetic MLT in the absence of AQS. Trace B shows DMPG-coated MS-PPE in absence of AQS and without any other treatment. Trace C shows DMPG-coated MS-PPE after addition of AQS. Trace D shows DMPG-coated MS-PPE with AQS after addition of sMLT. Trace E shows DMPG-coated MS-PPE with AQS after addition of TRITON X-100 detergent.

The kinetics of disruption of supported lipid bilayer by MLT were monitored by measuring real-time changes in fluorescence intensity by flow cytometry (FIG. 19). Suspensions of 10⁶ DMPG-coated MS-PPE in 800 µL of PBS were treated with AQS at a final concentration of 10 µM, then with either sMLT, TRITON X-100 detergent, or no treatment. Trace B in FIG. 19, which displays a constant normalized fluorescence represents the control that is obtained for DMPG-coated MS-PPE in absence of AQS and without any treatments. Treatment with sMLT in the absence of AQS led to an increase in normalized fluorescence (FIG. 19, trace A). This can be attributed to disruption of the lipid bilayer by sMLT, and is consistent with a reversal of the slight quenching of fluorescence caused by the formation of a DMPG lipid bilayer over MS-PPE. Addition of AQS alone to DMPG-coated MS-PPE (FIG. 19, trace C) led to a 20% reduction in fluorescence as reported earlier. Addition of TRITON X-100 detergent to DMPG-coated MS-PPE after the addition of AQS (first dip in trace E, FIG. 19) caused immediate decrease in fluorescence to ~10% of its original value (second dip in trace E, FIG. 19). In contrast, addition of sMLT, after the addition of AQS, (FIG. 19, trace D) led to a gradual reduction of fluorescence intensity to ~20% of the original value. Although MLT forms dimers at high concentrations (Dempsey, C. E. *Biochim. Biophys. Acta* 1990, 1031, 143-161), it is monomeric at the concentrations used in this study. On the other hand, TRITON X-100 detergent forms micelles at the concentration used in this study. This suggests that the much lower concentration of sMLT disrupts the bilayer by a slower action and perhaps different mechanism than that produced by TRITON X-100 detergent.

Detection of Lipid Bilayer Disruption by MLT in a Microfluidic Assay by Superquenching.

Figure 20:
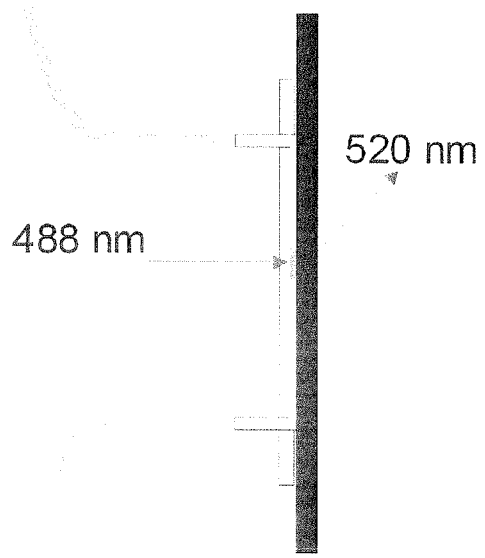
FIGS. 20A-B illustrates detection of MLT biointeraction with supported DMPG in a microfluidic channel.
Figure 20:
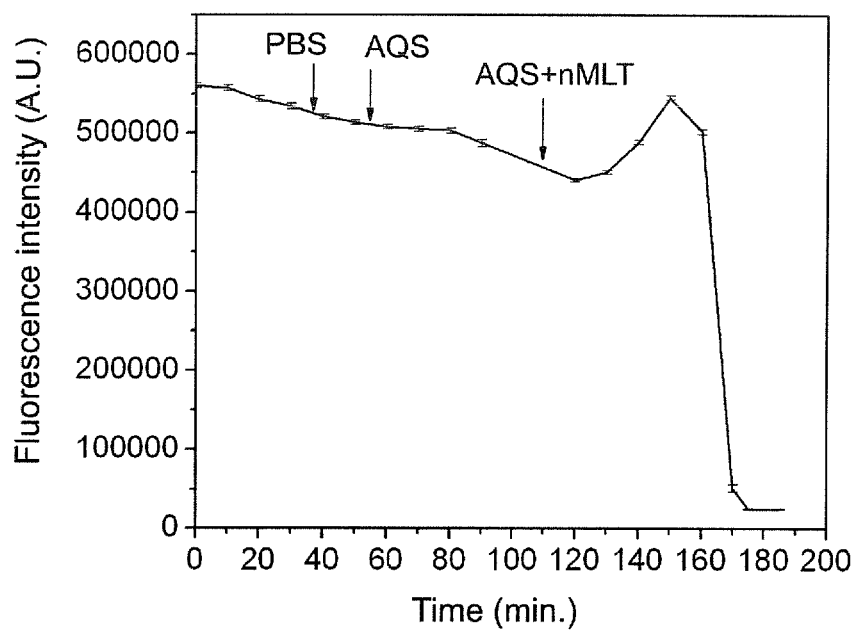
Figure 21:
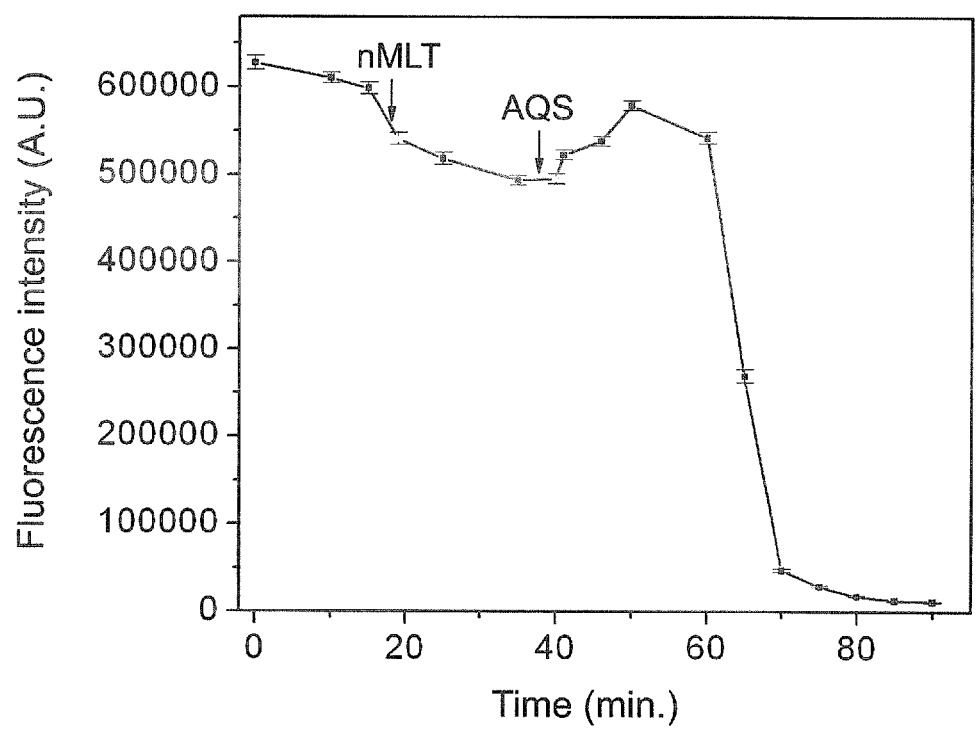
FIG. 21 illustrates the effect of MLT and AQS on MS-PPE in microfluidic channel. Concentrations of injected nMLT and AQS were 309 µM and 120 µM, respectively. Fluorescence intensity is measured in arbitrary units. The arrows indicate injections. The time delay between the point of sample injection and the packed beads was ~25 min.

Biomolecular assemblies on microspheres have been used to develop new microfluidic-based bioassay techniques. The feasibility of using the superquenching technique as a method of detection in microfluidic bioassays was examined in this Example. The setup used is shown in FIG. 20A. The continuous exposure of fluorescent MS-PPE segment to the laser can cause slight photobleaching as was seen in the first 90 min in FIG. 20B. Injection of AQS into the microchannel resulted in a decrease of the fluorescence intensity, which corresponds to the change in the slope, between 90 and 120 min, in FIG. 20B. This decrease in fluorescence is consistent with that observed by flow cytometry (FIG. 19, trace C). The delayed response time (~38 min) matches the time that AQS takes to reach the bead segment in the microchannel from the point of injection. The response time is injection point dependent and can be further decreased by injecting the samples at a point that is closer to the bead column. Upon adding AQS along with nMLT, after ~40 min, there is a slight rise in fluorescence intensity followed by a significant decrease. The initial rise in fluorescence intensity is probably due to disruption of the lipid bilayer by nMLT, similar to the flow cytometric observation as in FIG. 19, trace A; whereas the decrease in fluorescence corresponds to superquenching of MS-PPE by AQS after disruption of DMPG bilayer by nMLT. There is no difference in the diffusion rates of MLT and AQS. However, since MLT is positively charged, whereas AQS is negatively charged, there is a possibility that AQS, but not MLT, is initially repelled by the anionic bilayer, which results in initial interaction of MLT with the bilayer causing an increase in fluorescence. When the lipid bilayer was disrupted as a result of this interaction, AQS can interact with the polymer resulting in superquenching. On the other hand, the rise in fluorescence before the decrease is perhaps due to the fact that the increase may come slowly and before the bilayer has been totally removed. To verify that the rise was due to MLT, nMLT was injected alone, and after ~20 min AQS was injected, as shown in FIG. 21. In this case the time delay between the point of sample injection and the packed beads was ~25 min. A rise in fluorescence ~25 min was detected after injecting nMLT, followed by a significant decrease in fluorescence ~25 min after injecting AQS. This suggests that the rise in fluorescence is indeed due to disruption of DMPG bilayer on MS-PPE as seen in FIG. 19, trace A. On the other hand, the significant decrease in fluorescence corresponding to superquenching of MS-PPE by AQS indicates the utility of superquenching as a detector of biointeractions in microfluidic channels.

This study established the use of superquenching of fluorescent conjugated polyelectrolytes to detect biospecific interactions of a cationic peptide with a lipid bilayer supported on silica microspheres in flow cytometry, and in microfluidic channels. It also suggests a fairly general assay platform for detecting activity of small or large biomolecules that may disrupt or damage lipid bilayer membranes, in addition to lipid enzymes.

Existing methods for studying binding of membrane-active peptides or polypeptides usually employ either unilamellar vesicles in suspension or immobilized in chromatography columns, or supported lipid mono- or bilayers. Such methods can be time-consuming, and may require long incubation times, or the use of high concentrations of peptide/polypeptide. On the other hand, the present invention utilizes the enhanced sensitivity of superquenching in addition to microsphere-based assays with either flow cytometry or microfluidic channels for determining activity of a membrane-lytic peptide. The advantages of these techniques include increased sensitivity by flow cytometry, and the lower consumption of reagents in microfluidic channels. In addition, both techniques have the potential for use in high throughput screening.

This study indicated that biospecific interactions between membrane disrupting peptides (e.g., MLT) and a lipid bilayer reverse the inhibition of AQS quenching of the MS-PPE and thus either destroy the bilayer or otherwise allow the AQS to be transported across the lipid bilayer assembly, thereby bringing AQS to the proximity of the fluorescent polymer. These results also show that this system is compatible with flow cytometry and microfluidic assays. The approach is applicable to integral membrane proteins, including channel- and pore-forming proteins, and drug targets in lipid bilayer assemblies. The Examples illustrate that functional assays for sensor applications, lipid enzymology, and investigations of molecular interactions can readily be developed.

REFERENCES

1. Kohler A, Wilson J. Phosphorescence and spin-dependent exciton formation in conjugated polymers. Organic Electronics 2003; 4:179-189.
2. Grage M M-L, Wood P W, Ruseckas A, Pullerits T, Mitchell W, Burn P L, Samuel I D W, Sundstrom V J. Conformational disorder and energy migration in MEH-PPV with partially broken conjugation. Chem Phys 2003; 118:7644-7650.
3. Collison C J, Rothberg L J, Treemaneekarn V, Li Y. Conformational effects on the photophysics of conjugated polymers: A two species model for MEH-PPV spectroscopy and dynamics. Macromolecules 2001; 34:2346-2352.
4. Jenekhe S A. Excited-state complexes of conjugated polymers. Adv Mater 1995; 7:309-311.
5. Ding L, Egbe D A M, Karasz F E. Photophysical and optoelectronic properties of green-emitting alkoxy-substituted PE/PV hybrid conjugated polymers. Macromolecules 2004; 37:6124-6131.
6. Sandee A J, Williams C K, Evans N R, Davies J E, Boothby C E, Koehler A, Friend R H, Holmes A B J. Solution-processable conjugated electrophosphorescent polymers. Am Chem Soc 2004; 126:7041-7048.
7. Haskins-Glusac K, Pinto M R, Tan C, Schanze K S. Luminescence quenching of a phosphorescent conjugated polyelectrolyte. J Am Chem Soc 2004; 126:14964-14971.
8. Zhou Q, Swager T M J. Fluorescent chemosensors based on energy migration in conjugated polymers: The molecular wire approach to increased sensitivity. Am Chem Soc 1995; 117:12593-12602.
9. Chen L, McBranch D W, Wang H-L, Helgeson R, Wudl F, Whitten D G. Highly sensitive biological and chemical sensors based on reversible fluorescence quenching in a conjugated polymer Proc Natl Acad Sci USA 1999; 96:12287-12292.
10. Chen L, McBranch D W, Wang R, Whitten D. Surfactant-induced modification of quenching of conjugated polymer fluorescence by electron acceptors: applications for chemical sensing. Chem Phys Lett 2000; 330:27-33.
11. Chen L, Xu S, McBranch D, Whitten D. Tuning the properties of conjugated polyelectrolytes through surfactant complexation. J Am Chem Soc 2000; 122:9302-9303.

12. Harrison B S, Ramey M B, Reynolds J R, Schanze K S. Amplified fluorescence quenching in a poly(p-phenylene)-based cationic polyelectrolyte. J Am Chem Soc 2000; 122: 8561-8562.
13. Wang J, Wang D, Miller E K, Moses D, Bazan G C, Heeger A J. Photoluminescence of water-soluble conjugated polymers: Origin of enhanced quenching by charge transfer. Macromolecules 2000; 33:5153-5158.
14. Tan C, Pinto M R, Schanze K. Photophysics, aggregation and amplified quenching of a water-soluble poly(phenylene ethynylene). Chem Commun 2002; 5:446-447.
15. List E W J, Creely C, Leising G, Schulte N, Schlueter A, Scherf U, Muellen K, Graupner W. Excitation energy migration in highly emissive semiconducting polymers. Chem Phys Lett 2000; 325:132-138.
16. Gaylord B S, Wang S, Heeger A J, Bazan G C. Water-soluble conjugated oligomers: Effect of chain length and aggregation on photoluminescence-quenching efficiencies. J Am Chem Soc 2001; 123:6417-6418.
17. Lu L, Helgeson R, Jones R M, McBranch D, Whitten D. Superquenching in cyanine pendant poly(L-lysine) dyes: Dependence on molecular weight, solvent, and aggregation. J Am Chem Soc 2002; 124:483-488.
18. Jones R M, Lu L, Helgeson R, Bergstedt T S, McBranch D W, Whitten D G. Building highly sensitive dye assemblies for biosensing from molecular blocks. Proc Natl Acad Sci USA 2001; 98:14769-14772.
19. Lu L, Jones R M, McBranch D, Whitten D. Surface-enhanced superquenching of cynine dyes as J-aggregates on laponite clay nanoparticles. Langmuir 2002; 18:7706-7713.
20. Jones R M, Bergstedt T S, McBranch D W, Whitten D G. Tuning of superquenching in layered and mixed fluorescent polyelectrolytes. J Am Chem Soc 2001; 123:6726-6727.
21. Kushon S A, Ley K D, Bradford K, Jones R M, McBranch D, Whitten D. Detection of DNA hybridization via fluorescent polymer superquenching. Langmuir 2002; 18:7245-7249.
22. Kushon S A, Bradford K, Marin V, Suhrada C, Armitage B A McBranch D W, Whitten D G. Detection of single nucleotide mismatches via fluorescent polymer superquenching. Langmuir 2003; 19:6456-6464.
23. Kumaraswamy S, Bergstedt T S, Shi X, Rininsland F, Kushon S, Xia W, Ley K, Achyuthan K, McBranch D, Whitten D. Fluorescent-conjugated polymer superquenching facilitates highly sensitive detection of proteases. Proc Natl Acad Sci USA 2004; 101:7511-7515.
24. Pinto M, Schanze K S. Amplified fluorescence sensing of protease activity with conjugated polyelectrolytes. Proc Natl Acad Sci USA 2004; 101:7505-7510.
25. Rininsland F, Xia W, Wittenburg S, Shi X, Stankewicz C, Achyuthan K, McBranch D, Whitten D. Metal ion-mediated polymer superquenching for highly sensitive detection of kinase and phosphatase activities. Proc Natl Acad Sci USA 2004; 101:15295-15300.
26. Xia W, Rininsland F, Wittenburg S K, Shi X, Achyuthan K E, McBranch D, Whitten D. Applications of fluorescent polymer superquenching to high throughput screening assays for protein kinases. Assay Drug Dev Technol 2004; 2:328-339.
27. Buranda T, Huang J, Ramarao G V, Ista L K, Larson R S, Ward T L, Sklar L A, Lopez G P. Biomimetic molecular assemblies on glass and mesoporous silica microbeads for biotechnology. Langmuir 2003; 19:1654-1663.
28. Edwards B S, Oprea T, Prossnitz E R, Sklar L A. Flow cytometry for high-throughput, high-content screening. Curr opin Chem Biol 2004; 8:392-398.
29. Sklar L A, Edwards B S, Graves S W, Nolan J P, Prossnitz E R. Flow cytometric analysis of ligand-receptor interactions and molecular assemblies. Annu Rev of Biophys Biomol struct 2002; 31:97-119.
30. Nolan J P, Sklar L A. Suspension array technology: evolution of the flat-array paradigm. Trends Biotechnol 2002; 20:9-12.
31. Bayerl T M, Bloom M. Physical properties of single phospholipids bilayers adsorbed to micro glass beads: A new vesicular model system studied by $^2$H-nuclear magnetic resonance. Biophys J 1990; 58:357-362.
32. Bayley H, Cremer P S. Stochastic sensors inspired by biology. Nature 2001; 413:226-230.
33. Anrather D, Smetazko M, Saba M, Alguel Y, Schalkhammer T. Supported membrane nanodevices. J Nanosci Nanotech 2004; 4:1-22.
34. Trojanowicz M, Mulchandani A. Analytical applications of planar bilayer lipid membranes. Anal Bioanal Chem 2004; 379:347-350.
35. Huang W, Yang X, Wang E. Mimetic membrane for biosensors. Anal Lett 2005; 38:3-18.
36. Schmidt J. Stochastic sensors. J Mater Chem 2005; 15:831-840.
37. Sackmann E. Supported membranes: Scientific and practical applications. Science 1996; 271:43-48.
38. Loidl-Stahlhofen A, Schmitt J, Noller J, Hartmann T, Brodowsky H, Schmitt W, Keldenich J. Solid-supported biomolecules on modified silica surfaces—A tool for fast physiocochemical characterization and high-throughput screening. Adv Mater 2001; 13:1829-1834.
39. Baksh M M, Jaros M, Groves J T. Detection of molecular interactions at membrane surface through colloid phase transition. Nature 2004; 427:139-141.
40. Ramey M B, Hiller J, Rubner M F, Tan C, Schanze K S, Reynolds J R. Amplified fluorescence quenching and electroluminescence of a cationic polyp-phenylene-co-thiophene)polyelectrolyte. Macromolecules 2005; 38:234-243.
41. Bayerl, T.; Bloom, M. *Biophys. J.* 1990, 58, 357-362.
42. Buranda, T.; Huang, J.; Ramamrao, G. V.; Ista, L. K.; Larson, R. S.; Ward, T. L.; Sklar, L. A.; Lopez, G. P. *Langmuir* 2003, 19, 1654-1663.
43. Buranda, T.; Huang, J.; Perez-Luna, V. H.; Schreyer, B.; Sklar, L. A.; Lopez, G. P. *Anal. Chem.* 2002, 74, 1149-1156.
44. Loidl-Stahlhofen, A.; Hartmann, T.; Schottner, M.; Rohring, C.; Brodowsky, H.; Schmitt, J.; Keldenich, J. *J. Pharm. Res.* 2001, 18, 1782-1788.
45. Loidl-Stahlhofen, A.; Schmitt, J.; Noller, J.; Hartmann, T.; Brodowsky, H.; Schmitt, W.; Keldenich, *J. Adv. Mater.* 2001, 13, 1829-1834.
46. Piyasena, M. E.; Buranda, T.; Wu, Y.; Huang, J.; Sklar, L. A.; Lopez, G. P. *Anal. Chem.* 2004, 76, 6266-6273.
47. Zeineldin, R.; Piyasena, M. E.; Bergstedt, T. S.; Sklar, L. A.; Whitten, D.; Lopez, G. P. *Cytometry*. Submitted for publication.
48. Chen, L.; McBranch, D. W.; Wang, H.-L.; Helgeson, R.; Wudl, F.; Whitten, D. G. *Proc. Natl. Acad. Sci. USA* 1999, 96, 12287-12292.
49. Chen, L.; McBranch, D. W.; Wang, R.; Whitten, D. *Chem. Phys. Lett.* 2000, 330, 27-33.
50. Harrison, B. S.; Ramey, M. B.; Reynolds, J. R.; Schanze, K. S. *J. Am. Chem. Soc.* 2000, 22, 8561-8562.

51. Wang, J.; Wang, D.; Miller, E. K.; Moses, D.; Bazan, G. C.; Heeger, A. J. *Macromolecules* 2000, 33, 5153-5158.
52. Tan, C.; Pinto, M. R.; Schanze, K. S. *Chem. Commun.* 2002, 2002(5), 446-447.
53. List, E. W. J.; Creely, C.; Leising, G.; Schulte, N.; Schlueter, A.; Scherf, U.; Muellen, K.; Graupner, W. *Chem. Phys. Lett.* 2000, 325, 132-138.
54. Gaylord, B. S.; Wang, S.; Heeger, A. J.; Bazan, G. C. *J. Am. Chem. Soc.* 2001, 123, 6417-6418.
55. Lu, L.; Helgeson, R.; Jones, R. M.; McBranch, D.; Whitten, D. *J. Am. Chem. Soc.* 2002, 124, 483-488.
56. Jones, R. M.; Lu, L.; Helgeson, R.; Bergstedt, T. S.; McBranch, D. W.; Whitten, D. G. *Proc. Natl. Acad. Sci. USA* 2001, 98, 14769-14772.
57. Jones, R. M.; Bergstedt, T. S.; McBranch, D. W.; Whitten, D. G. *J. Am. Chem. Soc.* 2001, 123, 6726-6727.
58. Kim, K.; Webster, S.; Levi, N.; Carroll, D. L.; Pinto, M. R.; Schanze, K. S. *Langmuir* 2005, 21, 5207-5211.
59. Kushon, S. A.; Ley, K. D.; Bradford, K.; Jones, R. M.; McBranch, D.; Whitten, D. *Langmuir* 2002, 18, 7245-7249.
60. Kushon, S. A.; Bradford, K.; Marin, V.; Suhrada, C.; Armitage, B. A.; McBranch, D. W.; Whitten, D. G. *Langmuir* 2003, 19, 6456-6464.
61. Kumaraswamy, S.; Bergstedt, T. S.; Shi, X.; Rininsland, F.; Kushon, S.; Xia, W.; Ley, K.; Achyuthan, K.; McBranch, D.; Whitten, D. *Proc. Natl. Acad. Sci. USA* 2004, 101, 7511-7515.
62. Pinto, M.; Schanze, K. S. *Proc. Natl. Acad. Sci. USA* 2004, 101, 7505-7510.
63. Rininsland, F.; Xia, W.; Wittenburg, S.; Shi, X.; Stankewicz, C.; Achyuthan, K.; McBranch, D.; Whitten, D. *Proc. Natl. Acad. Sci. USA* 2004, 101, 15295-15300.
64. Xia, W.; Rininsland, F.; Wittenburg, S. K.; Shi, X.; Achyuthan, K. E.; McBranch, D.; Whitten, D. *Assay Drug. Dev. Technol.* 2004, 2, 328-339.
65. Bayley, H.; Cremer, P. S. *Nature* 2001, 413, 226-230.
66. Anrather, D.; Smetazko, M.; Saba, M.; Alguel, Y.; Schalkhammer, T. *J. Nanosci. Nanotech.* 2004, 4, 1-22.
67. Trojanowicz, M.; Mulchandani, A. *Anal. Bioanal. Chem.* 2004, 379, 347-350.
68. Huang, W.; Yang, X.; Wang, E. *Anal. Lett.* 2005, 38, 3-18.
69. Schmidt, J. *J. Mater. Chem.* 2005, 5, 831-840.
70. Duffy, D. C.; McDonald, J. C.; Schueller, O. J. A.; Whitesides, G. M. *Anal. Chem.* 1998, 70, 4974-4984.
71. Ramey, M. B.; Hiller, J.; Rubner, M. F.; Tan, C.; Schanze, K. S.; Reynolds, J. R. *Macromolecules* 2005, 38, 234-243.
72. Bechinger, B. Crit. Rev. *Plant Sci.* 2004, 23, 271-292.
73. Ladokhin, A. S.; Selsted, M. E.; White, S. H. *Biophys. J.* 1997, 72, 1762-1766.
74. Ladokhin, A. S.; White, S. H. *Biochim. Biophys. Acta* 2001, 1514, 253-260.
75. Lee, T. H.; Mozsolits, H.; Aguilar, M. I. *J. Peptide Res.* 2001, 58, 464-476.
76. Kim, Y.; Lichtenbergova, L.; Snitko, Y.; Cho, W. *Anal. Chem.* 1997, 250, 109-116.
77. Dempsey, C. E. *Biochim. Biophys. Acta* 1990, 1031, 143-161.
78. Constantinescu, I.; Lafleur, M. *Biochim. Biophys. Acta* 2004, 1667, 26-37.
79. Sato, K.; Tokeshi, M.; Kimura, H.; Kitamori, T. *Anal. Chem.* 2001, 73, 1213-1218.
80. Sato, K.; Tokeshi, M.; Odake, T.; Kimura, H.; Ooi, T.; Nakao, M.; Kitamori, T. *Anal. Chem.* 2000, 72, 1144-1147.
81. Cho, W.; Bittova, L; Stahelin, R. V. *Anal. Biochem.* 2001, 296, 153-161.
82. Liu, X.-Y.; Nakamura, C.; Yang, Q.; Miyake, J. *Anal. Biochem.* 2001, 293, 251-257.
83. Mozsolits, H.; Lee, T.-H.; Wirth, H.-J.; Perlmutter, P.; Aguilar, M.-I. *Biophys. J.* 1999, 77, 1428-1444.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of identifying a test agent that disrupts a lipid bilayer, which comprises contacting a test agent with a lipid bilayer-coated bead that has a detectable label encapsulated by the lipid bilayer, and observing whether a signal from the detectable label is altered by a quenching molecule present in solution surrounding the bead when the lipid bilayer coated bead is exposed to the test agent.

2. The method of claim 1 wherein the bead is porous.

3. The method of claim 2 wherein the detectable label is present with in the pores of the porous bead.

4. The method of claim 2 wherein a detectable signal is emitted by the detectable label prior to addition of the test agent.

5. The method of claim 4 wherein the signal is reduced when the test agent disrupts the lipid bilayer.

6. The method of claim 5 further comprising detecting disruption of the lipid bilayer with flow cytometry.

7. The method of claim 2 wherein the detectable label is a fluorescent polymer.

8. The method of claim 2 wherein the detectable label is selected from the group consisting of: a fluorescent dye, an ion-sensitive dye, a pH-sensitive dye, an enzyme, a chemiluminescent molecule, a chromophore, an enzyme substrate, an enzyme cofactor, or an enzyme inhibitor.

9. The method of claim 2 wherein the test agent comprises a molecule, a drug, a detergent, a toxin, a polypeptide, a peptide, an antigen, an antibody, an enzyme, a receptor, a ligand, a nucleic acid, a virus, a liposome, a lipid, a surfactant, a toxin, or a combination thereof.

10. The method of claim 2 wherein the lipid bilayer further comprises a carbohydrate, protein, or combination thereof.

11. The method of claim 10 wherein the lipid bilayer further comprises a protein and wherein the protein is selected from the group consisting of: a cell membrane protein, antibody, immunoreceptor, or a cellular receptor.

12. The method of claim 2 wherein a linker is attached to the bead.

13. The method of claim 12 wherein the linker comprises an alkylene chain, a peptide, a glycan, or a lipid.

14. The method of claim 12 wherein the linker comprises biotin or streptavidin.

15. The method of claim 12 wherein the linker is also attached to an antigen or antibody.

* * * * *